United States Patent [19]

Miyamoto et al.

[11] Patent Number: 5,141,948
[45] Date of Patent: Aug. 25, 1992

[54] 2-SUBSTITUTED PHENYL-2-OXAZOLINE OR THIAZOLINE DERIVATIVES, PROCESS FOR PRODUCING THE SAME AND INSECTICIDES AND ACARICIDES CONTAINING THE SAME

[75] Inventors: Satoshi Miyamoto, Yokohama; Junji Suzuki; Yasuo Kikuchi, Nagano; Kazuya Toda, Nagano; Yoshiaki Itoh, Nagano; Tatsufumi Ikeda, Nagano; Tatsuya Ishida, Nagano; Tasuaki Hariya, Nagano; Yokichi Tsukidate, Nagano; Chiharu Morikawa, Suzaka, all of Japan

[73] Assignee: Yashima Chemical Industrial Co., Ltd., Tokyo, Japan

[21] Appl. No.: 625,918

[22] Filed: Dec. 10, 1990

[30] Foreign Application Priority Data

Dec. 9, 1989 [JP] Japan ................. 1-320420

[51] Int. Cl.$^5$ ................. A01N 43/76; A01N 43/78
[52] U.S. Cl. ................. 514/365; 514/374; 514/63; 548/146; 548/237; 548/239; 548/110; 546/14
[58] Field of Search .............. 548/146, 239, 237; 514/365, 378

[56] References Cited

U.S. PATENT DOCUMENTS

| | | | |
|---|---|---|---|
| 3,440,247 | 4/1969 | Dorer | 548/239 |
| 3,450,699 | 6/1969 | Seeliger et al. | 548/239 |
| 4,153,703 | 5/1979 | Harrison et al. | 514/365 |
| 4,977,171 | 12/1990 | Suzuki et al. | 548/237 |

FOREIGN PATENT DOCUMENTS

| | | |
|---|---|---|
| 0002812 | 7/1979 | European Pat. Off. |
| 0035475 | 9/1981 | European Pat. Off. |
| 0253213 | 1/1988 | European Pat. Off. |
| 0345775 | 12/1989 | European Pat. Off. |
| 3738680 | 5/1989 | Fed. Rep. of Germany |
| 2-85268 | 3/1990 | Japan |
| 80/02046 | 6/1982 | PCT Int'l Appl. |

OTHER PUBLICATIONS

Vorbruggen et al. Tetrahedron Let. vol. 22, pp. 4471-4474 (1981).
Tsuge et al. J. Org. Chem. vol. 52 pp. 2523-2530 (1987).
Jennings et al. Pesticide Biochem & Physiol. vol. 30 pp. 190-197 (1980).
Levine et al. J. Med. Chem. vol. 15, pp. 1030-1032 (1972).
Burakevich et al. J. Org. Chem. vol. 36, pp. 1-4 (1971).
Enders et al. Org. Syn. vol. 65, pp. 173-182 (1977).
Shaw et al. J. Org. Chem. vol. 23 pp. 27-32 (1950).

*Primary Examiner*—Donald G. Daus
*Attorney, Agent, or Firm*—Wenderoth, Lind & Ponack

[57] ABSTRACT

2-Substituted phenyl-2-oxazoline derivatives or 2-substituted phenyl-2-thiazoline derivatives represented by the general formula (I)

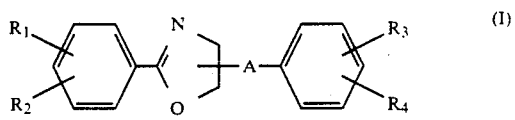

in which
$R_1$ and $R_2$ may be same or different and each represents a hydrogen atom, a halogen atom, a lower alkyl group, a lower alkoxy group, a nitro group, a lower haloalkyl group or a lower haloalkoxy group, with a proviso that $R_1$ and $R_2$ do not simultaneously represent hydrogen atoms;
$R_3$ represents a hydrogen atom, a halogen atom, a lower alkyl group or a lower alkoxy group;
$R_4$ represents an alkyl group having 7 or more carbon atoms, an alkoxy group having 7 or more carbon atoms, an alkylthio group, a lower alkoxy-lower alkyl group, a lower alkoxy-lower alkoxy group, an alkenyloxy group having 3 or more carbon atoms, a lower alkynyloxy group, a tri(lower alkyl) silyl group, a cycloalkyl group which may be substituted by a lower alkyl group, or a group indicated by

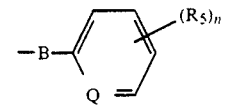

wherein B is a direct bond, an oxygen atom, a lower alkylene group, a lower alkyleneoxy group, a lower alkylenedioxy group or a di(lower alkyl) silyl group, Q is CH or N, n is 0 or an integer from 1 to 5, each $R_5$ is a halogen atom, an alkyl group, an alkoxy group, a lower haloalkyl group, a lower haloalkoxy group or a tri(lower alkyl) silyl group, and when n is greater than 1, $R_5$'s may be same or different;
A represents a direct bond or a lower alkylene group; and
Z represents an oxygen atom or a sulfur atom.

This compound is useful as an insecticidal and/or acaricidal (mitecidal) agent.

12 Claims, No Drawings

2-SUBSTITUTED PHENYL-2-OXAZOLINE OR THIAZOLINE DERIVATIVES, PROCESS FOR PRODUCING THE SAME AND INSECTICIDES AND ACARICIDES CONTAINING THE SAME

The present invention relates to a 2-substituted phenyl-2-oxazoline or thiazoline derivatives which are novel, a process for producing the same and an insecticide or an acaricide containing the same as the effective component.

Heretofore, several documents have been issued concerning 2,4-dipheyl-2-oxa- or thia-zoline.

For example, descriptions on the producing process for a certain kind of 2,4-diphenyl-2-oxa- or thia-zoline compounds may be found in Tetrahedron Letters, Volume 22, No. 45, pages 4471 to 4474 (1981); Chemical Abstracts, Volume 98, No. 19, 160087K (1983) and Journal of Organic Chemistry, Volume 52, pages 2523 to 2530 (1987).

Also, Official Announcement of Japanese Patent Application No. Sho 57-501962 and PCT International Application Publication No. WO 82/02046 disclose a process for producing $\Delta^2$-N-heterocyclic compounds. The publications include a description of the usefulness of these compounds as the intermediates for producing effective components in medicaments or the usefulness of the compounds per se as compounds having biological activity applicable to a medicine for diabetes. However, no descriptions on the preventing effect of the compounds against diseases or harmful insects for agricultural or horticultural plants.

A description on the effectiveness of a certain kind of 2-amino-2-oxazoline derivatives against mites (Acarina) or aphids is found in Pesticide Biochemistry and Physiology, Volume 30, pages 190 to 197 (1988).

Furthermore, the present inventors have previously found and proposed novel derivatives of 2,4-disubstituted 2-oxa- or thia-zoline having insecticidal and acaricidal activity (cf: EP-A-0345775).

The inventors have carried out studies in the course of developing novel insecticidal and acaricidal agents with an object of creating compounds having an insecticidal effect against harmful insects in a broad scope hitherto not known in the prior art technology despite the low toxicity.

Plant parasitic harmful insects and mites exert, as is well known, a serious effect of damaging on useful plants such as cereals including rice, wheat and the like, beans including soybean, red bean and the like, various fruit trees including apple, orange, pear and the like, vegetables including eggplant, cucumber, strawberry and the like, flowering plants including rose, carnation and the like, furthermore, tea plant and so forth, and many kinds of insecticides and/or acaricides are in practical use today.

However, a serious problem has been brought about in recent years by the development of the resistance (or tolerance) of the plant-parasitic harmful insects or mites against existing insecticides and/or acaricides and lowering of the preventing effect has been accepted as an inevitable problem in the cases of recurring use of any of the unitary kind of drugs. In order to avoid the problem of such development of resistance to drugs, there have been several proposals as the practical countermeasures thereto including successive replacement of new types of insecticides and/or acaricides avoiding repeated uses of identical drugs and combined use of drugs with distinctive mechanism of action.

The 2-amino-2-oxazoline derivatives described in Pesticide Biochemistry and Physiology, Volume 30, pages 190 to 197 (1988) as a kind of compounds within 2-oxazoline derivatives having insecticidal or acaricidal activity is characterized by containing an amino group in the 2-position of the oxazoline nucleus and the activity against mites or aphids thereof has been reported.

The description on 2-oxazoline derivatives di-substituted in the 2,4-position thereof disclosed in EP-A-0345775 shows the ovicidal activity against spider mites and the insecticidal activity against aphids, green rice leaf-hopper or brown rice leaf-hopper.

The inventors have completed the present invention by creating 2-substituted phenyl-2-oxa- or thiazoline derivatives which are novel, exhibit a prominent effect against harmful insects or mites in a wide scope but have low toxicity as the consequence of extensive studies in view of the above circumstance.

Thus, the present invention provides 2-substituted phenyl-2-oxazoline or thiazoline derivatives represented by the following general formula

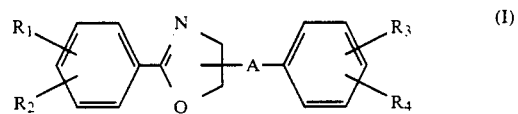

in which $R_1$ and $R_2$ may be same or different and each represents a hydrogen atom, a halogen atom, a lower alkyl group, a lower alkoxy group, a nitro group, a lower haloalkyl group or a lower haloalkoxy group, with a proviso that $R_1$ and $R_2$ do not simultaneously represents hydrogen atoms;

$R_3$ represents a hydrogen atom, a halogen atom, a lower alkyl group or a lower alkoxy group;

$R_4$ represents an alkyl group having 7 or more carbon atoms, an alkoxy group having 7 or more carbon atoms, an alkylthio group, a lower alkoxy-lower alkyl group, a lower alkoxy-lower alkoxy group, an alkenyloxy group having 3 or more of carbon atoms, a lower alkynyloxy group, a tri(lower alkyl) silyl group, a cycloalkyl group which may be substituted by a lower alkyl group, or a group indicated by

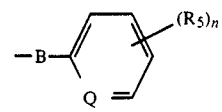

wherein B is a direct bond, a oxygen atom, a lower alkylene group, a lower alkyleneoxy group, a lower alkylenedioxy group or a di(lower alkyl) silyl group, Q is CH or N, n is 0 or an integer from 1 to 5 and each $R_5$ represents a halogen atom, an alkyl group, an alkoxy group, a lower haloalkyl group, a lower haloalkoxy group or a tri(lower alkyl) silyl group, when n is greater than 1, $R_5$'s may be same or different;

A represents a direct bond or a lower alkylene group; and Z represents an oxygen atom or a sulfur atom.

The terms "lower" used herein mean that the number of carbon atoms in the groups or compounds featured by this term is 6 or less.

The terms "halogen atom" imply a fluorine, chlorine, bromine and iodine atom.

The terms "alkyl group" may be in the form of either linear chain or branched chain and exemplified by alkyl groups having 1 to 20 or, preferably, 1 to 15 carbon atoms including a methyl, an ethyl, a n-propyl, an isopropyl, a n-butyl, an isobutyl, a sec-butyl, a tert-butyl, a n-pentyl, an isoamyl, a neopentyl, a n-hexyl, a n-heptyl, a 1,1-dimethyl pentyl, a n-octyl, a 1-methyl heptyl, a 1,1-dimethyl heptyl, a 1,1-dimethyl-4-methyl pentyl, a n-nonyl, a n-decyl, a 4,8-dimethyl nonyl, a n-undecyl, a 1-pentyl hexyl, a n-dodecyl, a n-tridecyl, a n-tetradecyl, a n-pentadecyl, a n-hexadecyl, a n-octadecyl, a n-nonadecyl, n-eicosyl group and the like.

The terms "alkoxy group" and "alkylthio group" indicate an (alkyl)-O- group and an (alkyl)-S- group, respectively, in which the part of "alkyl" has the meaning specified in the above.

The terms "haloalkyl group" indicate an alkyl group in which at least one of the hydrogen atoms connected to the carbon atom in the alkyl group is substituted by a halogen atom comprising specifically a chloromethyl, trifluoromethyl, fluoroethyl, trifluoroethyl, perfluoroethyl group and the like and the terms "haloalkoxy group" denote a (haloalkyl)-O- group in which the portion of haloalkyl has the same meaning as mentioned in the above such as a trifluoromethoxy group and the like.

The terms "lower alkoxy-lower alkyl group" indicate a (lower alkyl)-O-(lower alkyl) group wherein the alkyl portion has the same meaning as above as exemplified by an ethoxymethyl, n-propoxy methyl, isopropoxy methyl, n-butoxy methyl, isobutoxy methyl, 2-methoxyethyl, 2-ethoxy ethyl group and the like.

The terms "lower alkoxy-lower alkoxy group" indicate a (lower alkyl)-O-(lower alkyl)-O- group which comprises, for example, a 2-methoxy-ethoxy, 2-ethoxyethoxy, 2-n-propoxy-ethoxy, 4-isopropoxy-butoxy group and the like.

The terms "alkenyloxy group" indicate an (alkenyl)-O- group in which the alkenyl portion is an alkenyl group in the form of a linear chain or a branched chain as exemplified by alkenyloxy groups having 3 to 15 carbon atoms including an allyloxy, butenyloxy, 3-methyl-2-butenyloxy, geranyloxy, farnesyloxy, citronellyloxy group and the like.

The terms "lower alkynyloxy group" are exemplified by propargyloxy group and the like.

The terms "tri(lower alkyl) silyl group" denote, for example, a trimethyl silyl, ethyl dimethyl silyl, n-propyl dimethyl silyl, tert-butyl dimethyl silyl, triethyl silyl, methyl diethyl silyl group and the like.

The terms "cycloalkyl group" imply those having 3 to 8 carbon atoms such as a cyclohexyl group and the cycloalkyl group may be optionally substituted with a lower alkyl group. Such substituted cycloalkyl groups are exemplified by a methyl cyclohexyl, ethyl cyclohexyl, tert-butyl cyclohexyl group and the like.

The "lower alkylene group" may be in a form of either a linear chain or branched chain and exemplified by $$-CH_2-, -CH_2-CH_2-, -\underset{\underset{CH_3}{|}}{CH}-, -CH_2-CH_2-CH_2-,$$

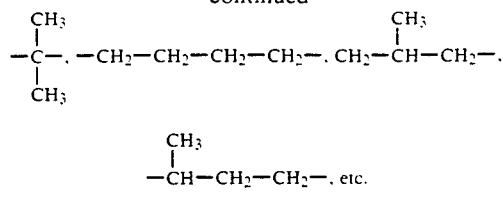

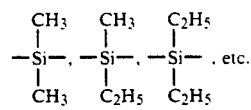

The terms "lower alkyleneoxy group" and "lower alkylenedioxy group" each indicates an -O-(lower alkylene)- group and an -O-(lower alkylene)-O- group, respectively, in which the portion of the lower alkylene has a meaning mentioned in the above.

The "di(lower alkyl) silyl group" is exemplified by

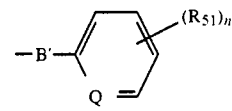

However, each of the symbols $R_1$ and $R_2$ in the above-mentioned general formula (I) is preferred to be, either identically or differently, a hydrogen atom, a halogen atom, methyl group, methoxy group, trifluoromethyl group or trifluoro-methoxy group, with a proviso that $R_1$ and $R_2$ do not simultaneously represent a hydrogen atom. The substituting atom or group should preferably be at the 2-, 4- or 6-position in the benzene nucleus.

In particular, the cases in which each of $R_1$ and $R_2$ represents an halogen atom with preferene to a fluorine atom or a chlorine atom are the more favorable.

The symbol $R_4$ therein should preferably be positioned at the 4-position in the benzene nucleus and should preferably represent an alkyl group with 7 to 12 carbon atoms or a group indicated by the formula

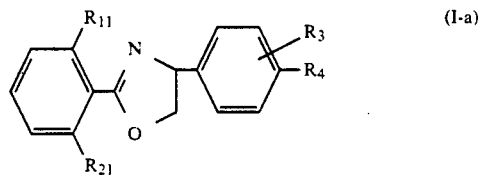

wherein B' is a direct bond, —O—, —CH$_2$— or —OCH$_2$—, Q is CH or N; n is 0 or an integer from 1 to 5; $R_{51}$ represents a halogen atom, an alkyl group or an alkoxy group, and when n is greater than 1, $R_{51}$'s may be same or different; A is preferably a direct bond; and Z should preferably be an oxygen atom in the general meaning.

In the above-mentioned general formula (I), the class of the preferred compounds is 2-substituted phenyl-2-oxazoline derivative represented by the formula ![structure (I-a)]

in which $R_{11}$ and $R_{21}$ may be same or different and each represents a halogen atom, and $R_3$ and $R_4$ have the same meaning as described in the above.

As the classes of the more preferred compounds within the compounds of the above formula (I-a), 2-substituted phenyl-2-oxazoline derivatives represented by any of the following formulas may be listed.

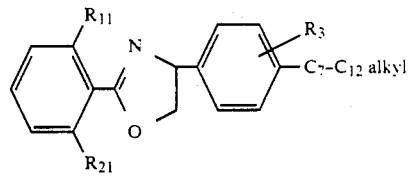

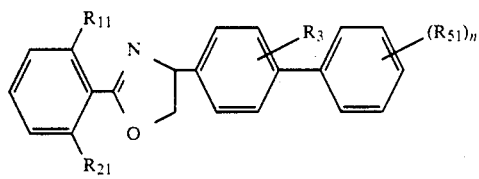

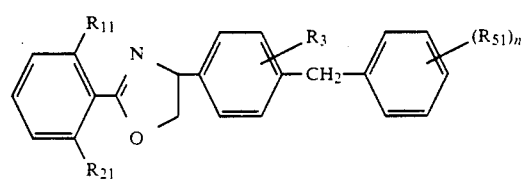

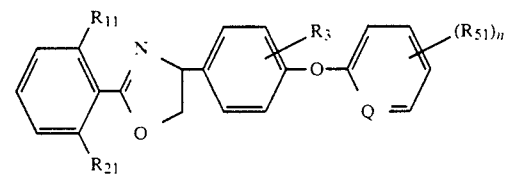

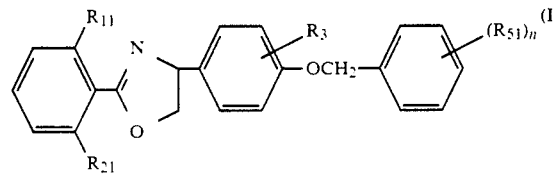

In each of the above formulas, each $R_{51}$ represents a halogen atom, an alkyl group or an alkoxy group, when n is greater than 1, $R_{51}$'s may be same or different, each of $R_{11}$, $R_{21}$, $R_3$, Q and n has the same meaning as above-indicated.

The compounds of the present invention can be produced by (a) reacting a substituted benzoic acid represented by the general formula

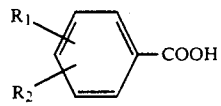

wherein each of $R_1$ and $R_2$ has the same meaning described in the above, with aminoalcohol derivative represented by the general formula

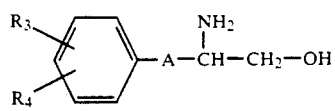

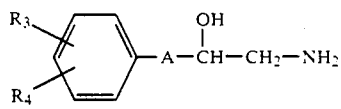

wherein each of $R_3$, $R_4$ and A has the same meaning as described in the above, or (b) treating an amide alcohol derivative represented by the general formula

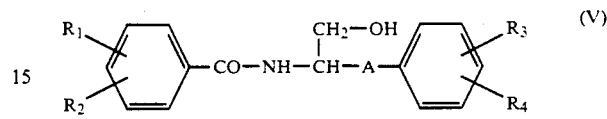

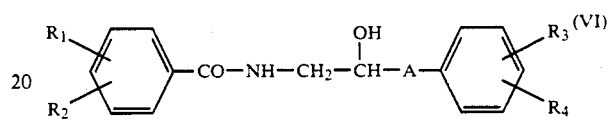

wherein each of $R_1$, $R_2$, $R_3$, $R_4$ and A has the same meaning as described in the above, with a dehydrating agent; or (c) treating a compound represented by the general formula

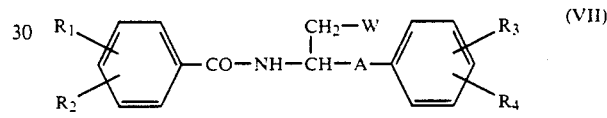

wherein each of $R_1$, $R_2$, $R_3$, $R_4$ and A has the same meaning as described above, and W is a halogen atom, an alkylsulfonyloxy group (such as a methane sulfonyloxy group) or a aryl sulfonyloxy group (such as a p-toluene sulfonyloxy group) with a base.

The reaction of the benzoic acid compound of the formula (II) with the amino alcohol derivative of the formula (III) or (IV) in the method (a) may be carried out usually in a suitable solvent such as an aromatic hydrocarbon solvent including benzene, toluene, xylene, nitrobenzene, chlorobenzene, dichlorobenzene and the like at a temperature from about 70° C. to the boiling point of the solvent with a dehydrating agent.

The dehydrating agent used in the above reaction is exemplified by sulfuric acid, polyphosphoric acid, phosphorus pentoxide, dicyclohexyl carbodiimide (DCC), phosphorus pentasulfide and the like and a compound of the formula (I) in which Z is an oxygen atom is obtained in the cases of using the dehydrating agent such as sulfuric acid, polyphosphoric acid, phosphorus pentoxide, DCC and the like and a compound of the formula (I) in which Z is a sulfur atom is obtained in the cases of using a dehydrating agent such as phosphorus pentasulfide and the like.

The molar ratio of the compound of the formula (II) and the amino alcohol derivative of the formula (III) or (IV) in the reaction should not be limited strictly but preferably the amino alcohol derivative of the formula (III) or (IV) should be used in an amount of 0.8 to 1.2 moles for 1 mole of the compound of the formula (II) as usual. Also, the amount of the above dehydrating agent to be used should not be restricted strictly but the amount should preferably be in the range of 2 to 8 moles for 1 mole of the compound of the formula (II).

The treatment of amide alcohol derivative of the formula (V) or (VI) with a dehydrating agent in the method (b) may be carried out under a condition mentioned for the method (a).

The amide alcohol derivatives of the formula (V) or (VI) used as the starting material in the above method (b) may be produced by the reaction of a reactive derivative of the substituted benzoic acid of the above formula (II) such as halides including chlorides, bromides and the like with the aminoalcohol derivative of the formula (III) or (IV) in the presence of a base.

This reaction is usually carried out in a solvent. Examples of the suitable solvent include water, alcohols such as methanol, ethanol and the like, ethers such as diethyl ether, tetrahydrofuran, dioxane, diglyme and the like, aromatic hydrocarbons such as benzene, toluene, xylene and the like, halogenated hydrocarbons such as dichloromethane, chloroform, carbon tetrachloride, dichloroethane and the like. The suitable reaction temperature is in the range of 0° C. to about 50° C. in general.

On the other hand, the base to be used is exemplified by inorganic bases such as sodium hydroxide, potassium hydroxide, potassium carbonate and the like, organic tertiary bases such as triethyl amine, N,N-dimethyl aniline, pyridine, 4-N,N-dimethylamino pyridine and the like.

In the above reaction, the molar ratio of the reactive derivative of the compound of the formula (II) to the aminoalcohol derivative of the formula (III) or (IV) is not particularly limitative but the aminoalcohol derivative of the formula (III) or (IV) should preferably be used in a molar ratio in the range of 0.8 to 1.2 moles to 1 mole of the reactive derivative of compound of the formula (II) and use of the base in a ratio of 0.8 to 1.2 equivalents to 1 mole of the reactive derivative of the compound of the formula (II) is considered as convenient.

The compound of the formula (VII) in the above reaction (c) may be obtained by the reaction of the compound of the formula (V) used as the starting material in the above reaction (b) with a halogenating agent or a sulfonating agent.

The reaction of halogenation or sulfonation in this case may be carried out usually in a solvent.

The useful solvents for the reaction are exemplified by aromatic hydrocarbons such as benzene, toluene, xylene and the like, halogenated hydrocarbons such as dichloromethane, chloroform, carbon tetrachloride, dichloroethane and the like and ethers such as diethyl ether, tetrahydrofuran, dioxane, diglyme and the like. Examples of the useful halogenating agent include thionyl chloride, thionyl bromide, phosphorus oxychloride, phosphorus trichloride, phosphorus tribromide and the like and examples of the useful sulfonating agent include methane sulfonyl chloride, p-toluene sulfonyl chloride and the like.

The appropriate reaction temperature in this case is usually from about 0° C. to the boiling point of the solvent.

The ratio of the halogenating agent or the sulfonating agent to be used to the compound of the formula (V) is also not strictly limitative but in general use of the halogenating agent or the sulfonating agent in the range of 1 to 6 moles to 1 mole of the compound of the formula (V) is appropriate.

The reaction of the produced compound of the formula (VII) for ring closure with a base may be advantageously carried out in a solvent including water and alcohols such as methanol, ethanol and the like at a temperature in the range of from about 40° C. to about 100° C. as usual. The inorganic bases above-mentioned for the reaction (b) is suitable as the base in this case and the appropriate amount thereof to be used is 1 to 6 equivalents to 1 mole of the compound of the formula (VII).

The inventive compounds of the formula (I) obtained by any of the reactions (a), (b) and (c) can be isolated and purified by the method known per se such as column chromatography, recrystallization and the like.

The solvent for column chromatography or recrystallization should be selected from, for example, benzene, methyl alcohol, ethyl alcohol, chloroform, n-hexane, ethyl acetate ane the like, and mixtures containing them.

Production of the inventive compounds is further specifically explained in the following referring to the synthesis examples.

SYNTHESIS EXAMPLE 1

Synthesis of 2-(2,6-difluorophenyl)-4-(4-n-decyloxyphenyl)-2-oxazoline

To a mixture of 2.93 g (10 millimoles) of 2-amino-2-(4-n-decyloxyphenyl)ethanol, 1.01 g (10 millimoles) of triethyl amine and 30 ml of tetrahydrofuran contained in a 100 ml eggplant-shaped (spheroidal) flask a solution of 1.77 g (10 millimoles) of 2. 6-difluorobenzoyl chloride in 15 ml of tetrahydrofuran was added over 30 minutes with stirring at ice-bath temperature. After further continuation of stirring for 3 hours at room temperature, the produced triethylamine hydrochloride was removed by filtration using a glass filter and the filtrate was concentrated under reduced pressure. The concentrate was added with 50 ml of toluene and 2.84 g (20 millimoles) of phosphorus pentoxide and then refluxed for 3 hours in an oil bath. The reaction mixture was washed successively with 50 ml of 10% aqueous solution of sodium hydroxide and them with a saturated aqueous sodium chloride solution after cooling to room temperature with subsequent desiccation over anhydrous sodium sulfate and concentration under reduced pressure. This concentrate was purified by silica-gel column chromatography using a 8/2 solvent mixture of n-hexane/ethyl acetate as a movable phase to obtain 2-(2,6-difluorophenyl)-4-(4-n-decyloxyphenyl)-2-oxazoline (Compound Number 94, shown below in the Table).

[pale yellow liquid, $n_D^{25}$ 1.5236, yield 2.15 g (51.8%)]
$^1$H NMR ($_{TMS}$ $^{CDCl_3}$ ppm): 0.90 (t) J=6 Hz 3H 1.1-2.1 (m) 16H 3.95 (t) J=6 Hz 2H 4.30 (t) J=8 Hz 1H 4.87 (t) J=8 Hz 1H 5.85 (t) J=8 Hz 1H 7.1-7.9 (m) 7H
IR ($_{max}$ $^{KBr}$ cm$^{-1}$): 2810-3135 (C—H), 1670 (C=N)

SYNTHESIS EXAMPLE 2

Synthesis of 2-(2-chloro-6-fluorophenyl)-4-(3-phenyl-4-methoxyphenyl)-2-oxazoline To a mixture of 2.43 g (10 millimoles) of 2-amino-2-(3-phenyl-4-methoxyphenyl)ethanol, 1.01 g (10 millimoles) of triethylamine and 30 ml of tetrahydrofuran contained in a 100 ml eggplant-shaped (spheroidal) flask, a solution of 1.93 g (10 millimoles) of 2-chloro-6-fluorobenzoyl chloride in 15 ml of tetrahydrofuran was added over 30 minutes with stirring at ice-bath temperature. After further continuation of stirring for 3 hours at room temperature, the produced triethylamine hydrochloride was removed by filtration using a glass filter and the filtrate was concentrated under reduced pressure. To this concentrate diluted with 30 ml of benzene in a 100 ml eggplant-shaped flask, 4.76 g (40 millimoles) of thionyl chloride was added at once and refluxed for 3 hours with stirring on an oil bath. The reaction mixture was cooled to room temperature, and benzene and excess thionyl chloride were evaporated under reduced pressure. Thereafter the residue was added with 30 ml of methanol and 5 ml of a 30% aqueous sodium hydroxide solution followed by stirring for 20 minutes at 70° C. on an oil bath and then concentrated under reduced pressure. The concentrate added with 100 ml of benzene was washed with a saturated aqueous sodium chloride solution, desiccated over anhydrous sodium sulfate and then concentrated under reduced pressure.

This concentrate was purified by silica-gel column chromatography using a 8/2 solvent mixture of n-hexane/ethyl acetate as a movable phase to obtain 2-(2-chloro-6-fluorophenyl)-4-(3-phenyl-4-methoxyphenyl)-2-oxazoline (Compound Number 147).

[pale yellow solid, melting point 80.5° to 82.0° C., yield 1.8 g (47.4%)]

$^1$H NMR ($_{TMS}$ $^{CDCl_3}$ ppm): 3.73 (s) 3H, 4.30 (t) J=9 Hz 1H, 4.82 (t) J=9 Hz 1H, 5.48 (t) J=9 Hz 1H, 6.80-7.7 (m) 11H IR($_{max}$ $^{KBr}$ cm$^{-1}$): 2800-3150 (C=H), 1664 (C=N)

SYNTHESIS EXAMPLE 3

Synthesis of 2-(2,6-difluorophenyl)-4-(4-n-decylphenyl)-2-oxazoline

To a mixture of 2.77 g (10 millimoles) of 2-amino-2-(4-n-decylphenyl)ethanol, 1.01 g (10 millimoles) of triethylamine and 30 ml of tetrahydrofuran contained in a 100 ml eggplant-shaped (spheroidal) flask, a solution of 1.77 g (10 millimoles) of 2,6-difluorobenzoyl chloride in 15 ml of tetrahydrofuran was added over 30 minutes with stirring at ice-bath temperature. After further continuation of stirring for 3 hours at room temperature, the produced triethylamine hydrochloride was removed by filtration using a glass filter and the filtrate was concentrated under reduced pressure. This concentrate was added with 50 ml of benzene and 3.57 g (30 millimoles) of thionyl chloride, and then refluxed for 3 hours with stirring on an oil bath. The reaction mixture was concentrated under reduced pressure and added with 50 ml of methanol followed by dropwise addition of 2 ml of a 50% aqueous sodium hydroxide solution at 60° C. with stirring. After further continuation of stirring for 30 minutes, the reaction mixture was poured into water and extracted with ethyl acetate followed by desiccation over anhydrous sodium sulfate and concentration under reduced pressure. This concentrate was purified by silica-gel column chromatography using a 8/2 solvent mixture of n-hexane/ethyl acetate as a movable phase to obtain 2-(2,6-difluorophenyl)-4-(4-n-decylphenyl)-2-oxazoline (Compound Number 20).

[pale yellow liquid, $n_D^{25}$ 1.5241, yield 3.4 g (85.2%)]

$^1$H NMR ($_{TMS}$ $^{CDCl_3}$ ppm ): 0.90 (t) J=6 Hz 3H, 1.1-2.0 (m) 16H, 2.66 (t) J=7 Hz 2H, 4.33 (t) J=8 Hz 1H, 4.87 (t) J=8 Hz 1H, 5.50 (t) J=8 Hz 1H, 6.8-7.7 (m) 7H IR($_{max}$ $^{KBr}$ cm$^{-1}$): 2856-2928 (C—H), 1668 (C=N)

SYNTHESIS EXAMPLE 4

Synthesis of 2-(2-chloro-6-fluorophenyl)-5-(4-n-octyloxyphenyl)-2-thiazoline

To a mixture of 2.65 g (10 millimoles) of 2-amino-1-(4-n-octyloxyphenyl)ethanol, 1.01 g (10 millimoles) of triethylamine and 30 ml of tetrahydrofuran contained in a 100 ml eggplant-shaped (spheroidal) flask, a solution of 1.93 g (10 millimoles) of 2-chloro-6-fluorobenzoyl chloride dissolved in 10 ml of tetrahydrofuran was added over 30 minutes with stirring at ice-bath temperature. After further continuation of stirring for 3 hours at room temperature, the produced triethylamine hydrochloride was removed by filtration using a glass filter and the filtrate was concentrated under reduced pressure. To this concentrate and 30 ml of toluene contained in a 100 ml eggplant-shaped flask, 4.44 g (20 millimoles) of phosphorus pentasulfide was added at once and refluxed for 4 hours on an oil bath with stirring. After cooling to room temperature, the reaction mixture was added with 40 ml of a 30% aqueous sodium hydroxide solution and stirred for 1 hour at room temperature. The reaction liquid was added with 100 ml of benzene and washed with a saturated aqueous sodium chloride solution followed by desiccation over anhydrous sodium sulfate and concentrated under reduced pressure. This concentrate was purified by silica-gel column chromatography using a 8/2 solvent mixture of n-hexane/ethyl acetate as a movable phase to obtain 2-(2-chloro-6-fluorophenyl)-5-(4-n-octyloxyphenyl)-2-thiazoline (Compound Number 91).

[pale yellow solid, melting point 41.0° to 41.5° C., yield 3.20 g (76.2%)]

$^1$H NMR ($_{TMS}$ $^{CDCl_3}$ ppm): 0.87 (t) J=6 Hz 3H, 1.10-2.03 (m) 12H, 3.93 (t) J=6 Hz 2H, 4.70 (dd) 2H, 5.17 (t) J=7 Hz 1H, 6.77-7.47 (m) 7H IR ($_{max}$ $^{KBr}$ cm$^{-1}$): 2800-3150 (C—H), b 1620 (C=N),

SYNTHESIS EXAMPLE 5

Synthesis of 2-(2,6-difluorophenyl)-4-(4-n-octylphenyl)-2-oxazoline

To a mixture of 2.49 g (10 millimoles) of 2-amino-2-(4-n-octylphenyl)ethanol, 1.01 g (10 millimoles) of triethylamine and 30 ml of tetrahydrofuran, a solution of 1.77 g (10 millimoles) of 2,6-difluorobenzoyl chloride in 15 ml of tetrahydrofuran was added over 30 minutes with stirring at ice-bath temperature. After further continuation of stirring at room temperature for 3 hours the reaction mixture was filtered and the filtrate was concentrated under reduced pressure. A mixture of this concentrate, 30 ml of benzene and 3.57 g (30 millimoles) of thionyl chloride was refluxed for 3 hours on an oil bath. The reaction mixture was cooled to room temperature and concentrated under reduced pressure. The concentrate was added with 30 ml of methanol followed by further addition of 4 ml of a 30% aqueous sodium hydroxide solution over 10 minutes while being kept at 70° C. with stirring.

Thereafter, following stirring at 70° C. for 20 minutes and cooling again to room temperature, the reaction mixture was extracted with ethyl acetate, washed with a saturated aqueous sodium chloride solution, desiccated over anhydrous sodium sulfate and concentrated under reduced pressure. This concentrate was purified by silica-gel column chromatography using a 8/2 solvent of n-hexane/ethyl acetate as a movable phase to obtain 2-(2,6-difluorophenyl)-4-(4-n-oxtylphenyl)-2-oxazoline (Compound Number 6).

[colorless oil substance, $n_D^{25}$ 1.5226, yield 3.1 g (83.6%)] $^1$H NMR ($_{TMS}$ $^{CDCl_3}$ ppm): 0.57–1.73 (m) 15H, 2.60 (t) J=8 Hz 2H, 4.20 (t) J=8 Hz 1H, 4.70 (t) J=8 Hz 1H, 5.37 (dd) J=8 Hz 1H, J=10 Hz, 6.73–7.57 (m) 7H IR ($_{max}$ $^{KBr}$ cm$^{-1}$): 1670 (C=N)

SYNTHESIS EXAMPLE 6

Synthesis of 2-(2,6-difluorophenyl)-4-[4-(2,4-dichlorobenzyloxy)-phenyl]-2-oxazoline To a mixture of 3.12 g (10 millimoles) of 2-amino-2-[4-(2,4-dichlorobenzyloxy)phenyl]ethanol, 1.01 g (10 millimoles) of triethylamine and 30 ml of tetrahydrofuran, a solution of 1.77 g (10 millimoles) of 2,6-difluorobenzoyl chloride dissolved in 15 ml of tetrahydrofuran was added over 30 minutes with stirring at ice-bath temperature. After further continuation of stirring at room temperature for 3 hours, the reaction mixture was filtered and the filtrate was concentrated under reduced pressure. This concentrate was added with 30 ml of tetrahydrofuran and 1.01 g (10 millimoles) of triethylamine and further added with 1.15 g (10 millimoles) of methane sulfonyl chloride dissolved in 15 ml of tetrahydrofuran over 30 minutes with stirring at ice-bath temperature.

After further continuation of stirring for 3 hours at room temperature, the reaction mixture was filtered and the filtrate was concentrated under reduced pressure.

This concentrate was added with 50 ml of methanol and 1.00 g (15 millimoles) of 85% potassium hydroxide and stirred for 2 hours at 70° C. After cooling again to room temperature, the reaction mixture was extracted with ethyl acetate, washed with a saturated aqueous sodium chloride solution, desiccated over anhyrous sodium sulfate and concentrated under reduced pressure. This concentrate was purified by silica-gel column chromatography using a 8/2 solvent mixture of n-hexane/ethyl acetate to obtain 2-(2,6-difluorophenyl)-4-[4-(2,4-dichlorobenzyloxy)phenyl]-2-oxazoline (Compound Number 359).

[colorless crystal. melting point 104.0° to 104.5° C., yield 3.5 g (80.6%)

$^1$H NMR ($_{TMS}$ $^{CDCl_3}$ ppm): 4.30 (t) J=9 Hz 1H, 4.83 (t) J=9 Hz 1H, 5.17 (s) 2H, 5.50 (t) J=9 Hz 1H, 6.80–7.75 (m) 10H, IR ($_{max}$ $^{KBr}$ cm$^{-1}$): 1670 (C=N)

SYNTHESIS EXAMPLE 7

Synthesis of 2-(2,6-difluorophenyl)-4-(2-fluoro-4-n-nonylphenyl)-2-oxazoline

To a mixture of 2.81 g (10 millimoles) of 2-amino-2-(2-fluoro-4-n-nonylphenyl)ethanol, 1.77 g (10 millimoles) of 2,6-difluorobenzoic acid and 20 ml of toluene, 3 g (30 millimoles) of concentrated sulfuric acid was added and refluxed for 7 hours with stirring. After cooling again to room temperature, the reaction mixture was washed successively with 30 ml of a 10% aqueous sodium hydroxide solution and then 30 ml of a saturated sodium chloride solution, desiccated over anhydrous sodium sulfate and concentrated under reduced pressure. This concentrate was purified by silica-gel column chromatography using a 8/2 solvent mixture of n-hexane/ethyl acetate to obtain 2-(2,6-difluorophenyl)-4-(2-fluoro-4-n-nonylphenyl)-2-oxazoline (Compound Number 42).

[pale brown oily substance, $n_D^{25}$ 1.5184, yield 2.27 g (66.2%)]

$^1$H NMR ($_{TMS}$ $^{CDCl_3}$ ppm): 0.7–1.9 (m) 17H, 2.65 (t) J=8 Hz 2H, 4.31 (t) J=8 Hz 1H, 4.90 (t) J=8 Hz 1H, 5.82 (dd) J=8 Hz 1H, J=10 Hz, 6.8–7.7 (m) 6H IR ($_{max}$ $^{KBr}$ cm$^{-1}$): 1655 (C=N)

The other compounds shown in the following Table 1 were synthesized in the smilar manner to Synthesis Examples 1 to 7. Table 1 also includes the compounds shown in Synthesis Examples 1 to 7.

The physical data in the table indicate the referactive index ($n_D^{25}$) except those noted with a symbol * which indicate the melting point (°C.).

Each of the abbreviations used in the table has the following meaning, respectively.

| Me = methyl | Bu = butyl |
|---|---|
| Et = ethyl | Pen = pentyl |
| Pr = propyl | Hex = hexyl |

TABLE 1

| Compound No. | Structural formula | Physical Constant |
|---|---|---|
| 1 | n-Heptyl—[phenyl]—CH(N=)—CH₂—O— with 2,6-difluorophenyl | 1.5322 |
| 2 | n-Heptyl—[phenyl]—CH(N=)—CH₂—O— with 2-Cl,6-F-phenyl | 1.5432 |

-continued
| | | |
|---|---|---|
| 3 | 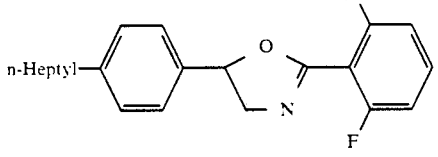 | 1.5447 |
| 4 | 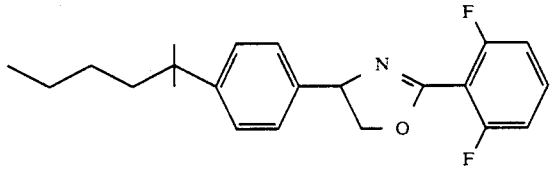 | 1.5398 |
| 5 | 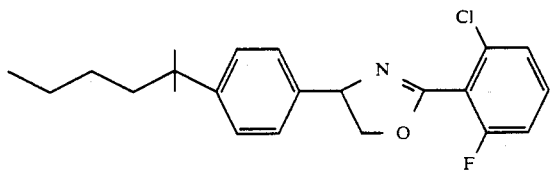 | 1.5496 |
| 6 | 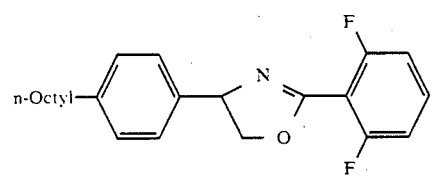 | 1.5226 |
| 7 | 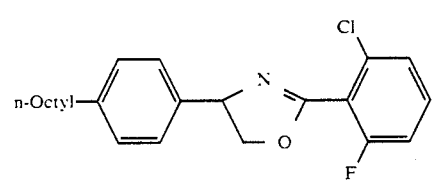 | 1.5399 |
| 8 | 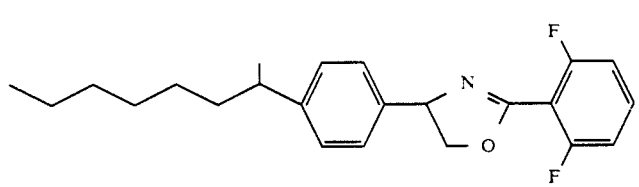 | 1.5290 |
| 9 | 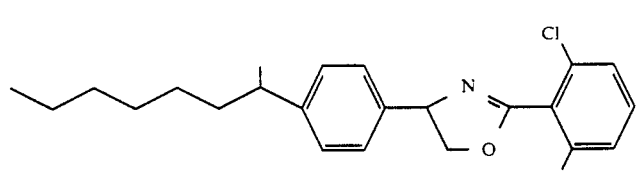 | 1.5387 |
| 10 | 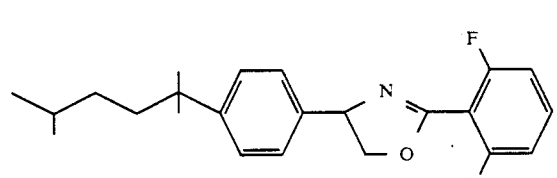 | 1.5484 |
| 11 | 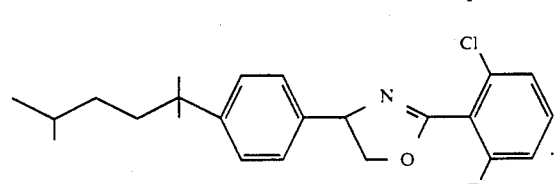 | 1.5625 |

-continued
| | | |
|---|---|---|
| 12 | 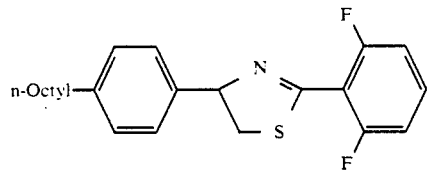 | 1.5553 |
| 13 | 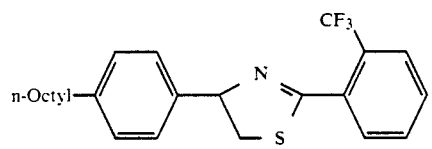 | 1.5166 |
| 14 | 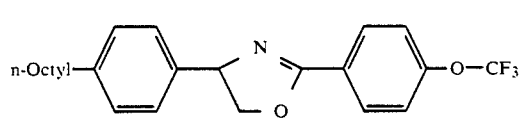 | 30.5~63* |
| 15 | 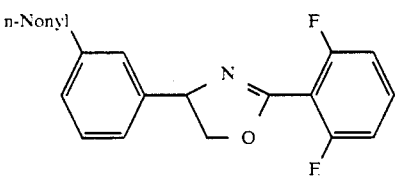 | 1.5284 |
| 16 | 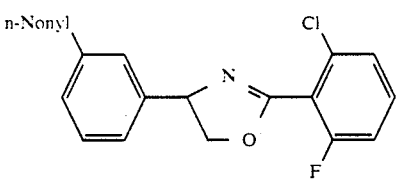 | 1.5402 |
| 17 | 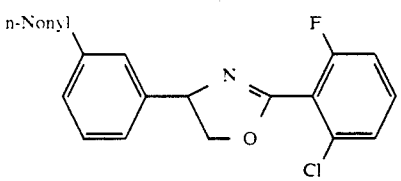 | 1.5528 |
| 18 | 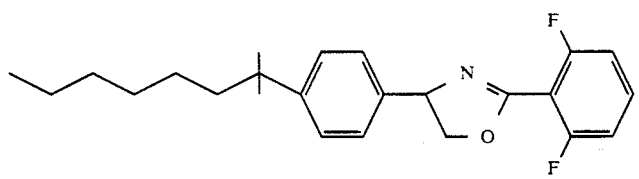 | 1.5342 |
| 19 | 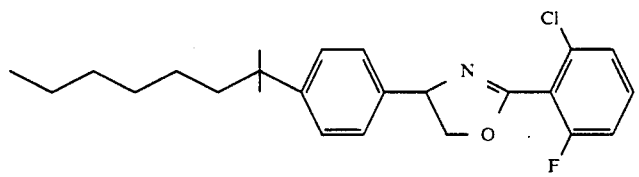 | 1.5443 |
| 20 | 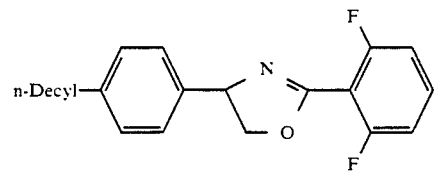 | 1.5241 |

-continued
| | | |
|---|---|---|
| 21 | 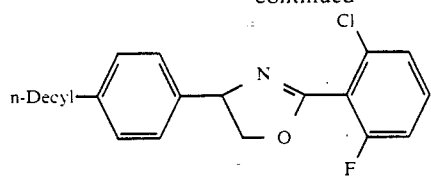 | 1.5388 |
| 22 | 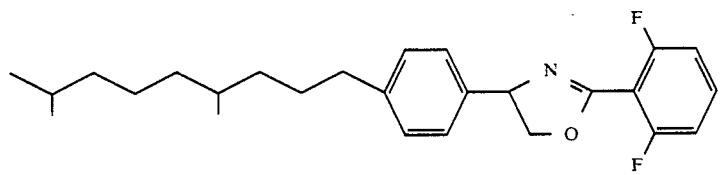 | 1.5315 |
| 23 | 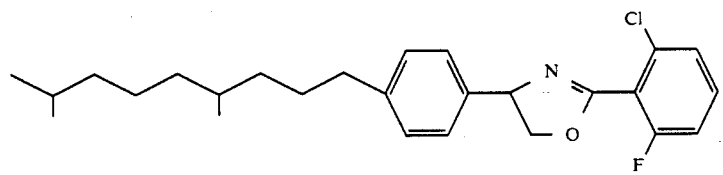 | 1.5405 |
| 24 | 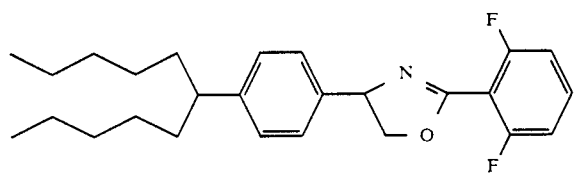 | 1.5228 |
| 25 | 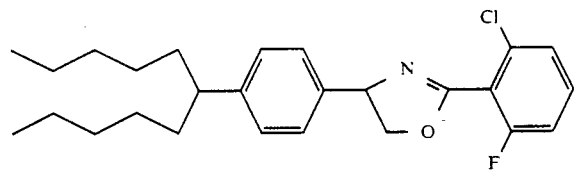 | 1.5234 |
| 26 | 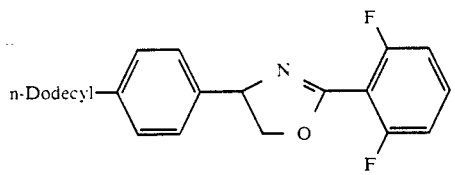 | 1.5194 |
| 27 | 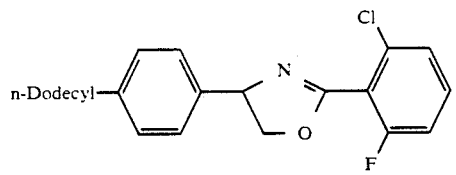 | 1.5289 |
| 28 | 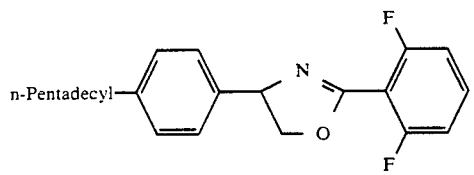 | 1.5352 |
| 29 | 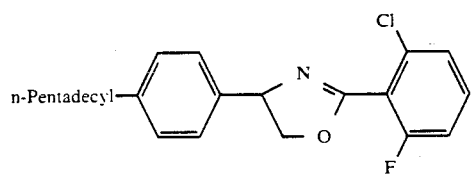 | 97~100* |

-continued
30 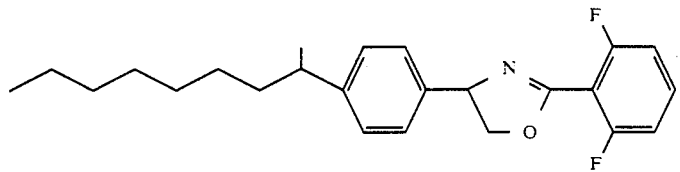 1.5294
31 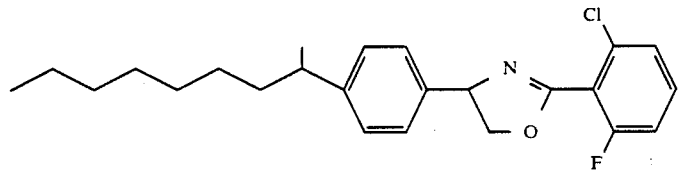 1.5399
32 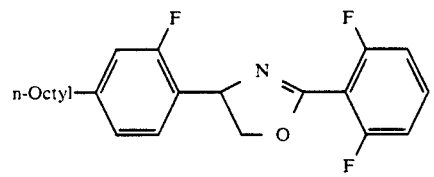 1.5215
33 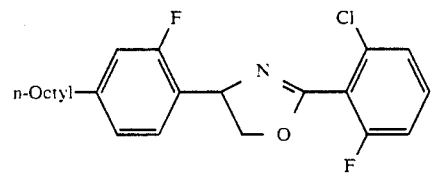 1.5322
34 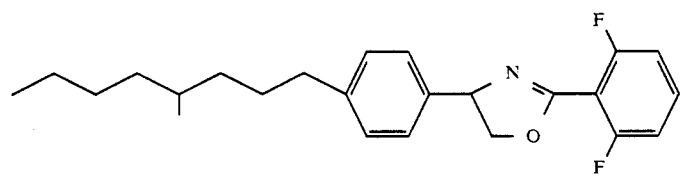 1.5298
35 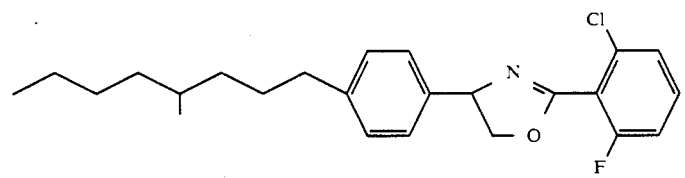 1.5398
36 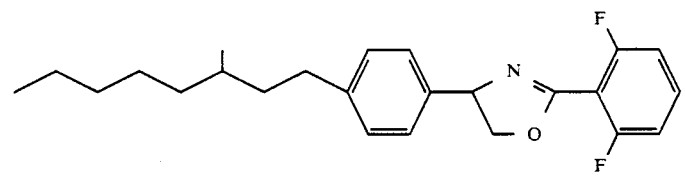 1.5278
37 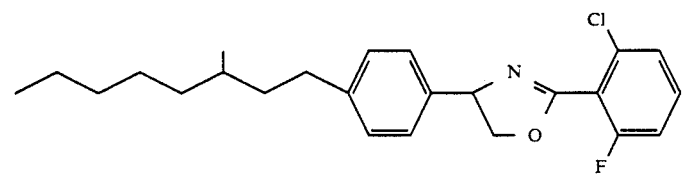 1.5375
38 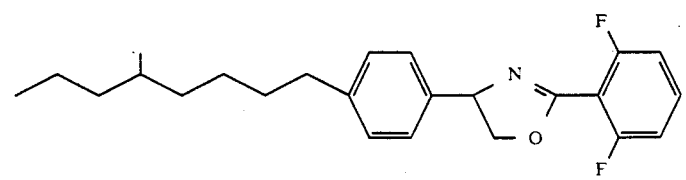 1.5254

-continued
| | | |
|---|---|---|
| 39 | 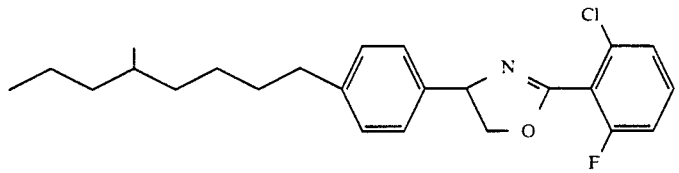 | 1.5380 |
| 40 | 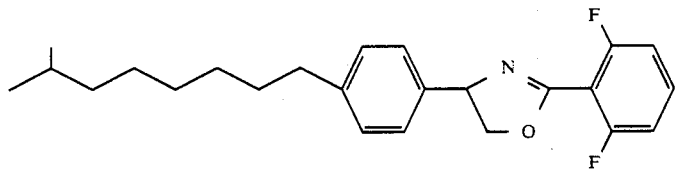 | 1.5326 |
| 41 | 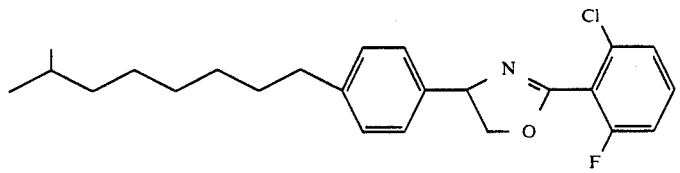 | 1.5369 |
| 42 | 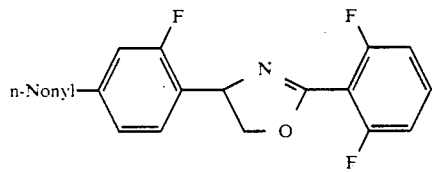 | 1.5184 |
| 43 | 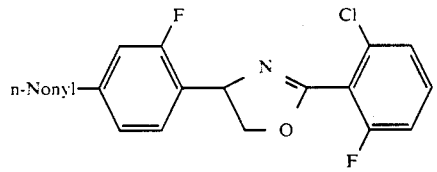 | 1.5286 |
| 44 | 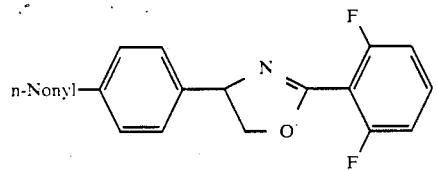 | 1.5274 |
| 45 | 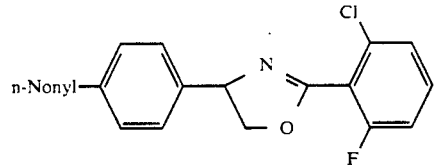 | 1.5376 |
| 46 | 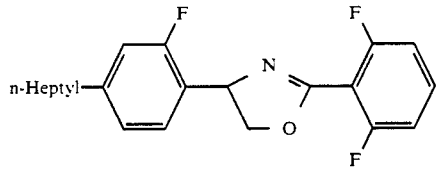 | 1.5236 |
| 47 | 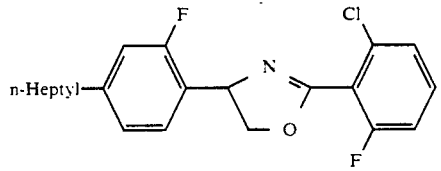 | 1.5270 |

-continued
| | | |
|---|---|---|
| 48 | 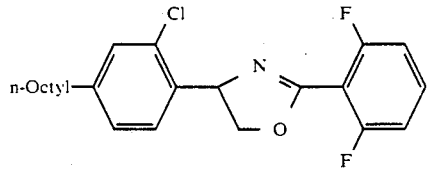 | 1.5372 |
| 49 | 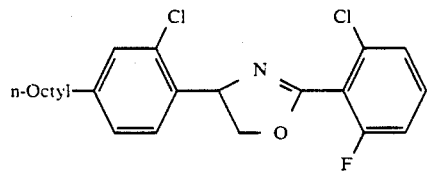 | 1.5452 |
| 50 | 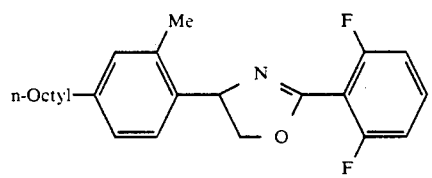 | 1.5349 |
| 51 | 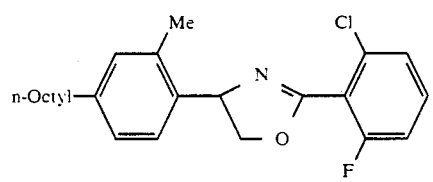 | 1.5443 |
| 52 | 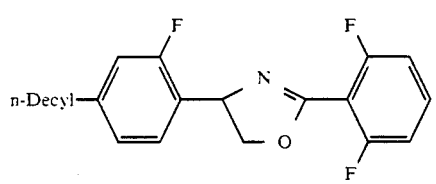 | 1.5154 |
| 53 | 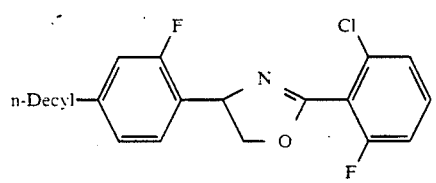 | 1.5255 |
| 54 | 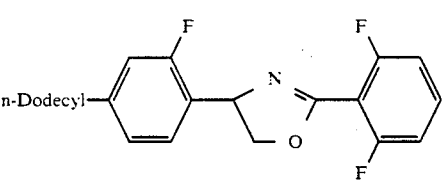 | 1.5106 |
| 55 | 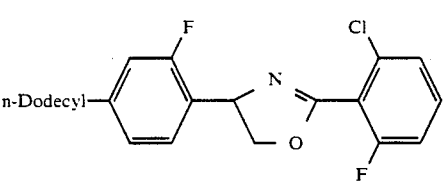 | 1.5200 |
| 56 | 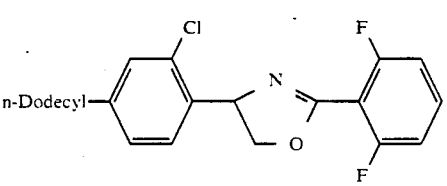 | 1.5236 |

-continued
| | | |
|---|---|---|
| 57 | 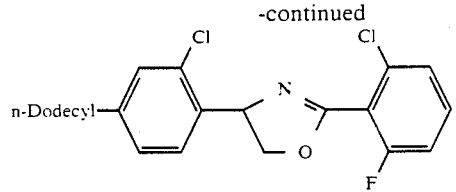 | 1.5270 |
| 58 | 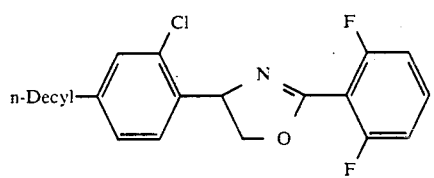 | 1.5194 |
| 59 | 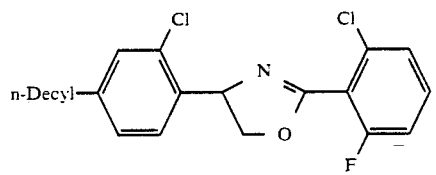 | 1.5326 |
| 60 | 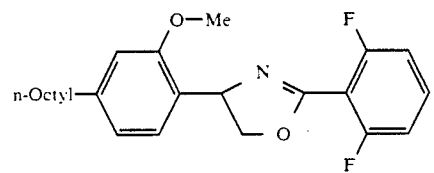 | 1.5356 |
| 61 | 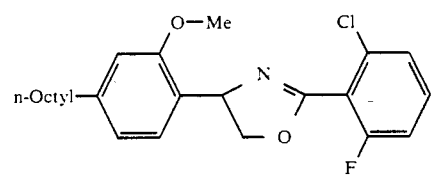 | 1.5410 |
| 62 | 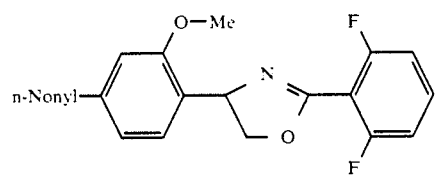 | 1.5329 |
| 63 | 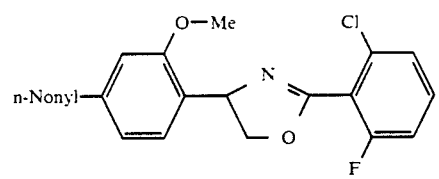 | 1.5418 |
| 64 | 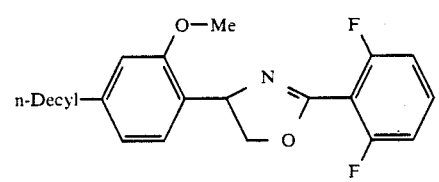 | 1.5262 |
| 65 | 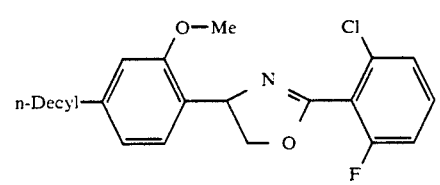 | 1.5365 |

-continued
| | | |
|---|---|---|
| 66 | 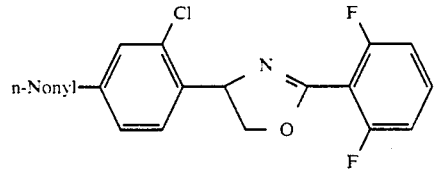 | 1.5283 |
| 67 | 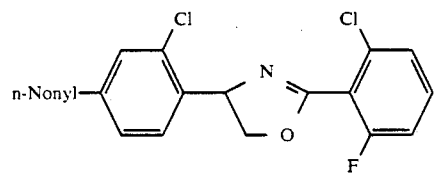 | 1.5373 |
| 68 | 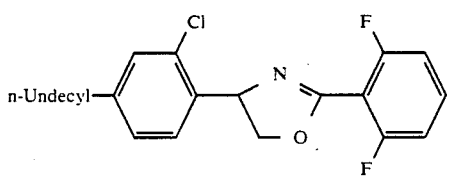 | 1.5334 |
| 69 | 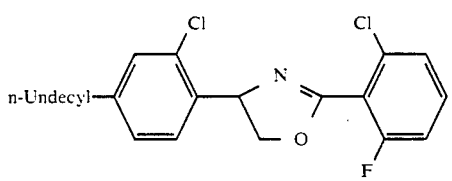 | 1.5408 |
| 70 | 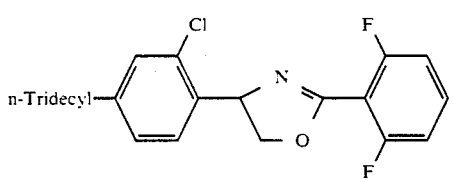 | 1.5253 |
| 71 | 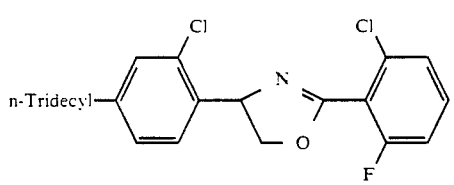 | 1.5324 |
| 72 | 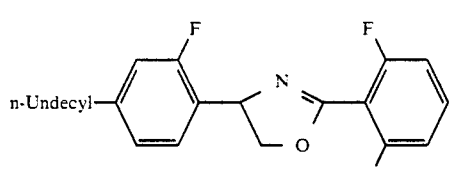 | 1.5150 |
| 73 | 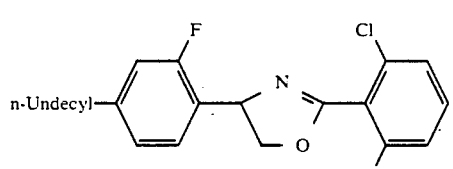 | 1.5246 |
| 74 | 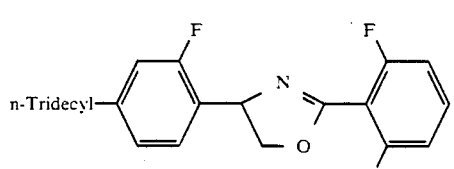 | 1.5120 |

-continued

| # | Structure | Value |
|---|---|---|
| 75 | n-Tridecyl, 2-F phenyl / 2-Cl, 6-F benzoyl oxazoline | 1.5202 |
| 76 | n-Decyl, F phenyl / 2,6-diF benzoyl oxazoline | 1.5242 |
| 77 | n-Heptyl, 2-Cl phenyl / 2,6-diF benzoyl oxazoline | 1.5406 |
| 78 | n-Heptyl, 2-Cl phenyl / 2-Cl, 6-F benzoyl oxazoline | 1.5503 |
| 79 | t-Octyl, 2-OMe phenyl / 2-Cl, 6-F benzoyl oxazoline | 1.5457 |
| 80 | t-Octyl, 2-OMe phenyl / 2,6-diF benzoyl oxazoline | 1.5358 |
| 81 | n-Nonyl, 2-OEt phenyl / 2,6-diF benzoyl oxazoline | 1.5252 |
| 82 | n-Nonyl, 2-OEt phenyl / 2-Cl, 6-F benzoyl oxazoline | 1.5332 |
| 83 | n-Octyl phenyl-CH₂ / 2,6-diF benzoyl oxazoline | 1.5260 |

-continued
| | | |
|---|---|---|
| 84 | 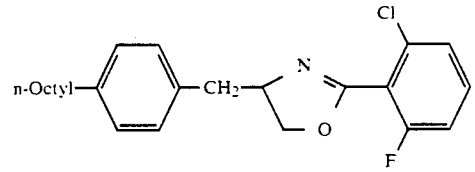 | 1.5355 |
| 85 | 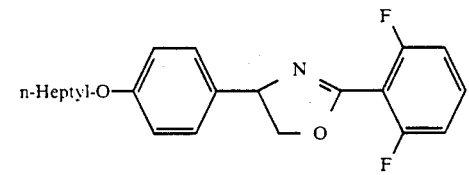 | 1.5314 |
| 86 | 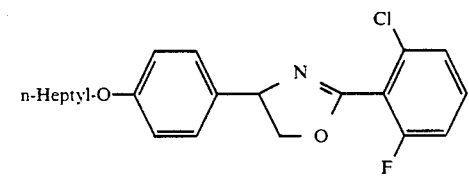 | 1.5419 |
| 87 | 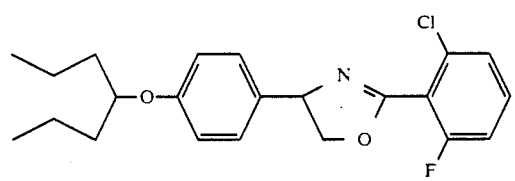 | 1.5401 |
| 88 | 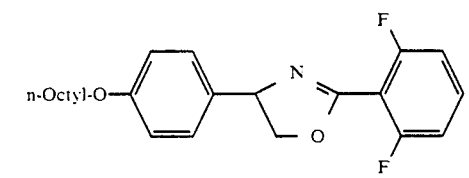 | 1.5284 |
| 89 | 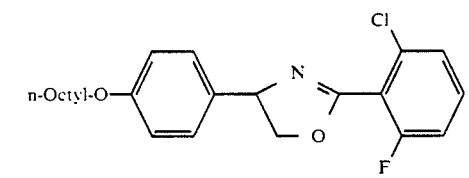 | 1.5389 |
| 90 | 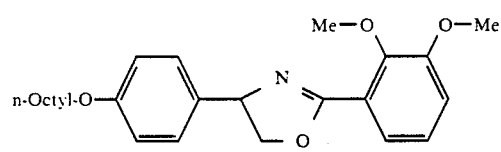 | Amorphous |
| 91 | 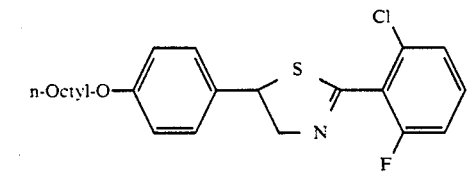 | 41~41.5* |
| 92 | 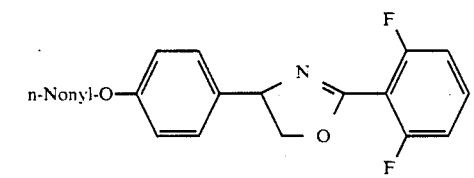 | 1.5269 |

-continued
| | | |
|---|---|---|
| 93 | 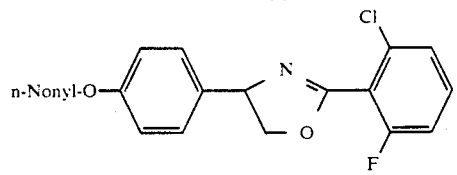 | 1.5372 |
| 94 | 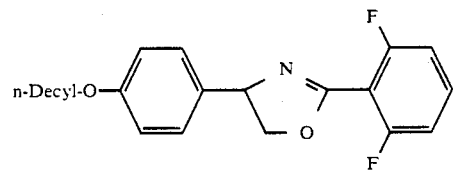 | 1.5236 |
| 95 | 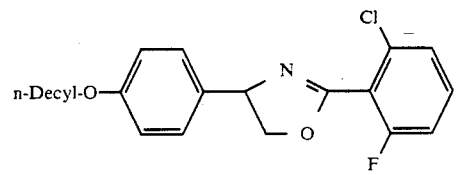 | 1.5118 |
| 96 | 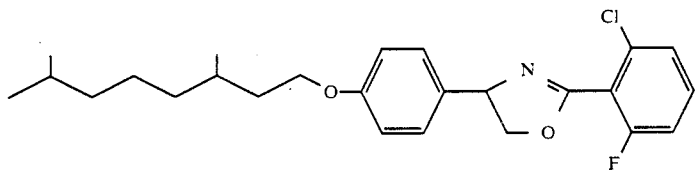 | 1.5377 |
| 97 | 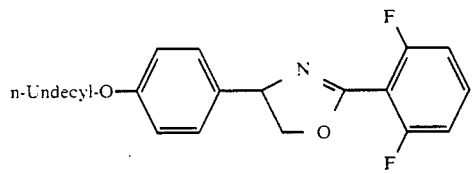 | 1.5254 |
| 98 | 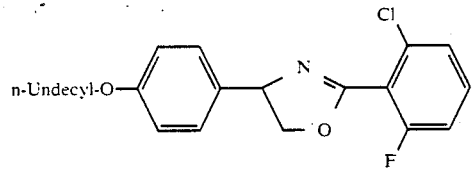 | 1.5310 |
| 99 | 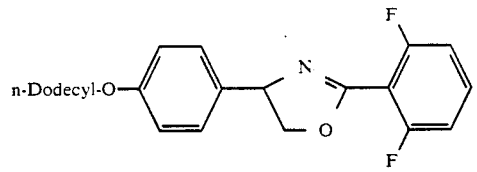 | 1.5215 |
| 100 | 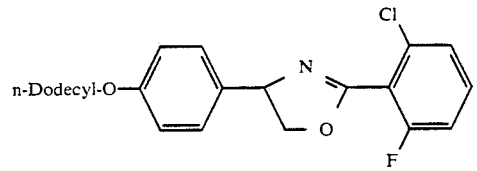 | 1.5268 |
| 101 | 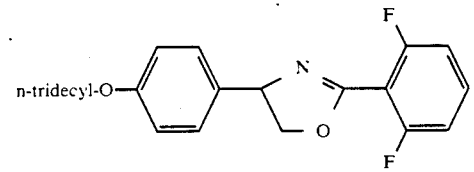 | 43~45* |

-continued
| | | |
|---|---|---|
| 102 | 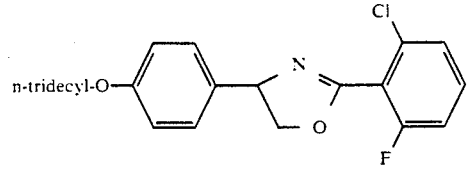 | 1.5246 |
| 103 | 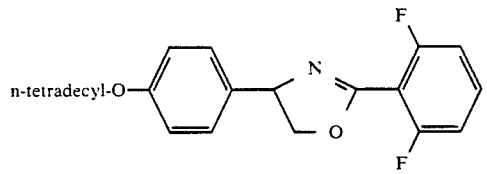 | 42.5~45* |
| 104 | 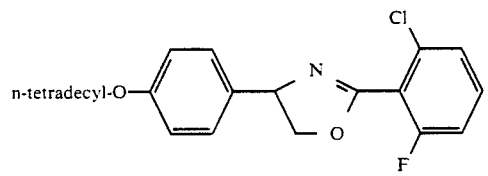 | 1.5233 |
| 105 | 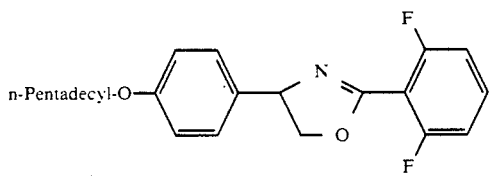 | 53.5~55* |
| 106 | 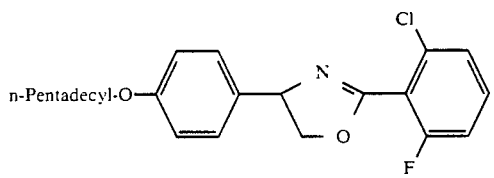 | 56~58* |
| 107 | 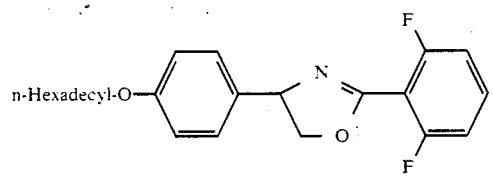 | 66~70* |
| 108 | 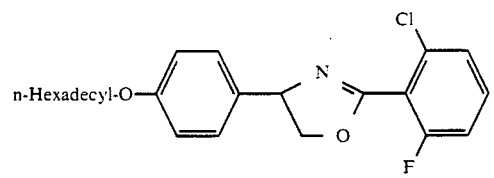 | 55.5~58* |
| 109 | 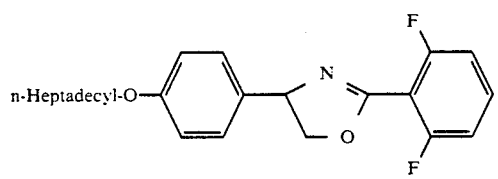 | 59~60.5* |
| 110 | 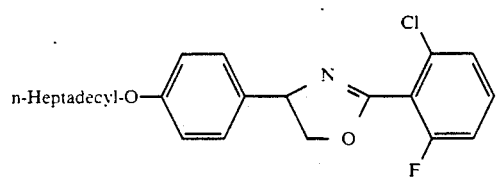 | 68~69* |

-continued
| | | |
|---|---|---|
| 111 | 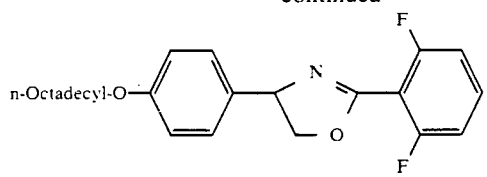 | 74~75* |
| 112 | 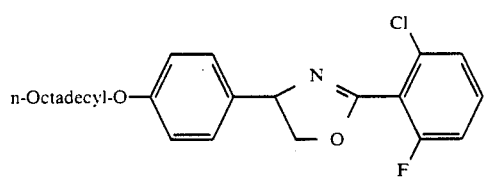 | 67~68.5* |
| 113 | 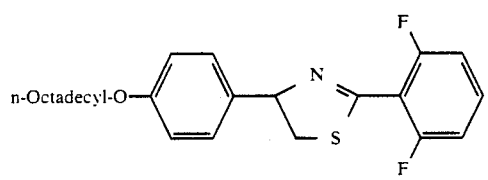 | 57.5~61* |
| 114 | 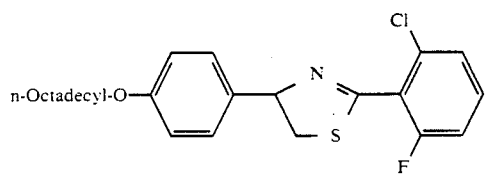 | 69.5~70* |
| 115 | 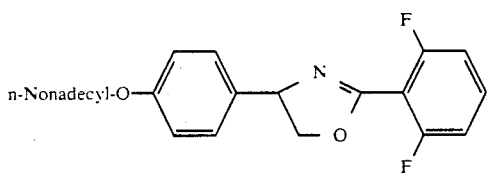 | 61~61.5* |
| 116 | 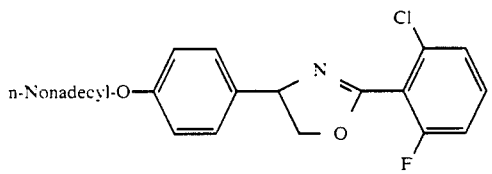 | 64.5~66* |
| 117 | 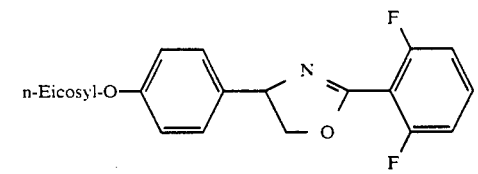 | 38.5~39* |
| 118 | 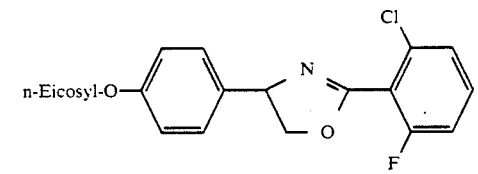 | 40~41* |
| 119 | 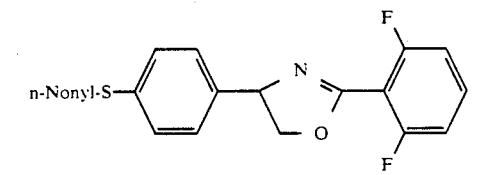 | 1.5512 |

-continued
| | | |
|---|---|---|
| 120 | 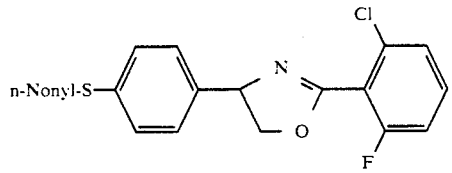 | 1.5599 |
| 121 | 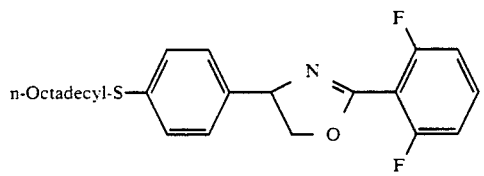 | 74.5~75* |
| 122 | 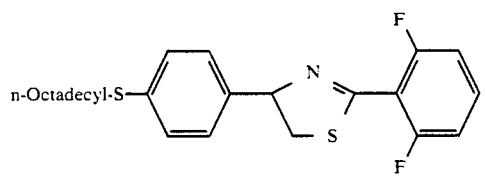 | 66~67* |
| 123 | 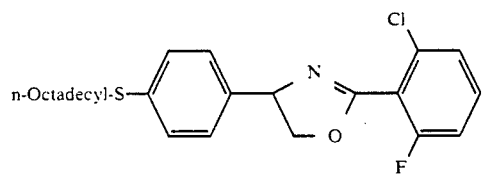 | 63~64.5* |
| 124 | 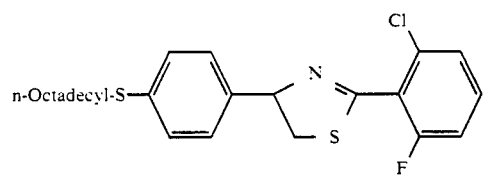 | 67~71* |
| 125 | 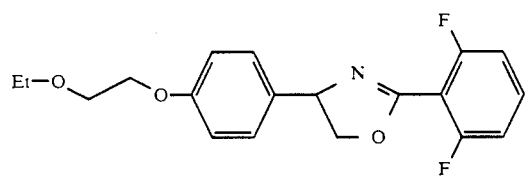 | 1.5412 |
| 126 | 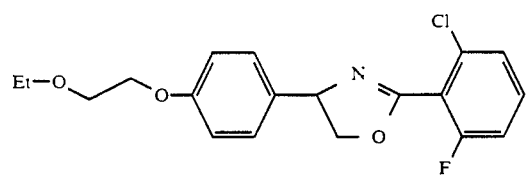 | 1.5521 |
| 127 | 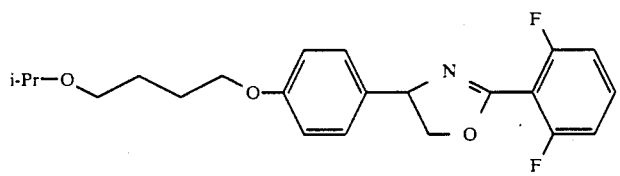 | 1.5310 |
| 128 | 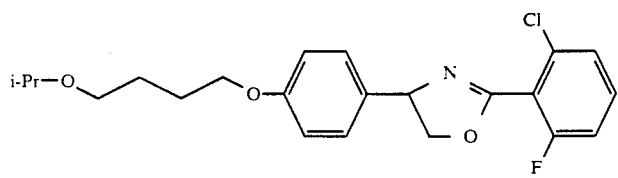 | 1.5408 |

-continued
| | | |
|---|---|---|
| 129 | 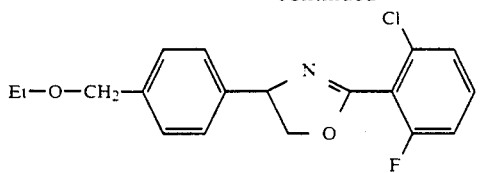 | 1.5604 |
| 130 | 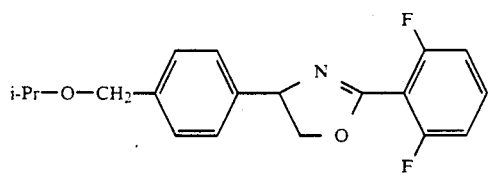 | 1.5340 |
| 131 | 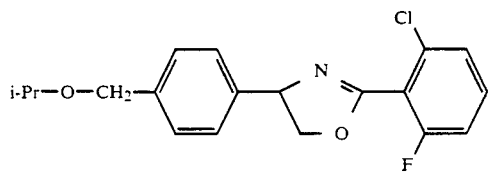 | 1.5458 |
| 132 | 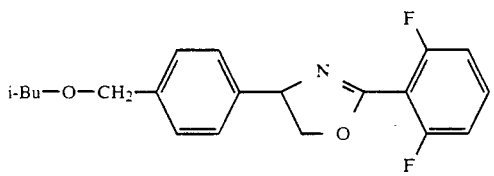 | 1.5372 |
| 133 | 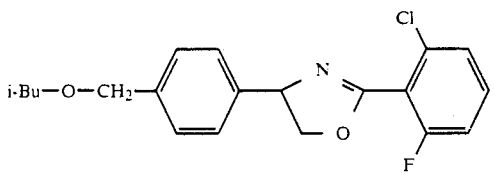 | 1.5465 |
| 134 | 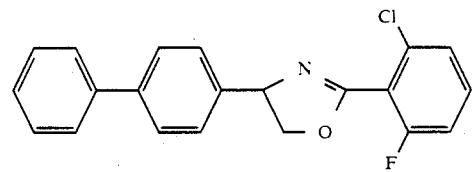 | 88~92* |
| 135 | 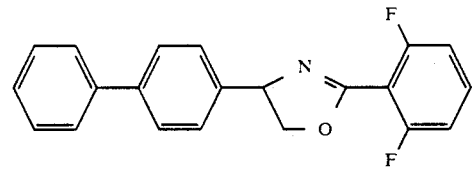 | 98~101* |
| 136 | 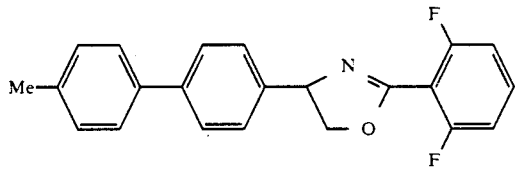 | 123~127* |
| 137 | 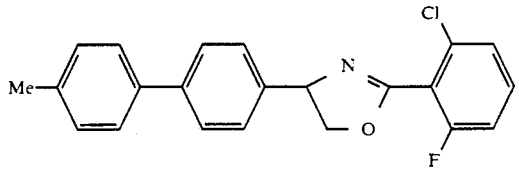 | 110~113* |

-continued
| | | |
|---|---|---|
| 138 | 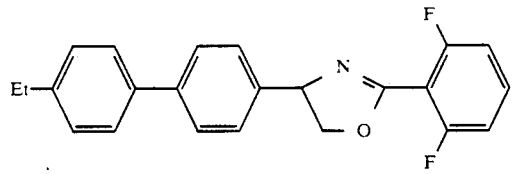 | 130~132* |
| 139 | 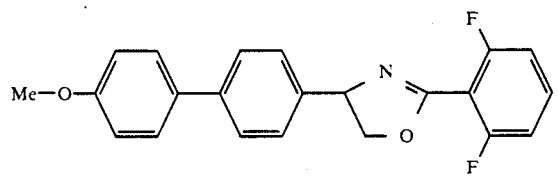 | 120~125* |
| 140 | 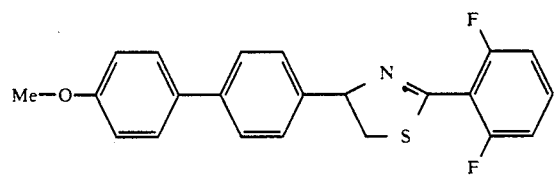 | 92~92.5* |
| 141 | 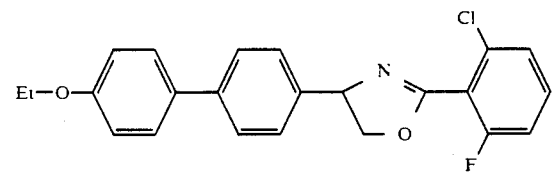 | 93~95* |
| 142 | 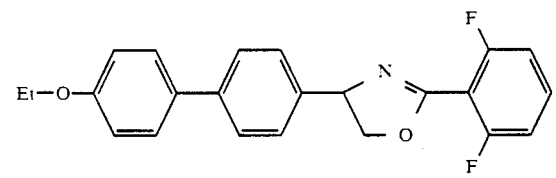 | 95~99.5* |
| 143 | 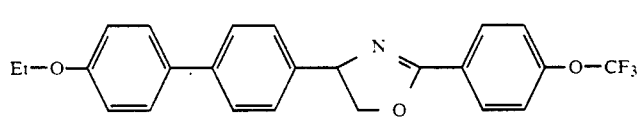 | 79~84* |
| 144 | 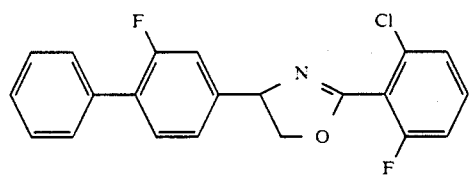 | 103~104* |
| 145 | 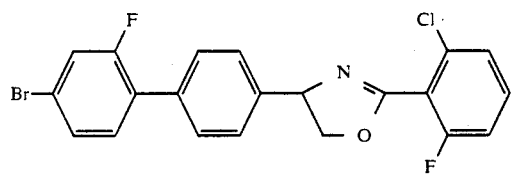 | 1.6117 |
| 146 | 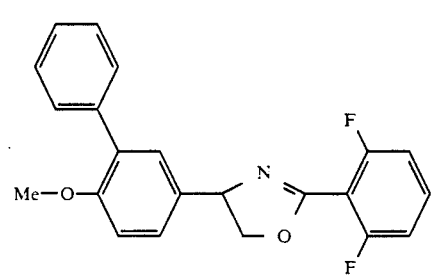 | 93.5~95* |

| | | |
|---|---|---|
| 147 | 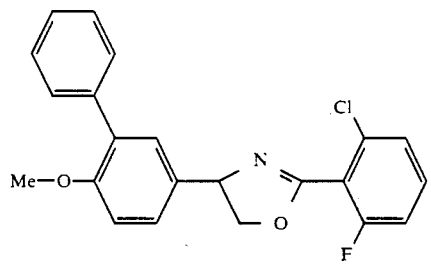 | 80.5~82* |
| 148 | 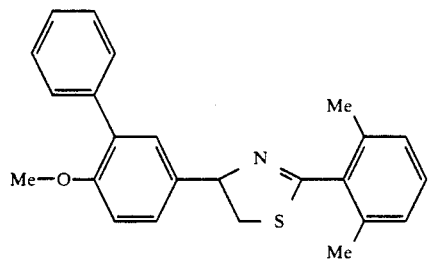 | 71.5~73* |
| 149 | 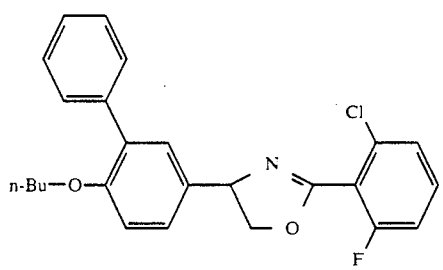 | 1.5873 |
| 150 | 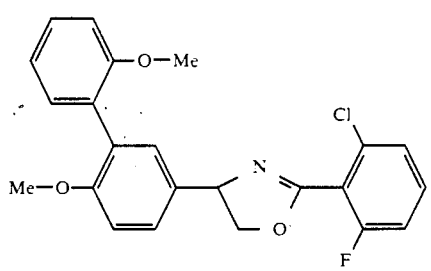 | 47~50* |
| 151 | 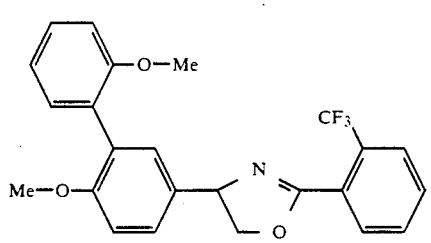 | 39~43* |
| 152 | 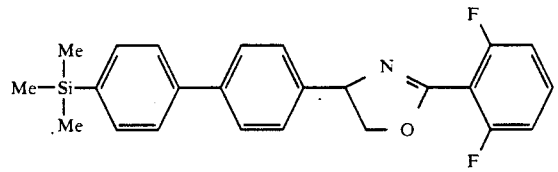 | 1.5842 |

-continued
| | | |
|---|---|---|
| 153 | 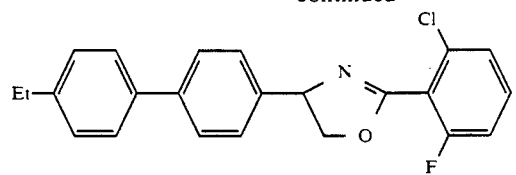 | 125~126* |
| 154 | 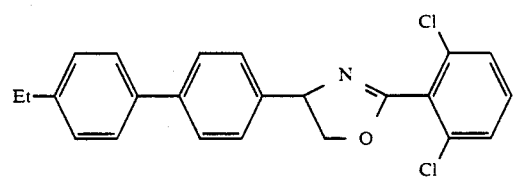 | 171~173* |
| 155 | 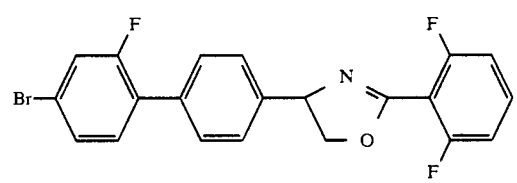 | 1.5998 |
| 156 | 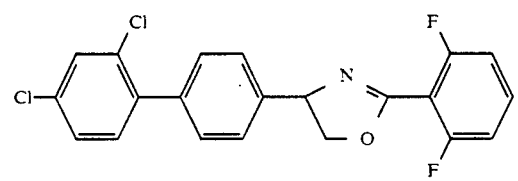 | 1.6146 |
| 157 | 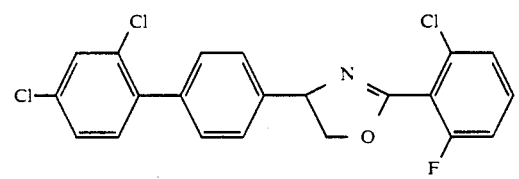 | 1.6279 |
| 158 | 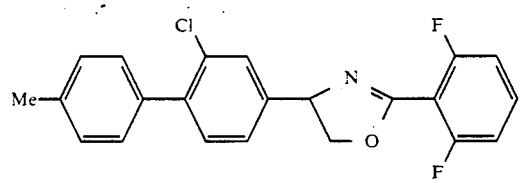 | 85.5~87* |
| 159 | 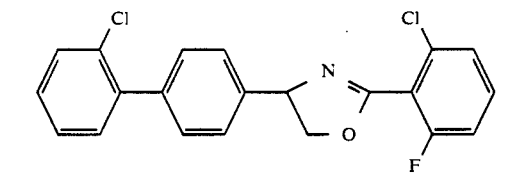 | 1.6200 |
| 160 | 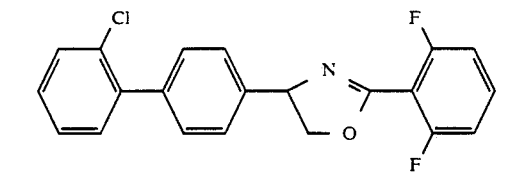 | 1.6100 |
| 161 | 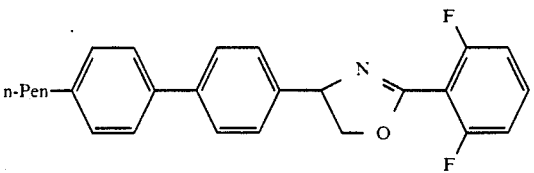 | 60~62* |

-continued

| No. | Structure | m.p. (°C) |
|---|---|---|
| 162 | n-Pen–C₆H₄–C₆H₄–CH(CH₂O–)N=C(2-Cl,6-F-C₆H₃) | 56~58* |
| 163 | n-Octyl–C₆H₄–C₆H₄–CH(CH₂O–)N=C(2,6-F₂-C₆H₃) | 65~67.5* |
| 164 | n-Octyl–C₆H₄–C₆H₄–CH(CH₂O–)N=C(2-Cl,6-F-C₆H₃) | 62.5~64* |
| 165 | Cl–C₆H₄–C₆H₄–CH(CH₂O–)N=C(2,6-F₂-C₆H₃) | 160~161* |
| 166 | Cl–C₆H₄–C₆H₄–CH(CH₂O–)N=C(2-Cl,6-F-C₆H₃) | 132~133* |
| 167 | n-Pr–C₆H₄–C₆H₄–CH(CH₂O–)N=C(2,6-F₂-C₆H₃) | 116~117* |
| 168 | n-Pr–C₆H₄–C₆H₄–CH(CH₂O–)N=C(2-Cl,6-F-C₆H₃) | 107~109* |
| 169 | Br–C₆H₄–C₆H₄–CH(CH₂O–)N=C(2-Cl,6-F-C₆H₃) | 101~102* |
| 170 | Br–C₆H₄–C₆H₄–CH(CH₂O–)N=C(2,6-F₂-C₆H₃) | 127~129* |

-continued
| | | |
|---|---|---|
| 171 | 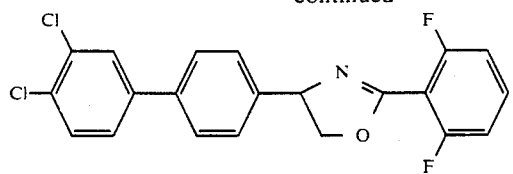 | 114~115* |
| 172 | 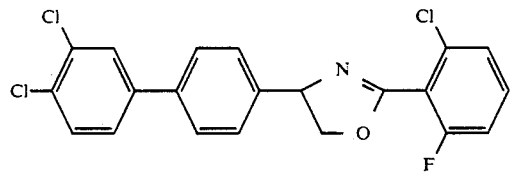 | 112~115* |
| 173 | 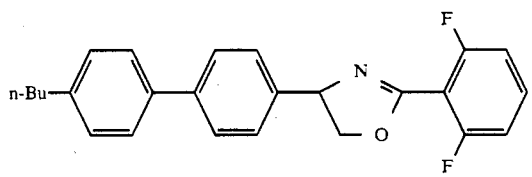 | 95~96* |
| 174 | 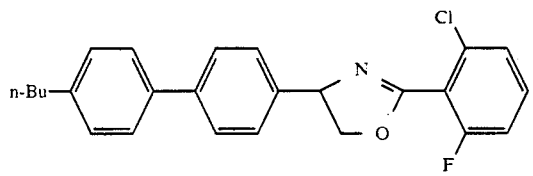 | 87~87.5* |
| 175 | 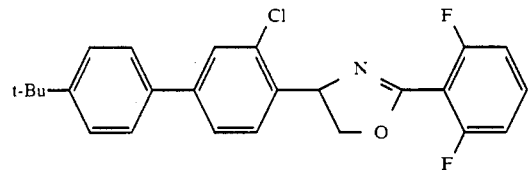 | 1.5900 |
| 176 | 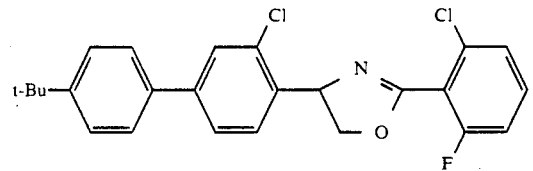 | 1.5958 |
| 177 | 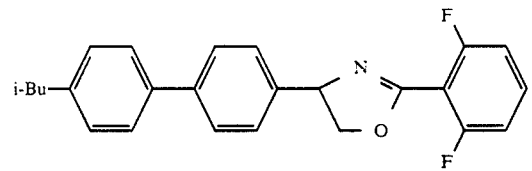 | 106~107* |
| 178 | 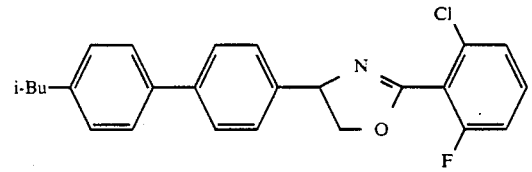 | 87~88* |
| 179 | 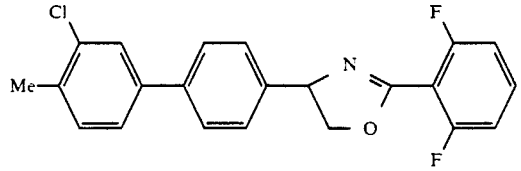 | 101~102* |

-continued
| | | |
|---|---|---|
| 180 | 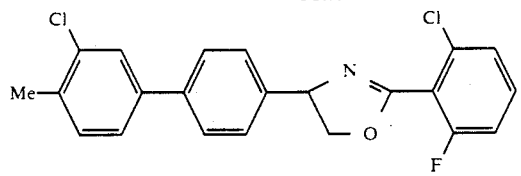 | 76.5~78* |
| 181 | 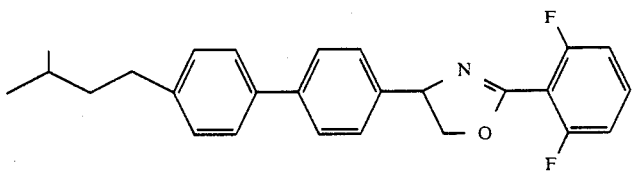 | 79~80* |
| 182 | 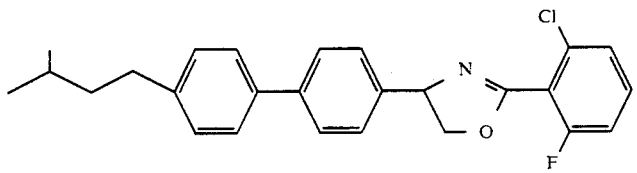 | 52.5~53.5* |
| 183 | 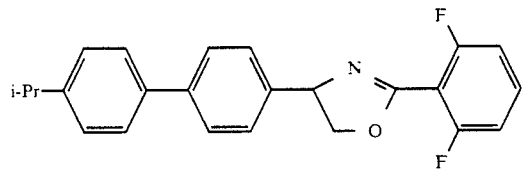 | 1.5124 |
| 184 | 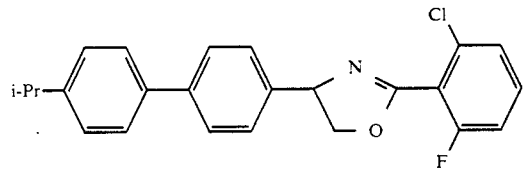 | 1.6072 |
| 185 | 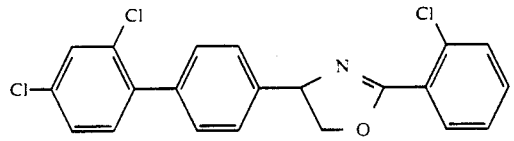 | 1.6468 |
| 186 | 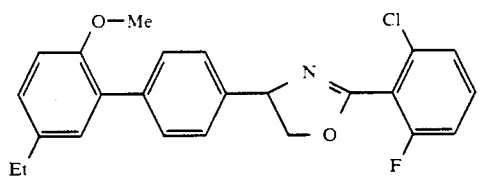 | 52~54* |
| 187 | 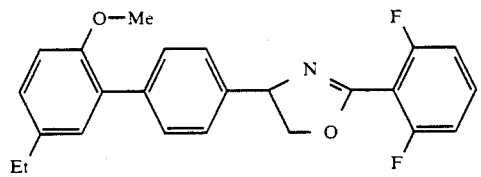 | Amorphous |
| 188 | 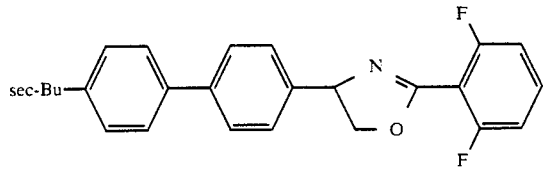 | 1.5939 |

-continued

| No. | Structure | Value |
|---|---|---|
| 189 | sec-Bu-biphenyl-CH(CH2O-)N=C(Cl,F-phenyl) | 1.6013 |
| 190 | t-Bu-biphenyl-CH(CH2O-)N=C(2,6-F2-phenyl) | 112~113.5* |
| 191 | t-Bu-biphenyl-CH(CH2O-)N=C(Cl,F-phenyl) | 123~124* |
| 192 | 3-Cl-biphenyl-CH(CH2O-)N=C(2,6-F2-phenyl) | 66.5~67.5* |
| 193 | 3-Cl-biphenyl-CH(CH2O-)N=C(Cl,F-phenyl) | 1.6272 |
| 194 | Et-(3-F-biphenyl)-CH(CH2O-)N=C(2,6-F2-phenyl) | 99.5~100* |
| 195 | Et-(3-F-biphenyl)-CH(CH2O-)N=C(Cl,F-phenyl) | 90~91.5* |
| 196 | 2,4-F2-biphenyl-CH(CH2O-)N=C(2,6-F2-phenyl) | 1.5886 |
| 197 | 2,4-F2-biphenyl-CH(CH2O-)N=C(Cl,F-phenyl) | 1.5988 |

-continued
| | | |
|---|---|---|
| 198 | 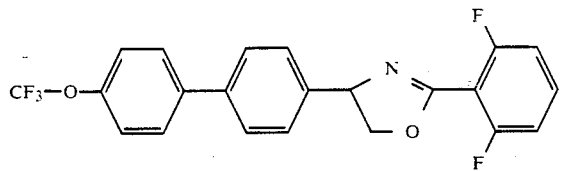 | 1.5900 |
| 199 | 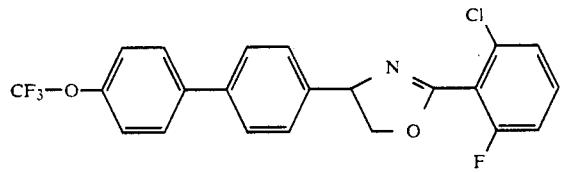 | 1.5990 |
| 200 | 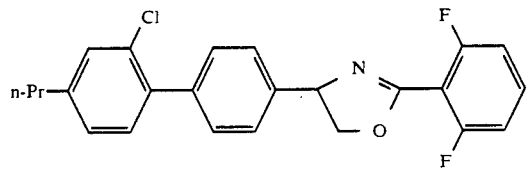 | 1.5968 |
| 201 | 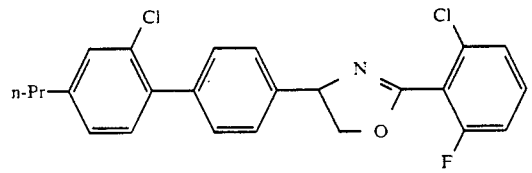 | 1.6060 |
| 202 | 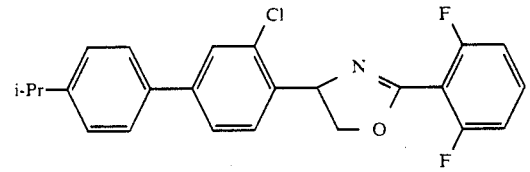 | 1.6017 |
| 203 | 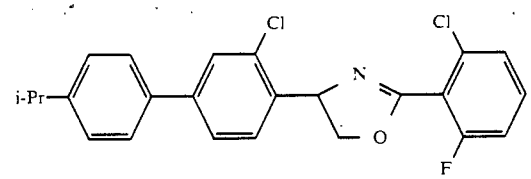 | 1.6086 |
| 204 | 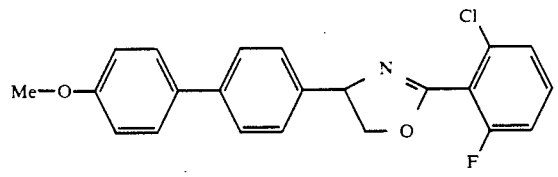 | 1.6170 |
| 205 | 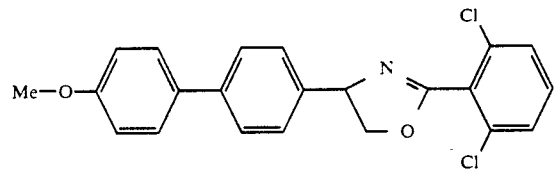 | 112~114* |
| 206 | 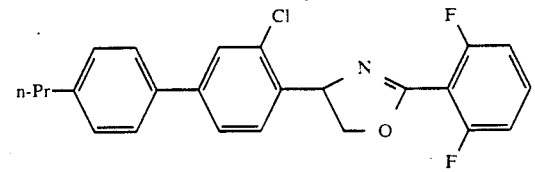 | 1.6005 |

-continued
| | | |
|---|---|---|
| 207 | 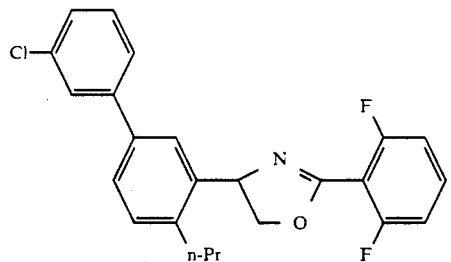 | 1.5893 |
| 208 | 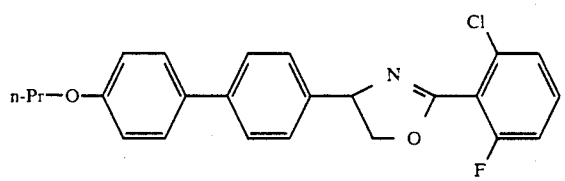 | 1.6056 |
| 209 | 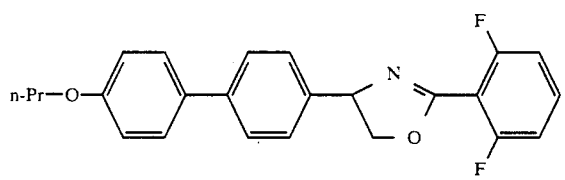 | 1.5971 |
| 210 | 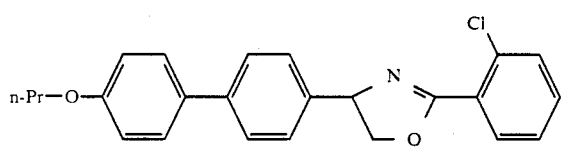 | 1.6216 |
| 211 | 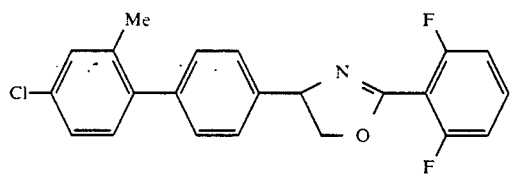 | 1.6059 |
| 212 | 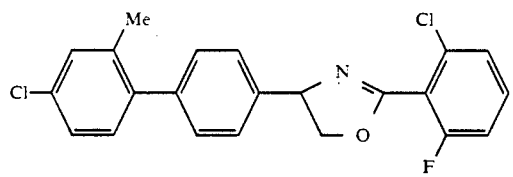 | 1.6146 |
| 213 | 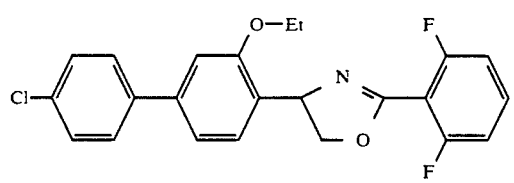 | 1.6040 |
| 214 | 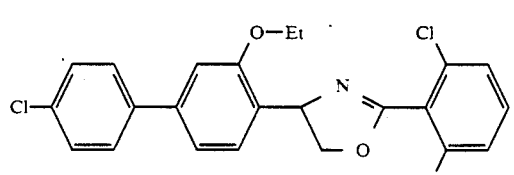 | 102~103* |

-continued
| | | |
|---|---|---|
| 215 | 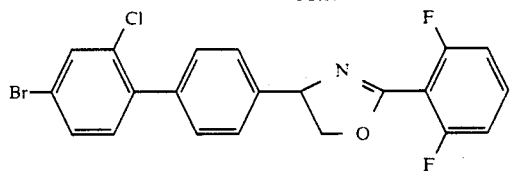 | 1.6140 |
| 216 | 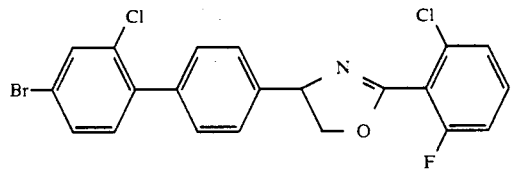 | 1.6220 |
| 217 | 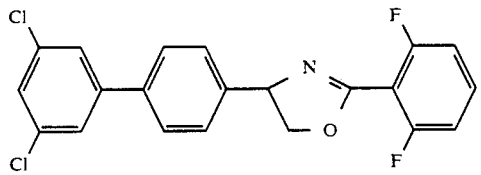 | 1.6225 |
| 218 | 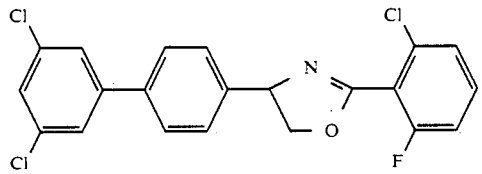 | 1.6318 |
| 219 | 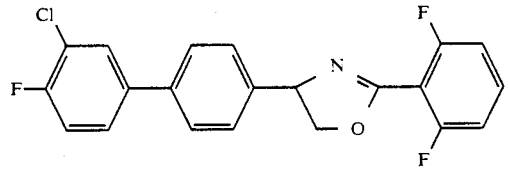 | 98.5~101* |
| 220 | 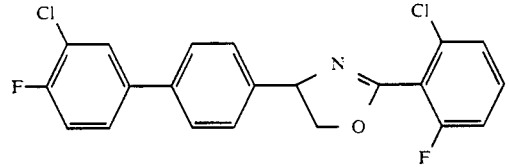 | 120~121* |
| 221 | 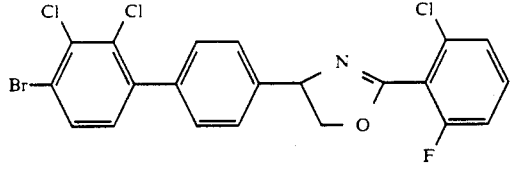 | 1.6252 |
| 222 | 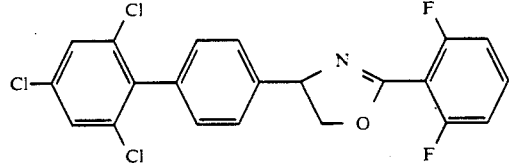 | 54~60* |
| 223 | 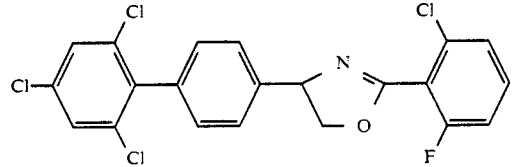 | 1.6237 |

-continued
| | | |
|---|---|---|
| 224 | 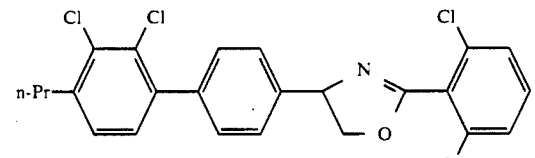 | 1.5998 |
| 225 | 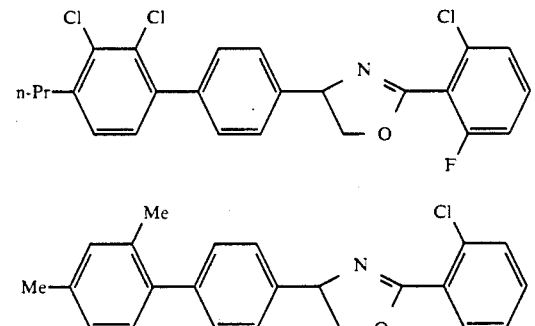 | 1.6108 |
| 226 | 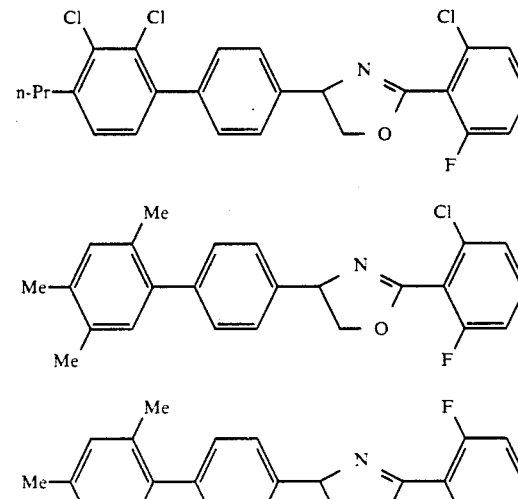 | 1.6004 |
| 227 | 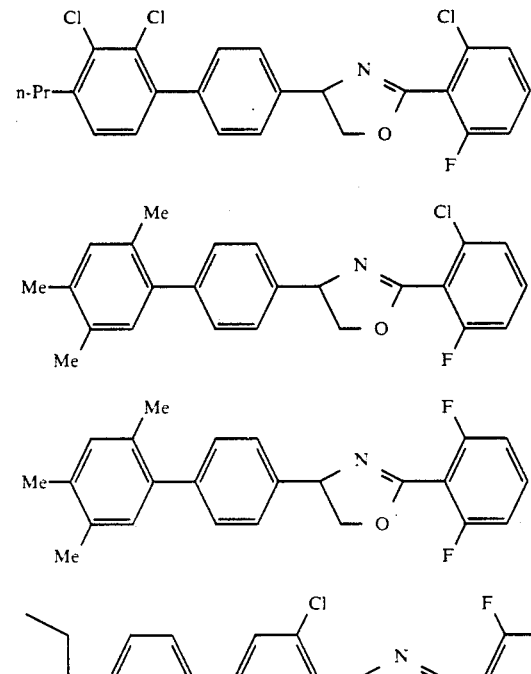 | 1.5935 |
| 228 | 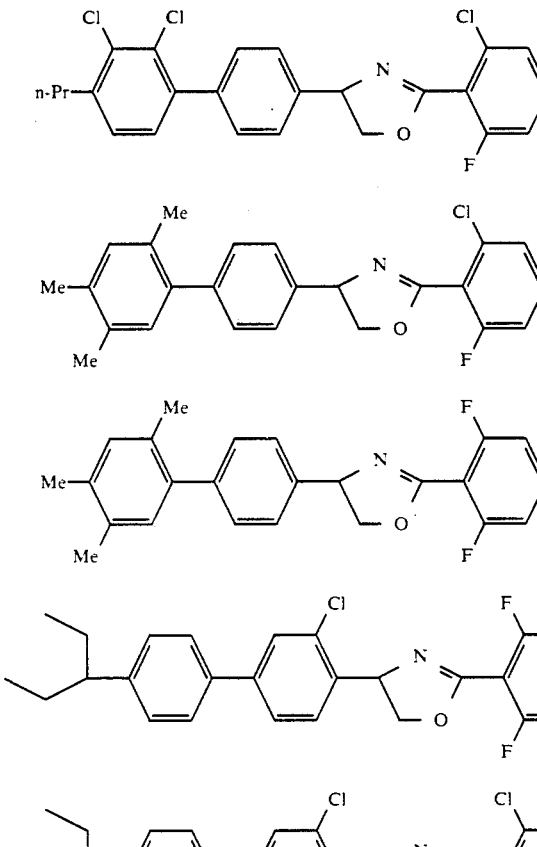 | 1.5838 |
| 229 | 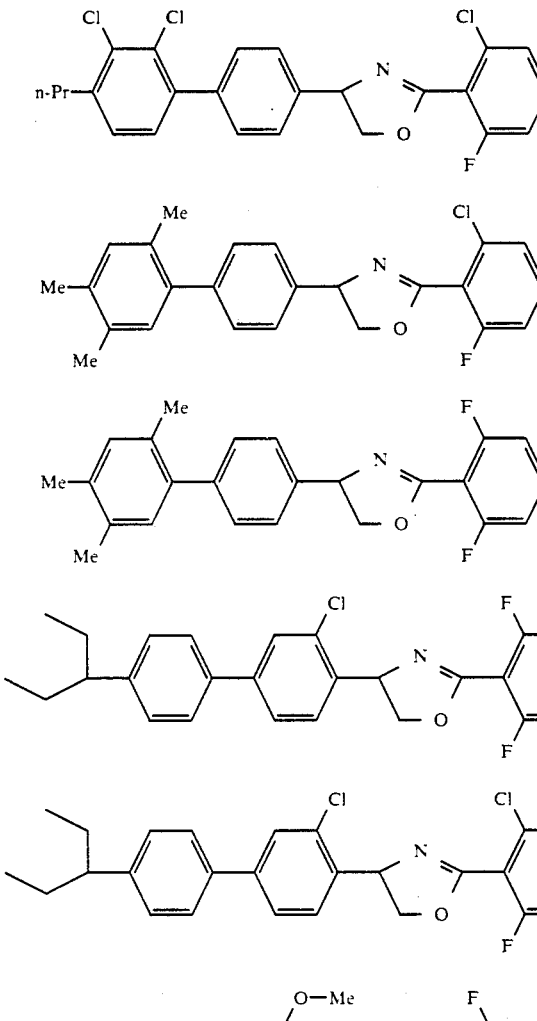 | 1.5913 |
| 230 | 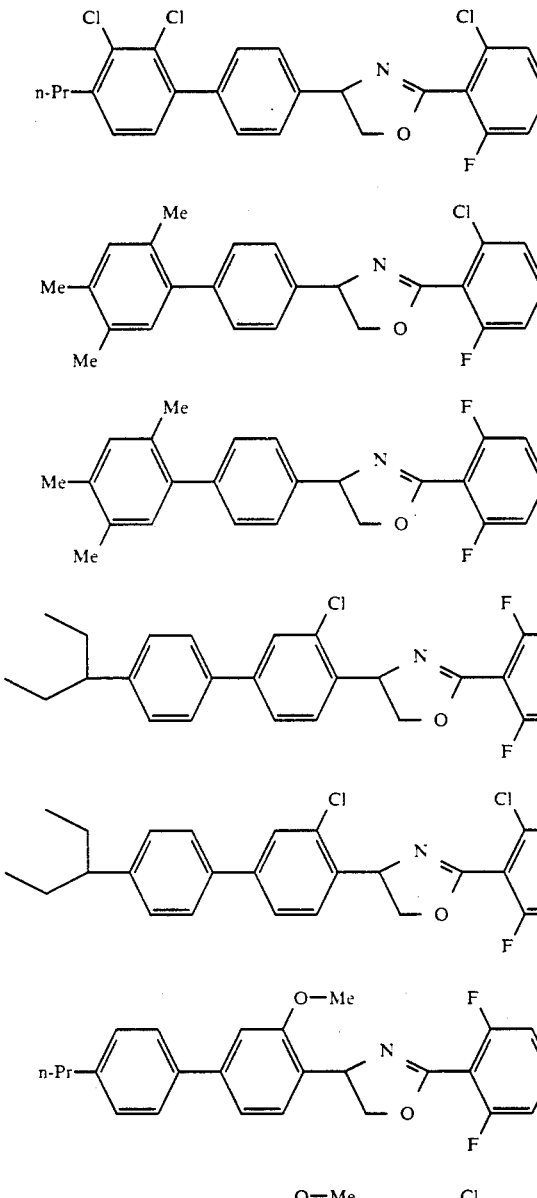 | 1.5852 |
| 231 | 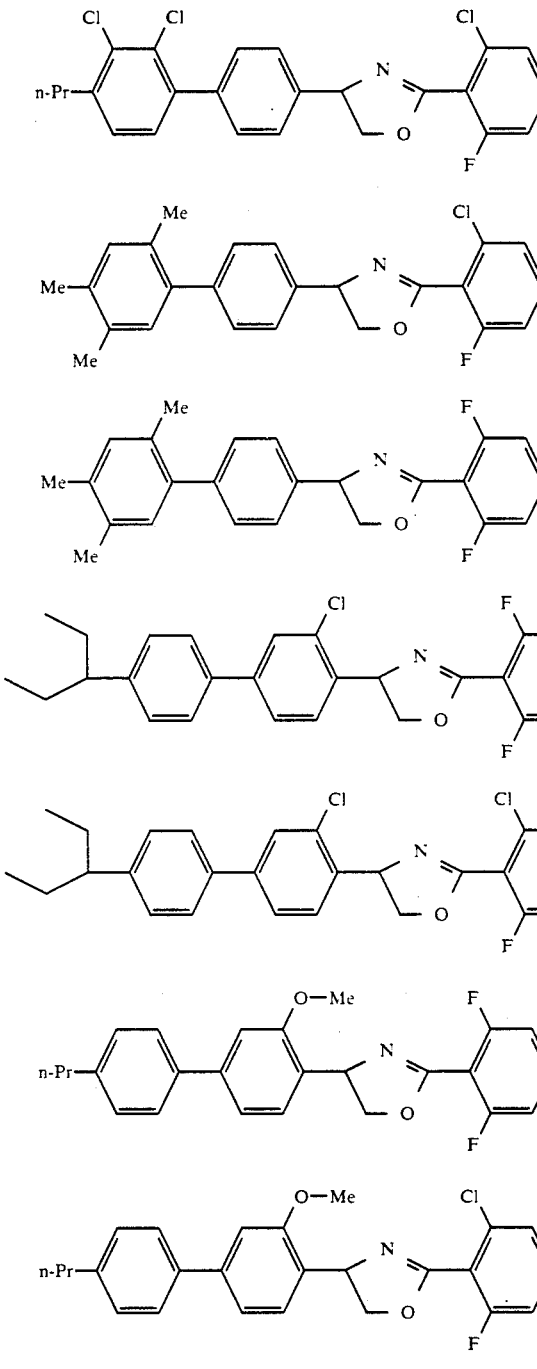 | 1.5928 |
| 232 | | 1.5771 |

-continued
| 233 | 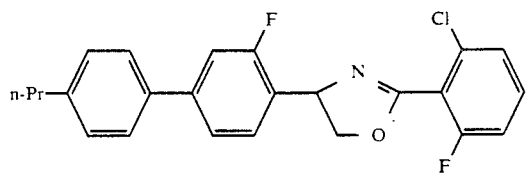 | 1.5856 |
| 234 | 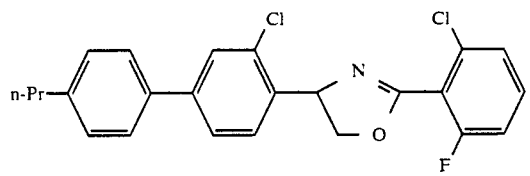 | 1.6098 |
| 235 | 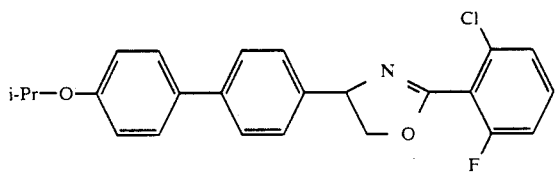 | 1.5980 |
| 236 | 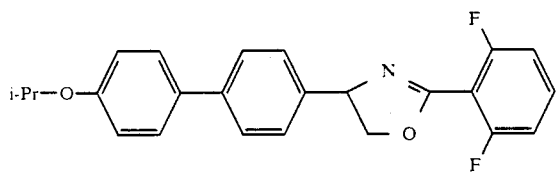 | 1.5898 |
| 237 | 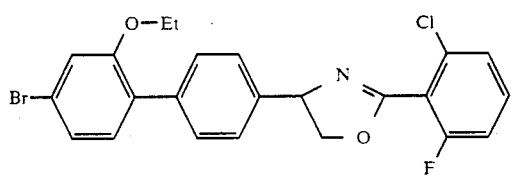 | 1.5832 |
| 238 | 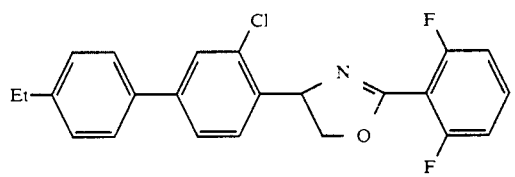 | 1.5978 |
| 239 | 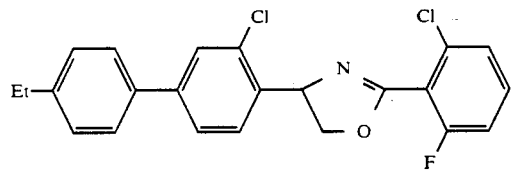 | 1.6158 |
| 240 | 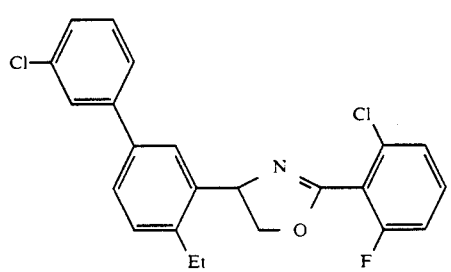 | 1.6066 |

-continued
| | | |
|---|---|---|
| 241 | 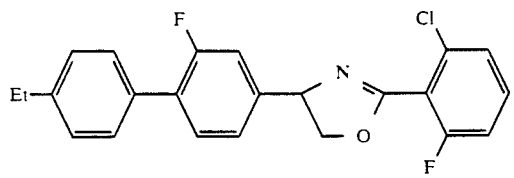 | 1.5895 |
| 242 | 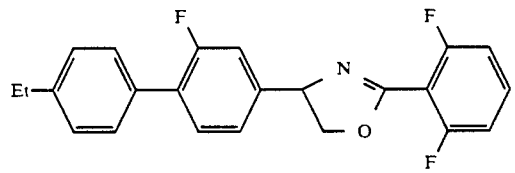 | 1.5815 |
| 243 | 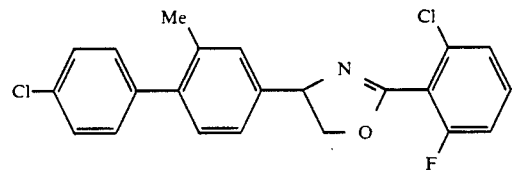 | 1.6018 |
| 244 | 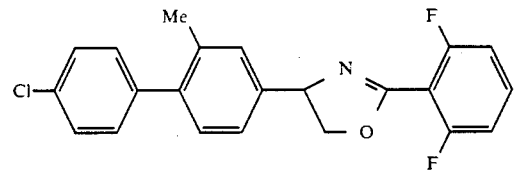 | 1.5902 |
| 245 | 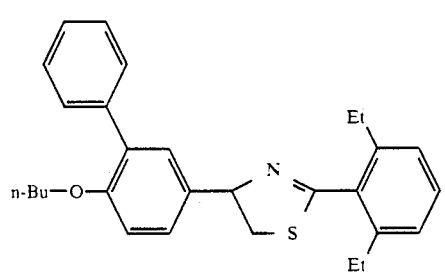 | 1.6094 |
| 246 | 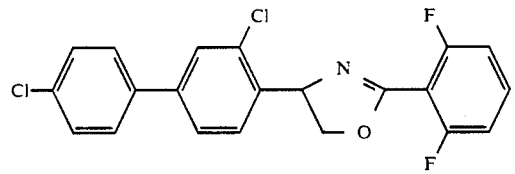 | 1.6229 |
| 247 | 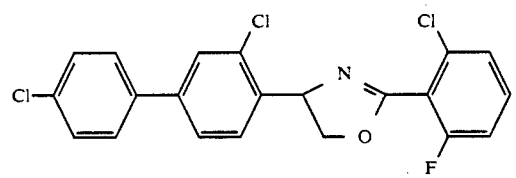 | 1.6290 |
| 248 | 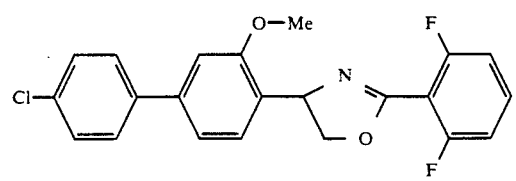 | 1.6072 |

-continued
| | | |
|---|---|---|
| 249 | 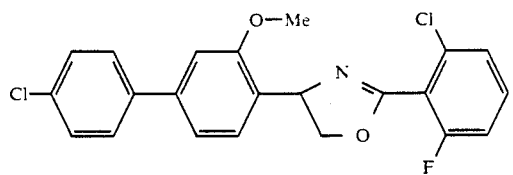 | 1.6140 |
| 250 | 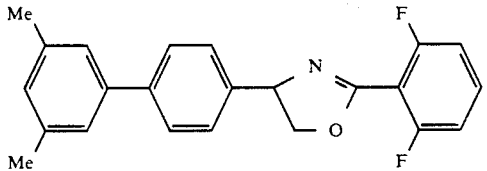 | 1.6072 |
| 251 | 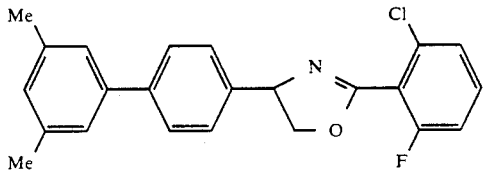 | 1.6165 |
| 252 | 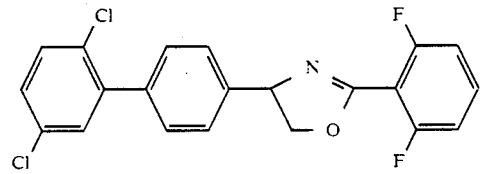 | 1.6102 |
| 253 | 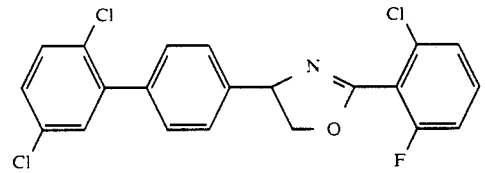 | 1.6222 |
| 254 | 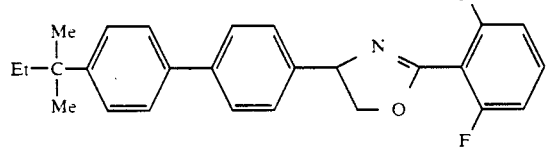 | 94~99* |
| 255 | 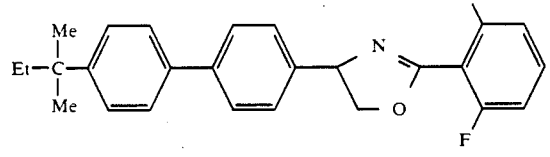 | 84~86* |
| 256 | 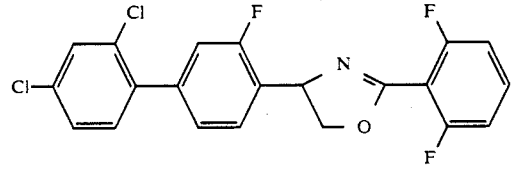 | 1.6062 |
| 257 | 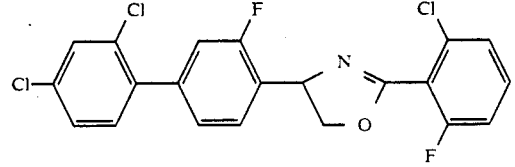 | 1.6101 |

-continued
| | | |
|---|---|---|
| 258 | 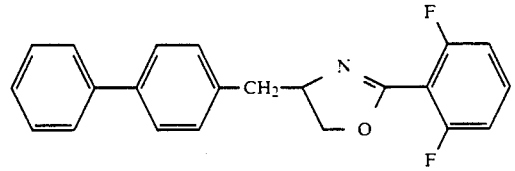 | 1.5918 |
| 259 | 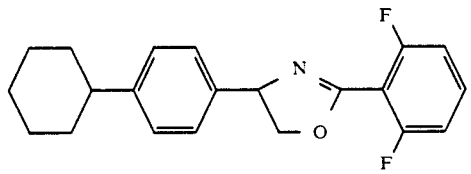 | 1.5586 |
| 260 | 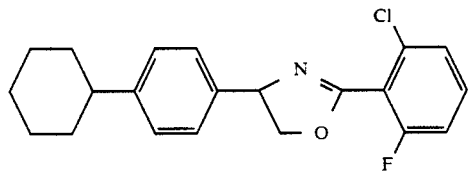 | 1.5640 |
| 261 | 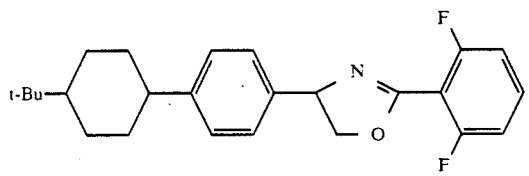 | 1.5428 |
| 262 | 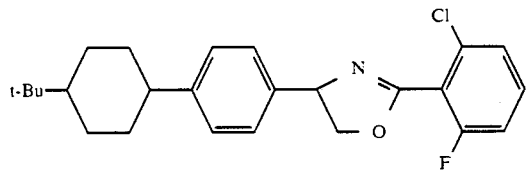 | 1.5486 |
| 263 | 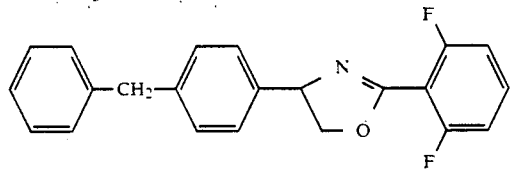 | 1.5898 |
| 264 | 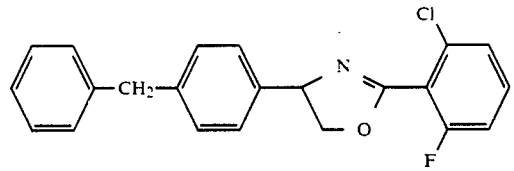 | 1.6004 |
| 265 | 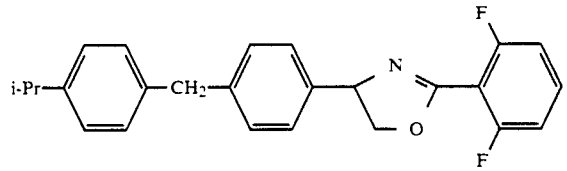 | 1.5824 |
| 266 | 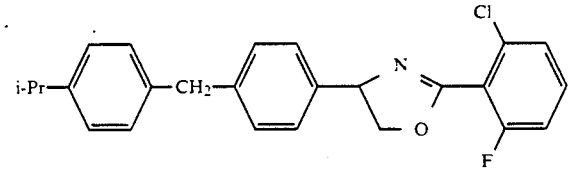 | 1.5956 |

-continued

| # | Structure | Value |
|---|---|---|
| 267 | i-Pr–C₆H₄–CH₂–C₆H₄–CH(–N=C(2-Cl,6-F-C₆H₃))–CH₂–S | Amorphous |
| 268 | i-Pr–C₆H₄–CH₂–C₆H₄–CH(–N=C(2,6-F₂-C₆H₃))–CH₂–S | 97~100* |
| 269 | t-Bu–C₆H₄–CH₂–(2-F-C₆H₃)–CH(–N=C(2,6-F₂-C₆H₃))–CH₂–O | 1.5632 |
| 270 | t-Bu–C₆H₄–CH₂–(2-F-C₆H₃)–CH(–N=C(2-Cl,6-F-C₆H₃))–CH₂–O | 1.5716 |
| 271 | MeO–C₆H₄–CH₂–C₆H₄–CH(–N=C(2,6-F₂-C₆H₃))–CH₂–O | 1.5850 |
| 272 | MeO–C₆H₄–CH₂–C₆H₄–CH(–N=C(2-Cl,6-F-C₆H₃))–CH₂–O | 1.5950 |
| 273 | 4-F-C₆H₄–CH₂–C₆H₄–CH(–N=C(2,6-F₂-C₆H₃))–CH₂–O | 1.5767 |
| 274 | 4-F-C₆H₄–CH₂–C₆H₄–CH(–N=C(2-Cl,6-F-C₆H₃))–CH₂–O | 1.5882 |
| 275 | C₆F₅–CH₂–C₆H₄–CH(–N=C(2,6-F₂-C₆H₃))–CH₂–O | 1.5494 |

-continued

| No. | Structure | Value |
|---|---|---|
| 276 | pentafluorobenzyl-C6H4-CH(CH2O-)N=C-(2-Cl,6-F-C6H3) | 1.5581 |
| 277 | 4-Cl-C6H4-CH2-C6H4-CH(CH2O-)N=C-(2,6-F2-C6H3) | 1.5920 |
| 278 | 4-Cl-C6H4-CH2-C6H4-CH(CH2O-)N=C-(2-Cl,6-F-C6H3) | 1.6017 |
| 279 | 2,4-Cl2-C6H3-CH2-C6H4-CH(CH2O-)N=C-(2,6-F2-C6H3) | 1.5982 |
| 280 | 2,4-Cl2-C6H3-CH2-C6H4-CH(CH2O-)N=C-(2-Cl,6-F-C6H3) | 1.6078 |
| 281 | 4-Cl-C6H4-C(Me)2-C6H4-CH(CH2O-)N=C-(2,6-F2-C6H3) | 1.5493 |
| 282 | 4-Cl-C6H4-C(Me)2-C6H4-CH(CH2O-)N=C-(2-Cl,6-F-C6H3) | 1.5862 |
| 283 | 4-Cl-C6H4-CH2CH2-C6H4-CH(CH2O-)N=C-(2,6-F2-C6H3) | 1.5869 |
| 284 | 4-Cl-C6H4-CH2CH2-C6H4-CH(CH2O-)N=C-(2-Cl,6-F-C6H3) | 1.5968 |

| | | |
|---|---|---|
| 285 | 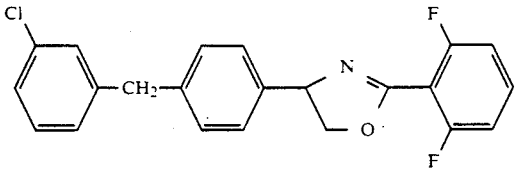 | 1.5946 |
| 286 | 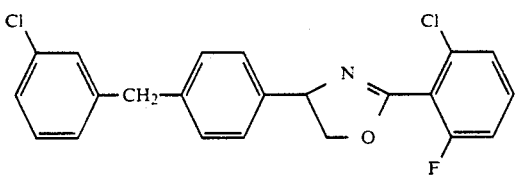 | 1.6047 |
| 287 | 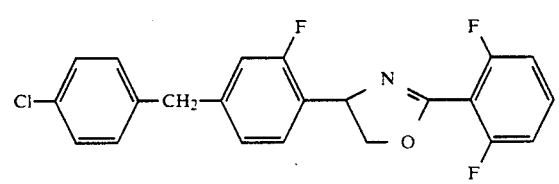 | 1.5908 |
| 288 | 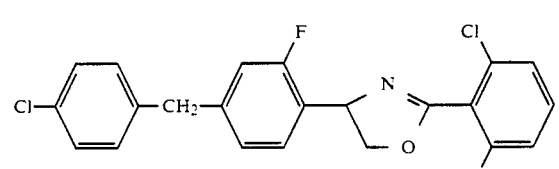 | 1.6035 |
| 289 | 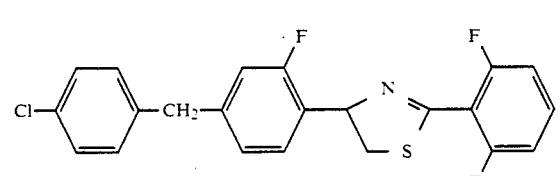 | 1.6166 |
| 290 | 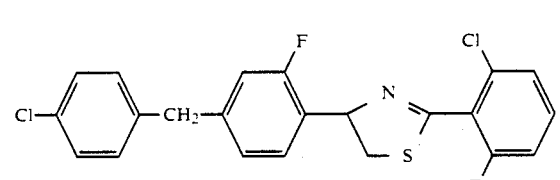 | 1.6178 |
| 291 | 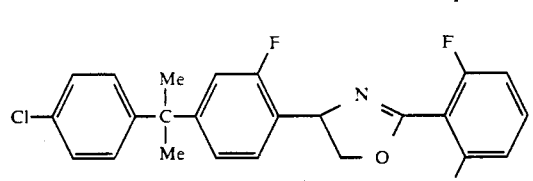 | 1.5624 |
| 292 | 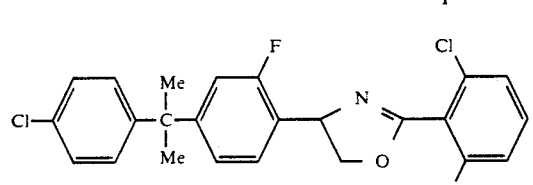 | 1.6084 |
| 293 | 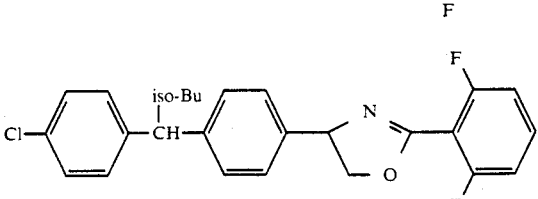 | 1.5768 |

-continued
| | | |
|---|---|---|
| 294 | 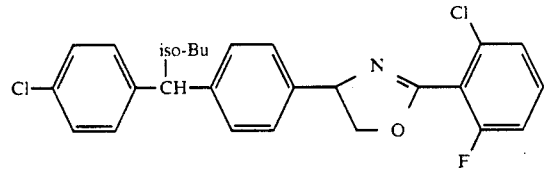 | 1.5896 |
| 295 | 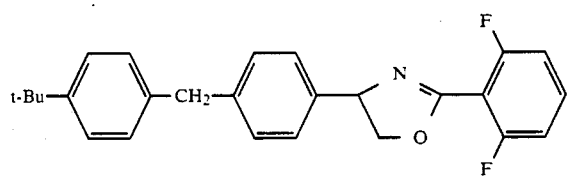 | 1.5716 |
| 296 | 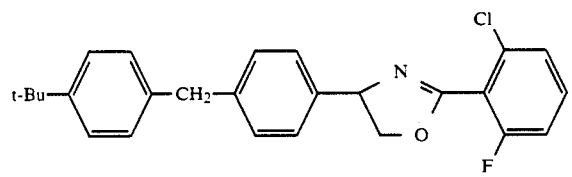 | 1.5835 |
| 297 | 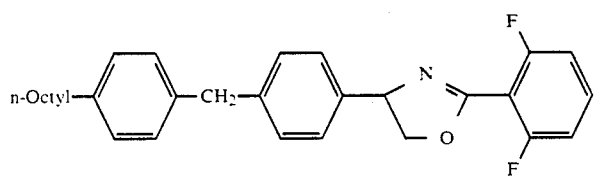 | 1.5514 |
| 298 | 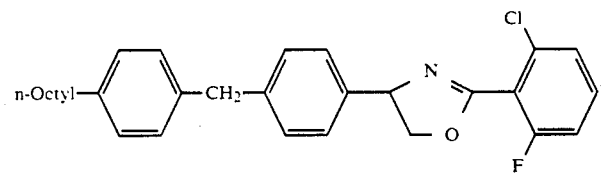 | 1.5620 |
| 299 | 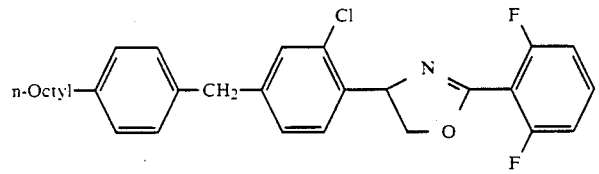 | 1.5474 |
| 300 | 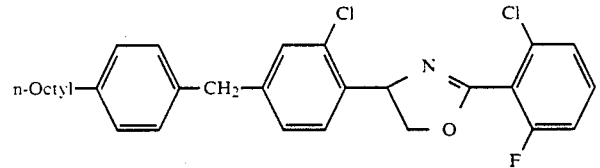 | 1.5585 |
| 301 | 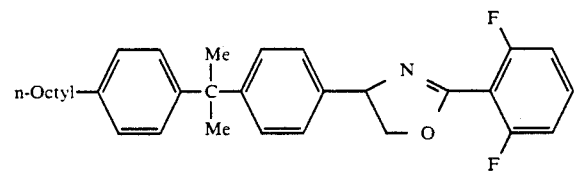 | 1.5372 |
| 302 | 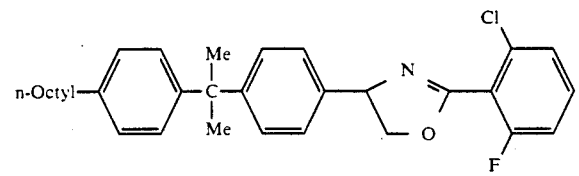 | 1.5421 |

-continued

| No. | Structure | Value |
|---|---|---|
| 303 | 2,4-F₂-C₆H₃-CH₂-C₆H₄-CH(CH₂O-)N=C-(2,6-F₂-C₆H₃) | 1.5699 |
| 304 | 2,4-F₂-C₆H₃-CH₂-C₆H₄-CH(CH₂O-)N=C-(2-Cl-6-F-C₆H₃) | 1.5802 |
| 305 | 4-F-C₆H₄-CH₂-(2-Cl-C₆H₃)-CH(CH₂O-)N=C-(2,6-F₂-C₆H₃) | 1.5961 |
| 306 | 4-F-C₆H₄-CH₂-(2-Cl-C₆H₃)-CH(CH₂O-)N=C-(2-Cl-6-F-C₆H₃) | 1.5999 |
| 307 | C₆H₅-O-C₆H₄-CH(CH₂O-)N=C-(2,6-F₂-C₆H₃) | 1.5923 |
| 308 | C₆H₅-O-C₆H₄-CH(CH₂O-)N=C-(2-Cl-6-F-C₆H₃) | 1.6023 |
| 309 | C₆H₅-O-C₆H₄-CH(O-)CH₂N=C-(2,6-F₂-C₆H₃) | 1.5845 |
| 310 | C₆H₅-O-C₆H₄-CH(CH₂O-)N=C-(2,6-Me₂-C₆H₃) | 1.6024 |
| 311 | C₆H₅-O-C₆H₄-CH(CH₂O-)N=C-(2-Cl-4-NO₂-C₆H₃) | 85~88* |

-continued
| | | |
|---|---|---|
| 312 | 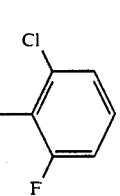 | 1.5989 |
| 313 | 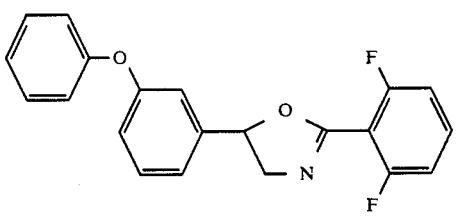 | 1.5884 |
| 314 | 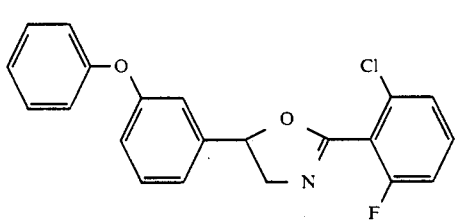 | 1.5991 |
| 315 | 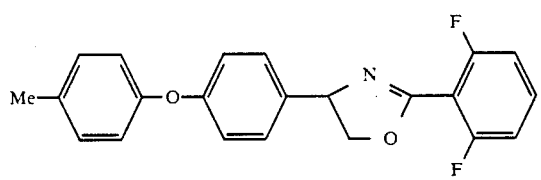 | 1.5867 |
| 316 | 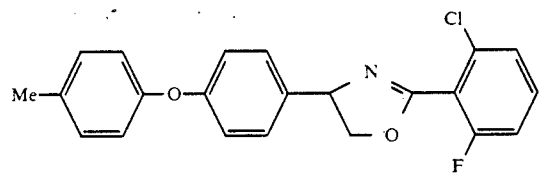 | 1.5968 |
| 317 | 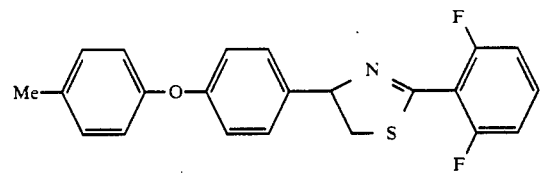 | 61~68* |
| 318 | 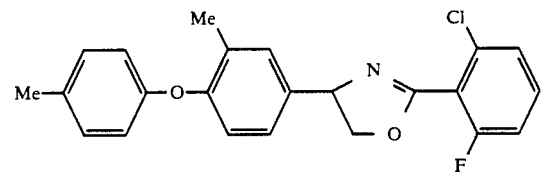 | 1.5878 |
| 319 | 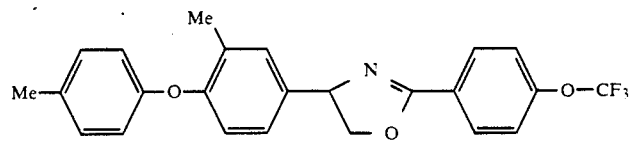 | 72~72.5* |

-continued
| | | |
|---|---|---|
| 320 | 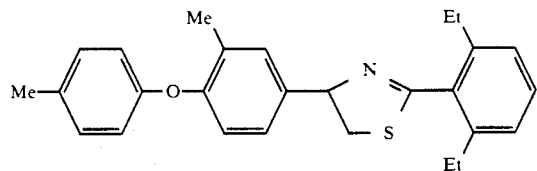 | 1.6061 |
| 321 | 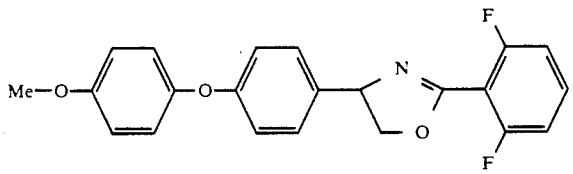 | 1.5891 |
| 322 | 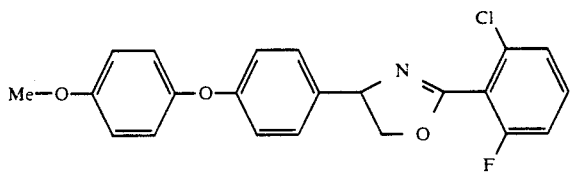 | 54~57* |
| 323 | 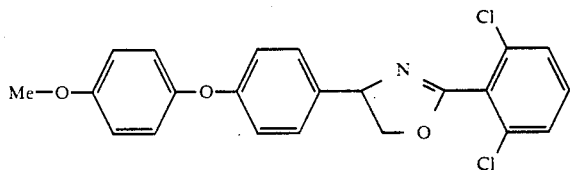 | 74~76* |
| 324 | 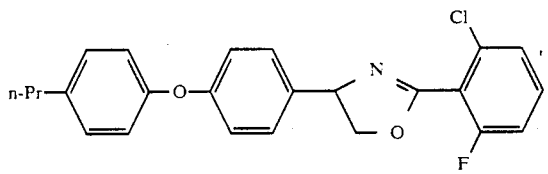 | 1.5861 |
| 325 | 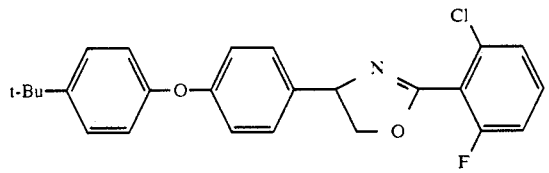 | 78~81* |
| 326 | 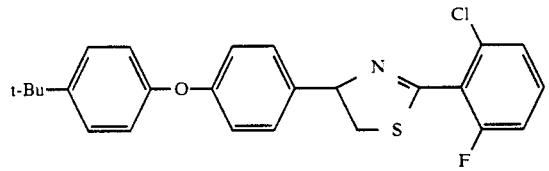 | 94~100* |
| 327 | 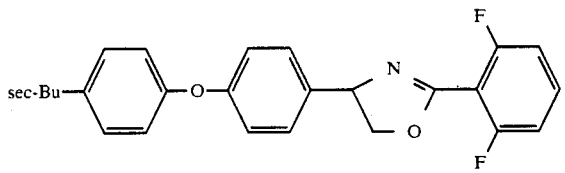 | 1.5717 |
| 328 | 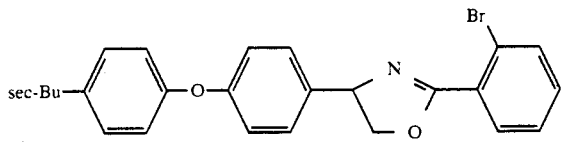 | 1.6046 |

-continued
| | | |
|---|---|---|
| 329 | 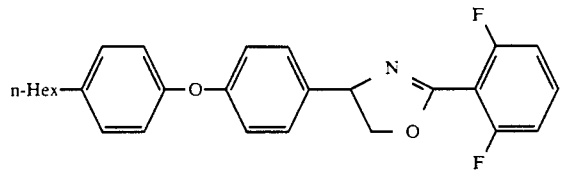 | 1.5621 |
| 330 | 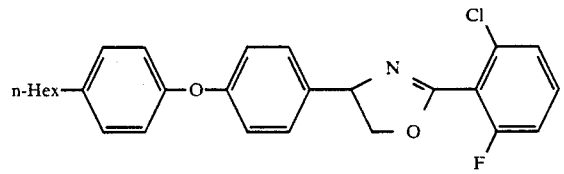 | 1.5707 |
| 331 | 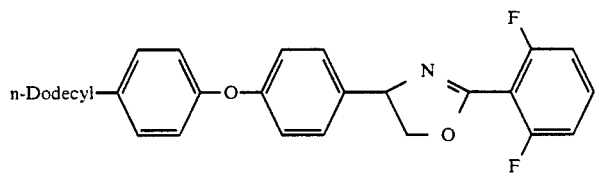 | 1.5387 |
| 332 | 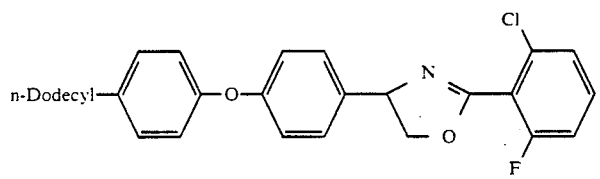 | 1.5494 |
| 333 | 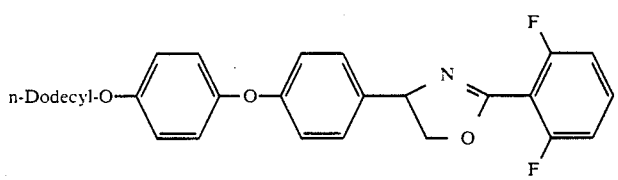 | 43~44* |
| 334 | 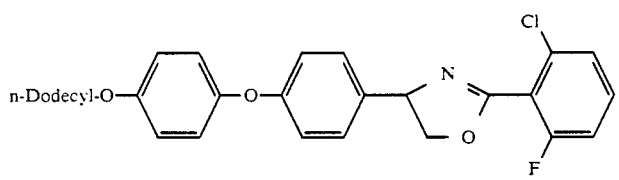 | 1.5493 |
| 335 | 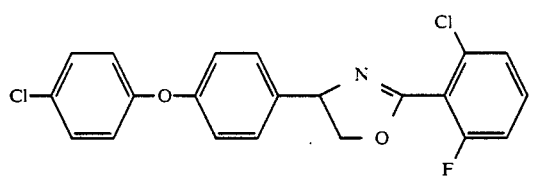 | 1.5573 |
| 336 | 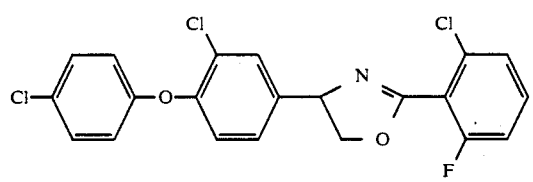 | 1.6106 |
| 337 | 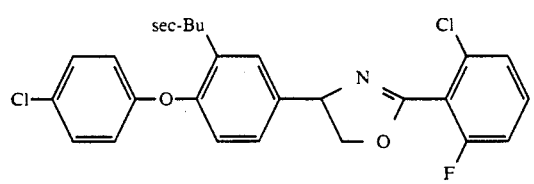 | 1.5818 |

-continued

| # | Structure | Value |
|---|---|---|
| 338 | 4-Cl-C6H4-O-(3-sec-Bu-phenyl)-CH(-N=C(-O-CH2-)(2-Cl-4-F-C6H3)) | 1.5905 |
| 339 | 3-CF3-C6H4-O-C6H4-CH(-N=C(-O-CH2-)(2,6-F2-C6H3)) | 1.5595 |
| 340 | 3-CF3-C6H4-O-C6H4-CH(-N=C(-O-CH2-)(2-Cl-6-F-C6H3)) | 1.5690 |
| 341 | 4-CF3-2-Cl-C6H3-O-C6H4-CH(-N=C(-O-CH2-)(2,6-F2-C6H3)) | 1.5846 |
| 342 | 4-CF3-2-Cl-C6H3-O-C6H4-CH(-N=C(-O-CH2-)(2-Cl-6-F-C6H3)) | 1.5918 |
| 343 | 4-CF3-2-Cl-C6H3-O-(2-F-C6H3)-CH(-N=C(-O-CH2-)(2,6-F2-C6H3)) | Amorphous |
| 344 | 4-CF3-2-Cl-C6H3-O-(2-F-C6H3)-CH(-N=C(-O-CH2-)(2-Cl-6-F-C6H3)) | Amorphous |
| 345 | CF3-O-C6H4-O-C6H4-CH(-N=C(-O-CH2-)(2-Cl-6-F-C6H3)) | 1.5542 |
| 346 | n-Octyl-O-(2,5-Me2-C6H2)-O-C6H4-CH(-N=C(-O-CH2-)(2,6-F2-C6H3)) | 1.5488 |

| | | |
|---|---|---|
| 347 | 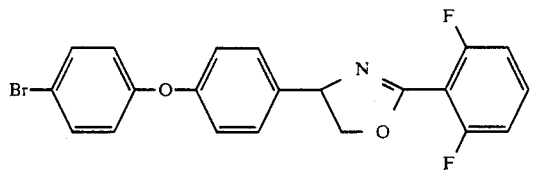 | 1.5982 |
| 348 | 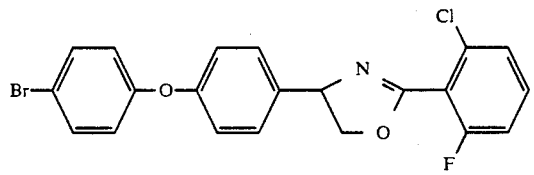 | 1.6083 |
| 349 | 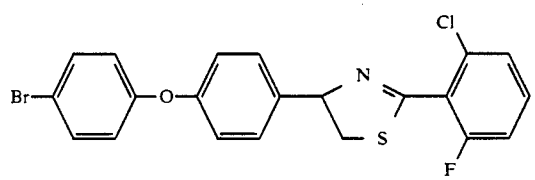 | 1.6350 |
| 350 | 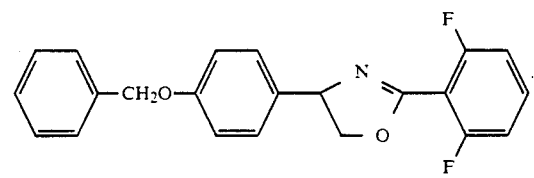 | 69~72* |
| 351 | 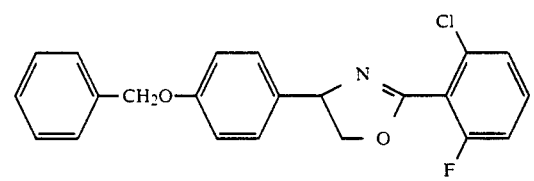 | 1.5965 |
| 352 | 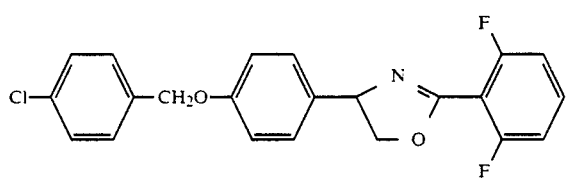 | 112~116* |
| 353 | 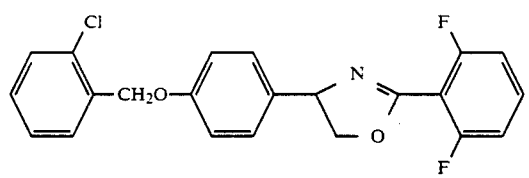 | 1.5942 |
| 354 | 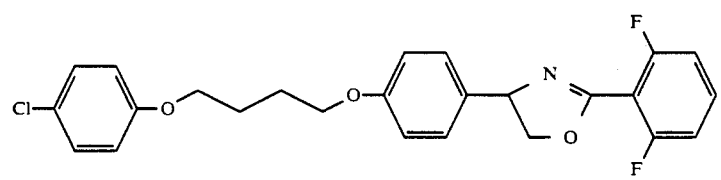 | 1.5678 |
| 355 | 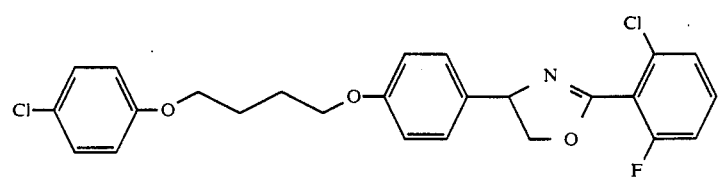 | 1.5598 |

| | | |
|---|---|---|
| 356 | 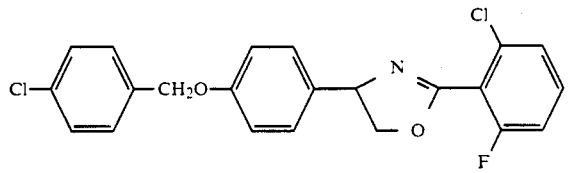 | 117.5~118* |
| 357 | 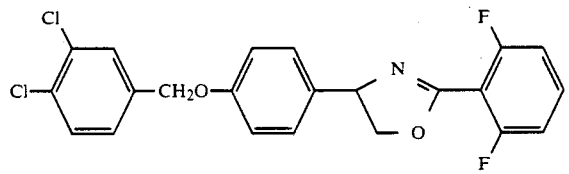 | 69~70.5* |
| 358 | 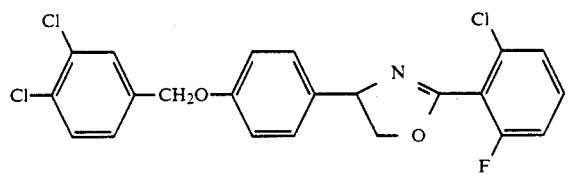 | 1.6049 |
| 359 | 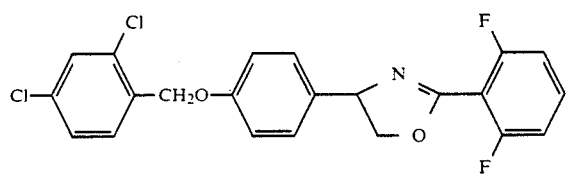 | 104~104.5* |
| 360 | 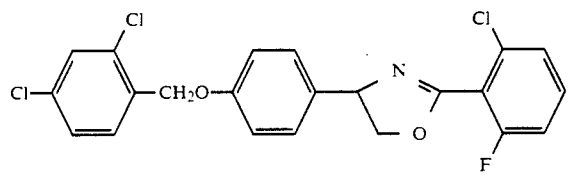 | 96~97* |
| 361 | 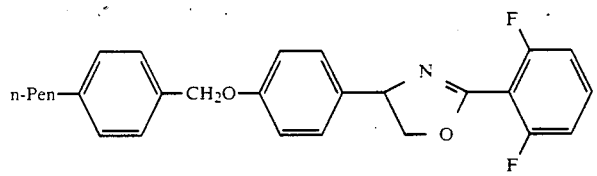 | 77.5~78.5* |
| 362 | 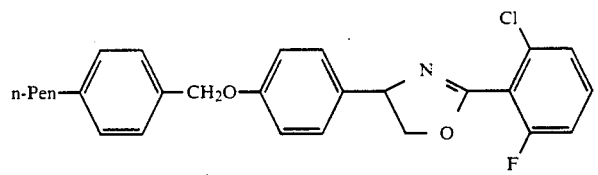 | 53.5~54* |
| 363 | 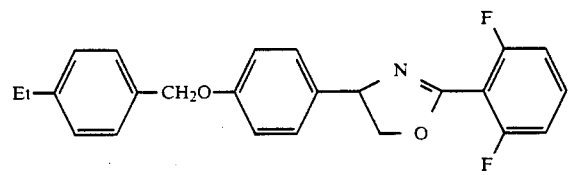 | 105~105.5* |
| 364 | 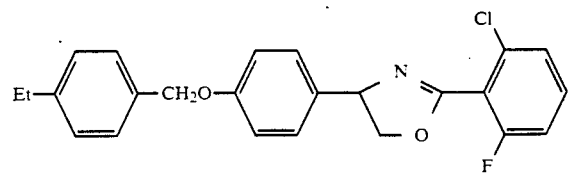 | 93~93.5* |

| | | |
|---|---|---|
| 365 | 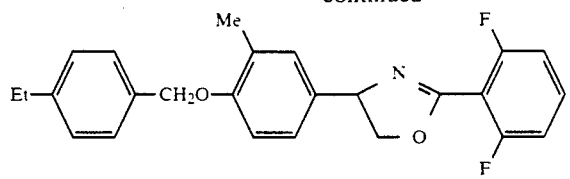 | 97.5~99.5* |
| 366 | 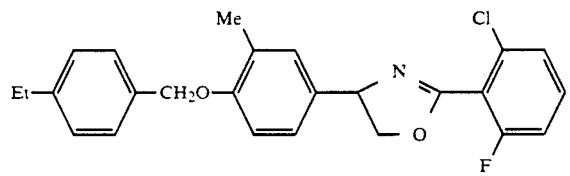 | 1.5784 |
| 367 | 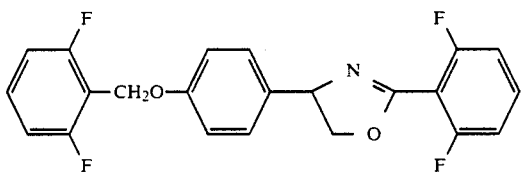 | 1.5632 |
| 368 | 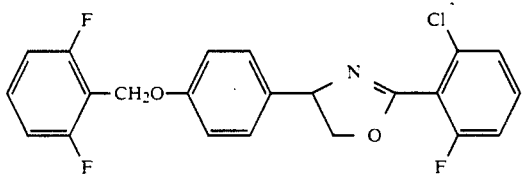 | 1.5742 |
| 369 | 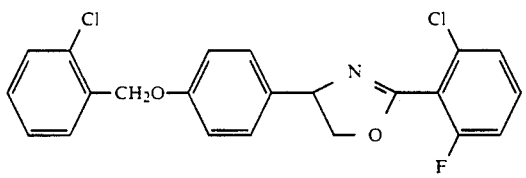 | 65~65.5* |
| 370 | 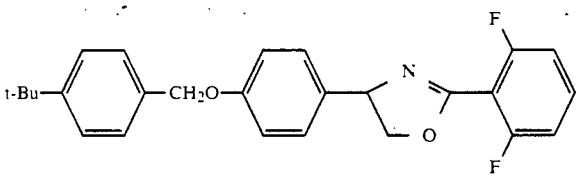 | 1.5649 |
| 371 | 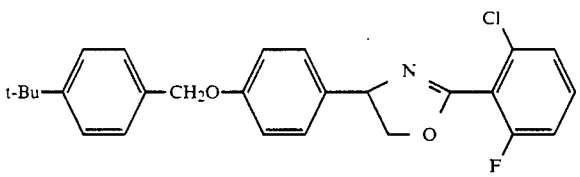 | 1.5797 |
| 372 | 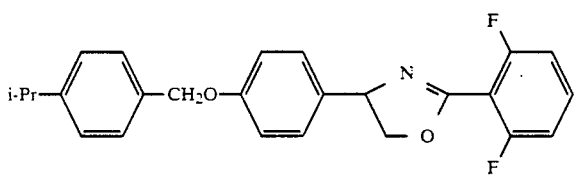 | 1.5741 |
| 373 | 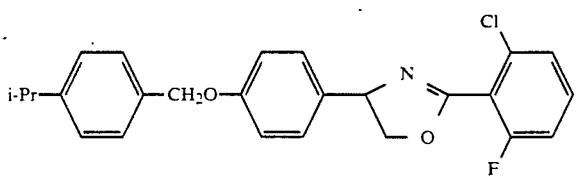 | 1.5838 |

-continued
| 374 | 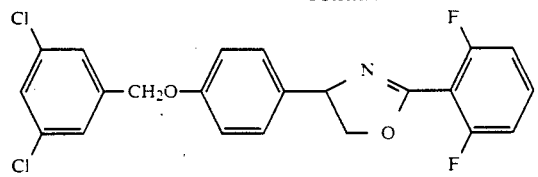 | 76~78* |
| 375 | 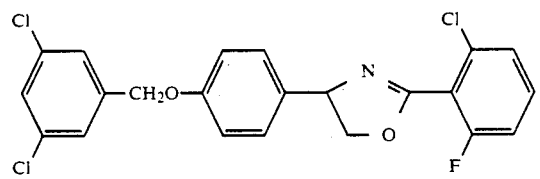 | 80~83* |
| 376 | 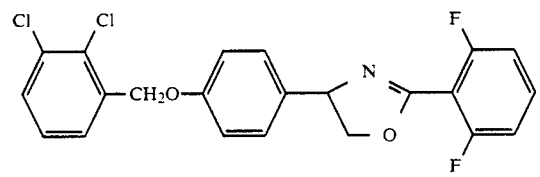 | 1.5936 |
| 377 | 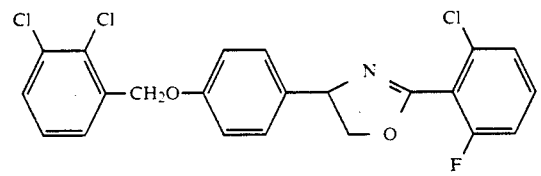 | 88~89.5* |
| 378 | 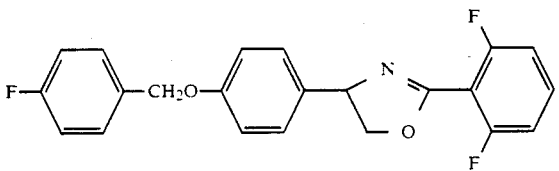 | 106~107* |
| 379 | 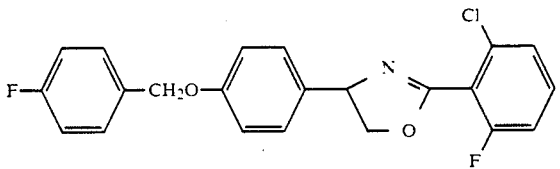 | 98.5~99* |
| 380 | 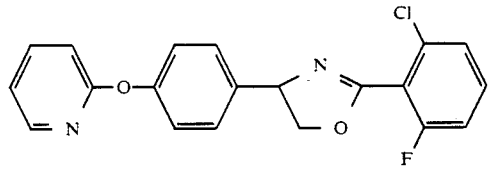 | 1.6034 |
| 381 | 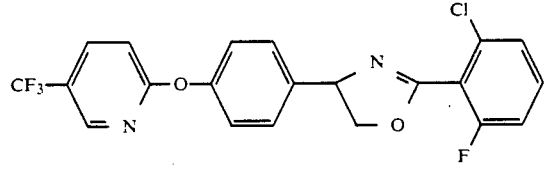 | 89~89.5* |
| 382 | 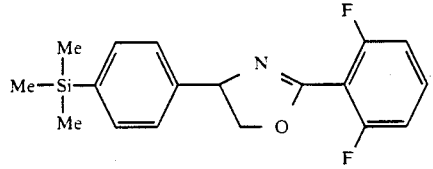 | 1.5444 |

| | | |
|---|---|---|
| 383 | 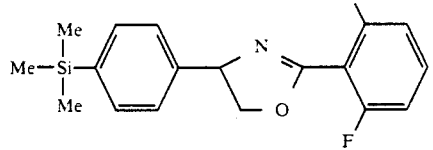 | 1.5556 |
| 384 | 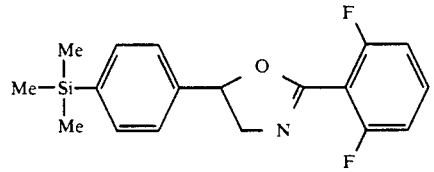 | 1.5476 |
| 385 | 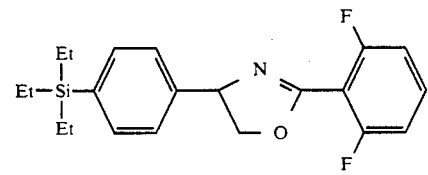 | 1.5444 |
| 386 | 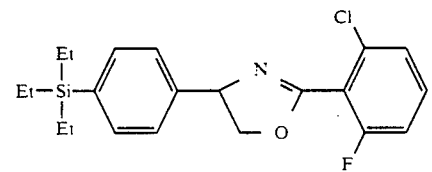 | 1.5496 |
| 387 | 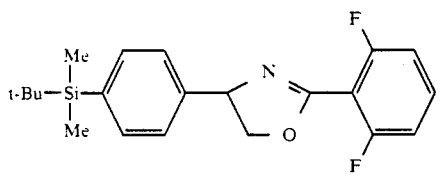 | 1.5413 |
| 388 | 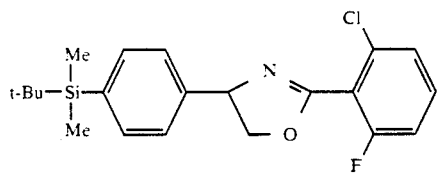 | 1.5549 |
| 389 | 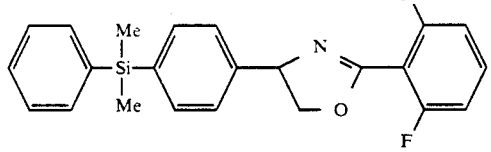 | 1.5778 |
| 390 | 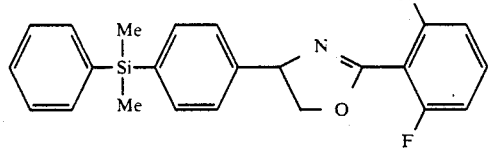 | 1.5886 |
| 391 | 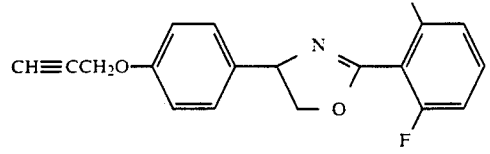 | 1.5807 |

392 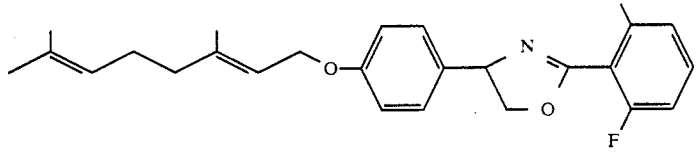 1.5482

393 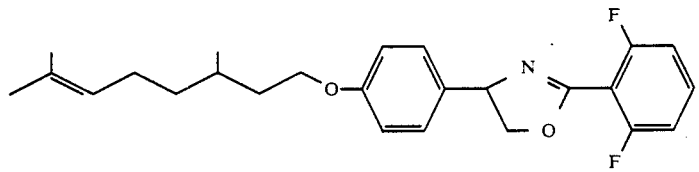 1.5352

394 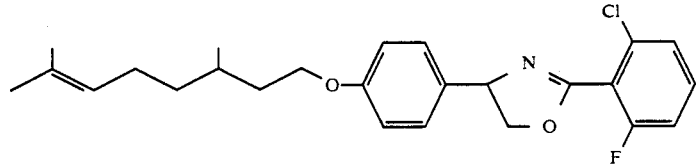 1.5450

The compounds of the above-mentioned general formula (I) provided by the present invention exhibit, as seen in the test examples mentioned afterward, intensive ovicidal, insecticidal and acaricidal activity against insects and/or mites harmful in agriculture, horticultire and/or epidemics prevention with little phytotoxicity to useful crops. Accordingly, they are useful as active ingredients of insecticides or acaricides for agriculture, horticulture and/or epidemics prevention.

The inventive compounds of the formula (I) exhibit an excellent controlling efficacy against insects and mites which have noxious influence on useful crops and/or epidemics prevention. These pests include, for example;

aphids such as *Myzus persicae, Aphis gossypii, Lipaphis erysimi, Aphis citricola, Nippolachnus piri* and the like;

Plant hoppers and leafhoppers such as *Nephotettix cincticeps, Laodelphax striatellus, Sogatella furcifera, Nilaparvata lugens* and the like;

stink bugs such as *Nezara antennata, Cletus punctiger, Riptortus clavatus* and the like;

thrips such as *Scirtothrips dorsalis, Thrips palmi, Ponticulothrips diospyrosi* and the like;

Orthoptera order harmful insects such as *Oxya yezoensis, Locusta migratoria* and the like;

Celeoptera order harmful insects such as *Anomala cuprea, Oulema oryzae, Epilachna vigintioctomaculata* and the like;

Diptera order harmful insects such as *Musca domestica, Culexpipiens* and the like;

Lepidoptera order harmful insects such as *Plutella xylostella, Spodoptera litura, Chilo suppressalis* and the like; and mites such as *Tetranychus urticae, Tetranychus cinnabarinus, Tetranychus kanzawai, Panonychus ulmi, Panonychus citri* and the like.

Accordingly, the active compounds of the formula (I) are useful as the effective ingredient in insecticides or acaricides for agriculture, horticulture and/or epidemics prevention.

In the practical uses of the inventive compounds as the effective ingredient for insecticides or acaricides, the compound of formula (I) may be either alone in one kind or as a combination of two or more kinds thereof and may be formulated in various forms optionally combined with another auxiliary agent allowable in agricultural or hortucultural uses or in epidemics prevention. The useful auxiliary agents in formulation include carriers, surface active agents, dispersing agents, binders, stabilizing agents and the like and the formulations should incorporate any of them selected optionally from them according to the requirement.

The carriers or diluents comprise those in the form of solid or liquid exemplified by mineral powder or granules such as diatomaceous earth, talc, clay, alumina, kaolin, montmorillonite, silicic acid, white carbon and the like and powder of animal or vegetable nature such as starch, soybean powder, flour, fish meal and the like as the solid type thereof and water, alcohols including methanol, ethyleneglycol, phenoxyethanol and the like, ketones including acetone, methylethyl ketone and the like, aromatic hydrocarbons including xylene, trimethyl benzene, methyl naphthalene, solvent naphtha and the like, aliphatic hydrocarbons including hexane, cyclohexane, kerosene, lamp oil and the like, ethers including dioxane, diisopropyl ether, tetrahydrofuran and the like, halogenated hydrocarbons including dichloromethane, trichloroethane and the like, amides including dimethyl formamide and the like, nitrils including acetonitrile and the lke, sulfur compounds including dimethyl sulfoxide and the like, vegetable oils including soybean oil, olive oil and the like, and so forth.

The useful surface active agents comprise, for Example, those of the nonionic type such as polyoxyalkylene alkyl ethers, polyoxyalkylene alkyl aryl ethers, polyoxyalkylene fatty acid esters, polyoxyalkylene sorbitan fatty acid esters and the like, and those of anionic type such as alkylaryl sulfate ester salts, polyoxyalkylene alkylaryl sulfate esters and the like and mixtures of these.

The dispersing agents or binders are exemplified by lignin sulfonic acid salts, naphthalene sulfonic acid-formaldehyde condensate, alginic acid salt, starch, cellulose derivative, montmorillonite, synthetic water-soluble polymers, synthetic resins and the like.

The stabilizing agents are exemplified by phosphoric acid esters, glycols, nonionic surface active agents, aromatic diamines, vegetable oils, epoxidized fatty oils and the like.

Furthermore, preparations containing the inventive compounds of formula (I) may be used as a mixture or a composition with another agrochemical selected according to the requirement from other types of insecticides or acaricides, germicides, attractants and the like thereby to exhibit a more favorable effect.

The insecticides or acaricides to be used with such an object include, for example, organophosphate compounds such as Fenitrothion (O,O-dimethyl O-4-nitro-m-tolyl phosphorothioate), Diazinon (O,O-diethyl O-2-isopropyl-6-methylpyrimidin-4-yl phosphorothioate), Chlorpyrifos-methyl [O,O-dimethyl 0-(3,5,6-trichloro-2-pyridyl)phosphorothioate] and Acephate (O,S-dimethylacetyl phosphoroamidothioate); carbamate compounds such as Carbaryl (1-naphthylmethyl carbamate), Carbofuran (2,3-dihydro-2,2-dimethylbenzofuran-7-yl-methylcarbamate) and [Methomyl S-methyl N-(methylcarbamoyloxy)thioacetoimidate]; organochlorine compounds such ad Dicofol [2,2,2-trichloro-1,1-bis(4-chlorophenyl)ethanol]; organometallic compounds such as Fenbutatin oxide [hexakis(beta,beta-dimethylphenethyl)distannoxane]; pyrethroid compounds such as Fenvalerate [(RS)-alpha-cyano-3-phenoxybenzyl (RS)-2-(4-chlorophenyl)-3-methylbutyrate)] and Permethrin [3-phenoxybenzyl (1RS)-cis,-trans-3-(2,2-dichlorovinyl)-2,2-dimethylcyclopropane carboxylate]; benzoylurea compounds such as Diflubenzuron 1-(4-chlorophenyl)-3-(2,6-difluorobenzoyl)urea] and Chlorfluazuron [1-(3,5-dichloro-4-(3-chloro-5-trifluoromethyl-2-pyridyloxy)phenyl)-3-(2,6-difluorobenzoyl)urea]; and other compounds such as Buprofezin (2-t-butylimino-3-isopropyl-5-phenyl-3,4,5,6-tetrahydro-2H-1,3,5-thiadiazin-4-one) and Hexythiazox [trans-5-(4-chlorophenyl)-N-cyclohexyl-4-methyl-2-oxo-thiazolidinone-3-carboxamide).

Examples of the fungicides include organophosphorus compounds such as Iprobenfos (S-benzyl O,O-diisopropylphosphorothioate) and Edifenphos (O-ethyl S,S-diphenylphosphorodithioate); organochlorine compounds sucha as Phthalide (4,5,6,7-tetrachlorophthalide); dithiocarbamate compounds such as a polymer of Zineb [zinc ethylenebis(dithiocarbamate)] and polycarbamate [dizincbis(dimethyldithiocarbamate)]; N-halogenothioalkyl compounds such as Captan [3a,4,7-,7a-tetrahydro-N-(trichloromethanesulfenyl)phthalimide] and Captafol [3a,4,7,7a-tetrahydro-N-(1,1,2,2-tetrachloroethane-sulfenyl)phthalimide]; dicarboximide compounds such as Glycophene 3-(3,5-dichlorophenyl)-N-isopropyl-2,4-dioxoimidazolidin-1-carboxamide], Vinclozolin (RS)-3-(3,5-dichlorophenyl)-5-methyl-5-vinyl-1,3-oxazolidin-2,4-dione] and Procymidone [1-(3,5-diclorophenyl)-1,2-dimethylcyclopropane-1,2-dicarboximide]; benzimidazole compounds such as Benomyl [methyl 1-(butylcarbamoyl)benzimidazole-2-yl carbamate]; azole compounds such as Bitertanol [1-(biphenyl-4-yloxy)-3,3-dimethyl-1-(1H-1,2,4-triazol-1-yl)butan-2-ol] and Triflumizole [1-(N-(4-chloro-2-trifluoromethylphenyl)-2-propoxyacetimidoyl)-imidazole]; and benzanilide compounds such as Mepronil (3-isopropoxy-O-toluanilide) and Flutolanil (alpha,alpha,alpha-trifluoro-3-isopropoxy-O-toluanilide).

Illustrative of the attractant are benzoic acid, 4-allyl-2-methoxyphenol and 4-(p-acetoxyphenyl)-2-butanone.

The compound (I) of this invention may be formulated into a wettable powder, granules, a dust, a pulverulent composition, an emulsifiable concentrate, a flowable, etc. together with the above-described adjuvants by methods known in the field of preparing chemicals for agriculture, horticulture or epidemics prevention.

The proportion of the active compounds of formula (I) in the formulations may be varied widely depending on the kind of the compound (I), the type of formulation, etc. In general, the suitable proportion of the compound should be in the range of 0.01 to 80% by weight or, more specifically depending on the type of formulation, 0.01 to 50% by weight or, more preferably, 0.1 to 20% by weight for liquid type formulations such as an emulsifiable concentrate, a wettable powder, a flowable agent and the like or 0.01 to 20% by weight or, more preferably, 0.1 to 10% by weight for solid type formulations such as a dust, granules and the like.

The formulation containing the compound (I) of the invention may be used to control noxious insects or mites by spreading the effective ingredient of the formula (I) directly against imagoes, larvae or eggs of insects and/or mites noxious for agricultural or horticultural crops or in prevention of epidemics or to the area in which imagoes, larvae or eggs thereof live.

The rate of the compound of formula (I) to be applied at this time may be properly varied depending upon the type of the active compound, the type of the formulation, the state of occurrence of the pests, etc. It may be applied generally at a rate of 1 to 10,000 g/hectare, preferably 10 to 1,000 g/hectare. Specifically, in the case of the emulsifiable concentrate, liquid preparation and wettable powder, they are usually diluted to 1,000 to 10,000 times, and can be applied at a rate of 1,000 to 10,000 liters per hectare. In the case of the dust, pulverulent composition and granules, they may be applied at a rate of 10 to 100 kg per hectare.

Following are formulation examples of the inventive compound (I) but they should not be considered as the basis of restricting the scope of the invention. All terms "part(s)" in the examples indicate part(s) by weight.

FORMULATION EXAMPLE 1

Eemulsifiable Concentrate

An emulsifiable concentrate is prepared by adding 80 parts of xylene to 10 parts of the inventive compound (Compound Number 6), 5 parts of an alkyl aryl sulfonate and 5 parts of an polyoxyalkylene alkyl aryl ether.

FORMULATION EXAMPLE 2

Wettable Powder

A wettable powder is prepared by pulverizing a mixture of 10 parts of the inventive compound (Compound Number 145), 5 parts of a polyoxyalkylene alkyl aryl sulfuric acid ester salt, 5 parts of a lignin sulfonate salt, 10 parts of White Carbon and 70 parts of diatomaceous earth.

FORMULATION EXAMPLE 3

Pulverulent Composition

A pulverulent is prepared by pulverizing a mixture of one part of the inventive compound (Compound Number 315), one part of White Carbon and 98 parts of fine powdered talc.

FORMULATION EXAMPLE 4

Granules

Granules are prepared by kneading a uniform mixture of 5 parts of the inventive compound (Compound Number 382), 0.5 part of a dodecylbenzene sulfonic acid salt, 3.5 parts of a lignin sulfonic acid salt, 30 parts of bentonite and 61 parts of talc with a suitable amount of water followed by granulating using a granulater and drying by aeration using a fluidized drying apparatus.

FORMULATION EXAMPLE 5

Flowable Agent

A flowable agent is prepared by uniformly dispersing 10 parts of the inventive compound (Compound Number 352), 5 parts of a polyoxyalkylene alkyl aryl ether, 5 parts of ethyleneglycol and 79.8 parts of water by stirring followed by admixing 0.2 part of xanthane gum as the extender.

The followings are test examples having an object of proving the excellent activity of the inventive compound of the formula (I) as an insecticide or acaricide.

TEST EXAMPLE 1

Ovicidal Test For Two-Spotted Spider Mite

Each cup (9 cm in diameter) was filled with water and a lid having a hole was fitted therein. A piece of filter paper was laid on the lid to be moistened allover by water absorption. Kidney bean leave was placed on the moistened filter paper and 10 female imagoes of two-spotted spider mite (*Tetranychs urticae koch*) were inoculated to the kidney bean leave to be allowed to lay eggs for 24 hours and the female imagoes were removed thereafter. A drug preparation (obtained by diluting the emulsifiable concentrate in Formulation Example 1 with water) with a predetermined concentration was spread thereon followed by standing still in a thermostat chamber kept at 25° C. for 7 days and the ovicidal rate was determined by microscopic inspection of the number of hatched larvae. The test was conducted through 3 replications for each area. The results are shown in Table 2 below.

TEST EXAMPLE 2

Ovicidal Test For Kanzawa Spider Mite

Each cup (9 cm in diameter) was filled with water and a lid having a hole was fitted therein. A piece of filter paper was laid on the lid to be moistened allover by water absorption. Kidney bean leave was placed on the moistened filter paper and 10 female imagoes of Kanzawa spider mite (*Tetranycus kanzawai Kishida*) were inoculated to the kidney bean leave to be allowed to lay eggs for 24 hours and the female imagoes were removed thereafter. A drug preparation (obtained by diluting the emulsifiable concentrate in Formulation Example 1 with water) with a predetermined concentration was spread thereon followed by standing still in a thermostat chamber kept at 25° C. for 7 days and the ovicidal rate was determined by microscopic inspection of the number of hatched larvae. The test was conducted through 3 replications for each area. The results are shown in Table 2 below.

TABLE 2

| Compound Number | ovicidal rate (%)* | |
| --- | --- | --- |
| | two-spotted spider mite 100 ppm | Kanzawa spider mite 100 ppm |
| 1 | 100 | 100 |
| 2 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| 15 | 100 | 100 |
| 16 | 100 | 100 |
| 18 | 100 | 100 |
| 19 | 100 | 100 |
| 20 | 100 | 100 |
| 21 | 100 | 100 |
| 22 | 100 | 100 |
| 23 | 100 | 100 |
| 24 | 100 | 100 |
| 25 | 100 | 100 |
| 26 | 100 | 100 |
| 27 | 100 | 100 |
| 28 | 100 | 100 |
| 29 | 100 | 100 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66 | 100 | 100 |
| 67 | 100 | 100 |
| 68 | 100 | 100 |
| 69 | 100 | 100 |
| 70 | 100 | 100 |
| 71 | 100 | 100 |
| 72 | 100 | 100 |
| 73 | 100 | 100 |
| 74 | 100 | 100 |
| 75 | 100 | 100 |
| 76 | 100 | 100 |
| 77 | 100 | 100 |
| 78 | 100 | 100 |
| 81 | 100 | 100 |
| 82 | 100 | 100 |
| 83 | 100 | 100 |
| 84 | 100 | 100 |
| 85 | 100 | 100 |
| 86 | 100 | 100 |
| 87 | 100 | 100 |

TABLE 2-continued

| Compound Number | ovicidal rate (%)* two-spotted spider mite 100 ppm | Kanzawa spider mite 100 ppm |
|---|---|---|
| 88 | 100 | 100 |
| 89 | 100 | 100 |
| 92 | 100 | 100 |
| 93 | 100 | 100 |
| 94 | 100 | 100 |
| 95 | 100 | 100 |
| 96 | 100 | 100 |
| 97 | 100 | 100 |
| 98 | 100 | 100 |
| 99 | 100 | 100 |
| 100 | 100 | 100 |
| 101 | 100 | 100 |
| 102 | 100 | 100 |
| 103 | 100 | 100 |
| 104 | 100 | 100 |
| 105 | 100 | 100 |
| 106 | 100 | 100 |
| 107 | 100 | 100 |
| 108 | 100 | 100 |
| 109 | 100 | 100 |
| 110 | 100 | 100 |
| 115 | 100 | 100 |
| 119 | 100 | 100 |
| 120 | 100 | 100 |
| 125 | 100 | 100 |
| 126 | 100 | 100 |
| 127 | 100 | 100 |
| 128 | 100 | 100 |
| 129 | 100 | 100 |
| 130 | 100 | 100 |
| 131 | 100 | 100 |
| 132 | 100 | 100 |
| 133 | 100 | 100 |
| 134 | 100 | 100 |
| 135 | 100 | 100 |
| 136 | 100 | 100 |
| 137 | 100 | 100 |
| 138 | 100 | 100 |
| 140 | 100 | 100 |
| 141 | 100 | 100 |
| 142 | 100 | 100 |
| 143 | 100 | 100 |
| 144 | 100 | 100 |
| 145 | 100 | 100 |
| 146 | 100 | 100 |
| 150 | 100 | 100 |
| 152 | 100 | 100 |
| 153 | 100 | 100 |
| 155 | 100 | 100 |
| 156 | 100 | 100 |
| 157 | 100 | 100 |
| 158 | 100 | 100 |
| 159 | 100 | 100 |
| 160 | 100 | 100 |
| 161 | 100 | 100 |
| 162 | 100 | 100 |
| 163 | 100 | 100 |
| 164 | 100 | 100 |
| 165 | 100 | 100 |
| 166 | 100 | 100 |
| 167 | 100 | 100 |
| 168 | 100 | 100 |
| 169 | 100 | 100 |
| 170 | 100 | 100 |
| 171 | 100 | 100 |
| 172 | 100 | 100 |
| 173 | 100 | 100 |
| 174 | 100 | 100 |
| 175 | 100 | 100 |
| 176 | 100 | 100 |
| 177 | 100 | 100 |
| 178 | 100 | 100 |
| 179 | 100 | 100 |
| 180 | 100 | 100 |
| 181 | 100 | 100 |
| 182 | 100 | 100 |
| 183 | 100 | 100 |
| 184 | 100 | 100 |
| 185 | 100 | 100 |
| 186 | 100 | 100 |
| 187 | 100 | 100 |
| 188 | 100 | 100 |
| 189 | 100 | 100 |
| 190 | 100 | 100 |
| 191 | 100 | 100 |
| 192 | 100 | 100 |
| 193 | 100 | 100 |
| 194 | 100 | 100 |
| 195 | 100 | 100 |
| 196 | 100 | 100 |
| 197 | 100 | 100 |
| 198 | 100 | 100 |
| 199 | 100 | 100 |
| 200 | 100 | 100 |
| 201 | 100 | 100 |
| 202 | 100 | 100 |
| 203 | 100 | 100 |
| 205 | 100 | 100 |
| 206 | 100 | 100 |
| 207 | 100 | 100 |
| 208 | 100 | 100 |
| 209 | 100 | 100 |
| 211 | 100 | 100 |
| 212 | 100 | 100 |
| 213 | 100 | 100 |
| 214 | 100 | 100 |
| 215 | 100 | 100 |
| 216 | 100 | 100 |
| 217 | 100 | 100 |
| 218 | 100 | 100 |
| 219 | 100 | 100 |
| 220 | 100 | 100 |
| 221 | 100 | 100 |
| 222 | 100 | 100 |
| 223 | 100 | 100 |
| 224 | 100 | 100 |
| 225 | 100 | 100 |
| 228 | 100 | 100 |
| 229 | 100 | 100 |
| 230 | 100 | 100 |
| 231 | 100 | 100 |
| 232 | 100 | 100 |
| 233 | 100 | 100 |
| 234 | 100 | 100 |
| 235 | 100 | 100 |
| 236 | 100 | 100 |
| 237 | 100 | 100 |
| 238 | 100 | 100 |
| 239 | 100 | 100 |
| 240 | 100 | 100 |
| 242 | 100 | 100 |
| 243 | 100 | 100 |
| 244 | 100 | 100 |
| 246 | 100 | 100 |
| 247 | 100 | 100 |
| 248 | 100 | 100 |
| 249 | 100 | 100 |
| 250 | 100 | 100 |
| 251 | 100 | 100 |
| 252 | 100 | 100 |
| 253 | 100 | 100 |
| 254 | 100 | 100 |
| 255 | 100 | 100 |
| 256 | 100 | 100 |
| 257 | 100 | 100 |
| 258 | 100 | 100 |
| 259 | 100 | 100 |
| 260 | 100 | 100 |
| 261 | 100 | 100 |
| 262 | 100 | 100 |
| 263 | 100 | 100 |
| 264 | 100 | 100 |
| 265 | 100 | 100 |
| 266 | 100 | 100 |

TABLE 2-continued

| Compound Number | ovicidal rate (%)* two-spotted spider mite 100 ppm | Kanzawa spider mite 100 ppm |
|---|---|---|
| 267 | 100 | 100 |
| 269 | 100 | 100 |
| 270 | 100 | 100 |
| 271 | 100 | 100 |
| 272 | 100 | 100 |
| 273 | 100 | 100 |
| 274 | 100 | 100 |
| 275 | 100 | 100 |
| 276 | 100 | 100 |
| 277 | 100 | 100 |
| 278 | 100 | 100 |
| 279 | 100 | 100 |
| 280 | 100 | 100 |
| 281 | 100 | 100 |
| 282 | 100 | 100 |
| 283 | 100 | 100 |
| 284 | 100 | 100 |
| 285 | 100 | 100 |
| 286 | 100 | 100 |
| 287 | 100 | 100 |
| 288 | 100 | 100 |
| 289 | 100 | 100 |
| 290 | 100 | 100 |
| 291 | 100 | 100 |
| 292 | 100 | 100 |
| 293 | 100 | 100 |
| 294 | 100 | 100 |
| 296 | 100 | 100 |
| 297 | 100 | 100 |
| 298 | 100 | 100 |
| 299 | 100 | 100 |
| 300 | 100 | 100 |
| 302 | 100 | 100 |
| 303 | 100 | 100 |
| 304 | 100 | 100 |
| 305 | 100 | 100 |
| 306 | 100 | 100 |
| 307 | 100 | 100 |
| 308 | 100 | 100 |
| 310 | 100 | 100 |
| 311 | 100 | 100 |
| 312 | 100 | 100 |
| 313 | 100 | 100 |
| 315 | 100 | 100 |
| 316 | 100 | 100 |
| 317 | 100 | 100 |
| 318 | 100 | 100 |
| 321 | 100 | 100 |
| 322 | 100 | 100 |
| 323 | 100 | 100 |
| 324 | 100 | 100 |
| 325 | 100 | 100 |
| 326 | 100 | 100 |
| 327 | 100 | 100 |
| 328 | 100 | 100 |
| 329 | 100 | 100 |
| 330 | 100 | 100 |
| 331 | 100 | 100 |
| 332 | 100 | 100 |
| 333 | 100 | 100 |
| 334 | 100 | 100 |
| 335 | 100 | 100 |
| 336 | 100 | 100 |
| 339 | 100 | 100 |
| 340 | 100 | 100 |
| 341 | 100 | 100 |
| 342 | 100 | 100 |
| 343 | 100 | 100 |
| 344 | 100 | 100 |
| 345 | 100 | 100 |
| 346 | 100 | 100 |
| 347 | 100 | 100 |
| 348 | 100 | 100 |
| 349 | 100 | 100 |
| 350 | 100 | 100 |
| 351 | 100 | 100 |
| 352 | 100 | 100 |
| 353 | 100 | 100 |
| 354 | 100 | 100 |
| 355 | 100 | 100 |
| 356 | 100 | 100 |
| 357 | 100 | 100 |
| 358 | 100 | 100 |
| 359 | 100 | 100 |
| 360 | 100 | 100 |
| 361 | 100 | 100 |
| 362 | 100 | 100 |
| 363 | 100 | 100 |
| 364 | 100 | 100 |
| 365 | 100 | 100 |
| 366 | 100 | 100 |
| 367 | 100 | 100 |
| 368 | 100 | 100 |
| 369 | 100 | 100 |
| 370 | 100 | 100 |
| 371 | 100 | 100 |
| 372 | 100 | 100 |
| 373 | 100 | 100 |
| 374 | 100 | 100 |
| 375 | 100 | 100 |
| 376 | 100 | 100 |
| 377 | 100 | 100 |
| 378 | 100 | 100 |
| 379 | 100 | 100 |
| 380 | 100 | 100 |
| 381 | 100 | 100 |
| 382 | 100 | 100 |
| 383 | 100 | 100 |
| 385 | 100 | 100 |
| 386 | 100 | 100 |
| 387 | 100 | 100 |
| 388 | 100 | 100 |
| 389 | 100 | 100 |
| 390 | 100 | 100 |
| 391 | 100 | 100 |
| 392 | 100 | 100 |
| 393 | 100 | 100 |
| 394 | 100 | 100 |
| Control A** | 0 | 0 |
| Control B*** | 0 | 0 |

*ovicidal rate (%) = $\frac{(\text{No. of layed eggs} - \text{No. of hatched larvae})}{\text{No. of layed eggs}} \cdot 100$

**Control A = PESTICIDE BIOCHEMISTRY AND PHYSIOLOGY, 30, 190-197 (1988) Compound No. AC-5

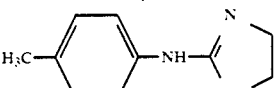

***Control B = PCT:WO82/02046

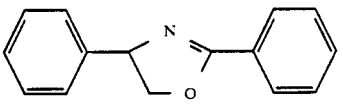

TEST EXAMPLE 3

Acaricidal Test For Larvae Of Two-Spotted Spider Mite

Each cup (9 cm in diameter) was filled with water and a lid having a hole was fitted therein. A piece of filter paper was laid on the lid to be moistened allover by water absorption. Kidney bean leave was placed on the moistened filter paper and 10 female imagoes of twospotted spider mite were inoculated to the kidney bean leave to be allowed to lay eggs for 24 hours and the female imagoes were removed thereafter. The cup was stood still in a thermostat chamber kept at 25° C.

for 7 days. Then the number of hatched larvae was counted and a drug preparation (obtained by diluting the emulsifiable concentrate in Formulation Example 1 with water) with a predetermined concentration was spread thereon followed by standing still in a thermostat chamber kept at 25° C. After further 7 days the number of surviving imagoes was microscopically examined and the ratio to the number of hatched larvae was obtaind. The test was conducted through 3 replications for each area. The results are shown in Table 3 below.

TABLE 3

| Compound Number | acaricidal rate (%)* | |
|---|---|---|
| | 500 ppm | 100 ppm |
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |
| 14 | 100 | 100 |
| 15 | 100 | 100 |
| 16 | 100 | 100 |
| 18 | 100 | 100 |
| 19 | 100 | 100 |
| 20 | 100 | 100 |
| 21 | 100 | 100 |
| 22 | 100 | 100 |
| 23 | 100 | 100 |
| 24 | 100 | 100 |
| 25 | 100 | 100 |
| 26 | 100 | 100 |
| 27 | 100 | 100 |
| 28 | 100 | 100 |
| 29 | 100 | 100 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |
| 52 | 100 | 100 |
| 53 | 100 | 100 |
| 54 | 100 | 100 |
| 55 | 100 | 100 |
| 56 | 100 | 100 |
| 57 | 100 | 100 |
| 58 | 100 | 100 |
| 59 | 100 | 100 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66 | 100 | 100 |
| 67 | 100 | 100 |
| 68 | 100 | 100 |
| 69 | 100 | 100 |
| 70 | 100 | 100 |
| 71 | 100 | 100 |
| 72 | 100 | 100 |
| 73 | 100 | 100 |
| 74 | 100 | 100 |
| 75 | 100 | 100 |
| 76 | 100 | 100 |
| 77 | 100 | 100 |
| 78 | 100 | 100 |
| 81 | 100 | 100 |
| 82 | 100 | 100 |
| 83 | 100 | 100 |
| 84 | 100 | 100 |
| 85 | 100 | 100 |
| 86 | 100 | 100 |
| 87 | 100 | 100 |
| 88 | 100 | 100 |
| 89 | 100 | 100 |
| 92 | 100 | 100 |
| 93 | 100 | 100 |
| 94 | 100 | 100 |
| 95 | 100 | 100 |
| 96 | 100 | 100 |
| 97 | 100 | 100 |
| 98 | 100 | 100 |
| 99 | 100 | 100 |
| 100 | 100 | 100 |
| 101 | 100 | 100 |
| 102 | 100 | 100 |
| 103 | 100 | 100 |
| 104 | 100 | 100 |
| 105 | 100 | 100 |
| 106 | 100 | 100 |
| 107 | 100 | 100 |
| 108 | 100 | 100 |
| 109 | 100 | 100 |
| 110 | 100 | 100 |
| 115 | 100 | 100 |
| 119 | 100 | 100 |
| 120 | 100 | 100 |
| 125 | 100 | 100 |
| 126 | 100 | 100 |
| 127 | 100 | 100 |
| 128 | 100 | 100 |
| 129 | 100 | 100 |
| 130 | 100 | 100 |
| 131 | 100 | 100 |
| 132 | 100 | 100 |
| 133 | 100 | 100 |
| 134 | 100 | 100 |
| 135 | 100 | 100 |
| 136 | 100 | 100 |
| 137 | 100 | 100 |
| 138 | 100 | 100 |
| 140 | 100 | 100 |
| 141 | 100 | 100 |
| 142 | 100 | 100 |
| 143 | 100 | 100 |
| 144 | 100 | 100 |
| 145 | 100 | 100 |
| 146 | 100 | 100 |
| 150 | 100 | 100 |
| 152 | 100 | 100 |
| 153 | 100 | 100 |
| 155 | 100 | 100 |
| 156 | 100 | 100 |
| 157 | 100 | 100 |
| 158 | 100 | 100 |
| 159 | 100 | 100 |
| 160 | 100 | 100 |
| 161 | 100 | 100 |
| 162 | 100 | 100 |
| 163 | 100 | 100 |
| 164 | 100 | 100 |
| 165 | 100 | 100 |
| 166 | 100 | 100 |
| 167 | 100 | 100 |
| 168 | 100 | 100 |

TABLE 3-continued

| Compound Number | acaricidal rate (%)* 500 ppm | 100 ppm |
|---|---|---|
| 169 | 100 | 100 |
| 170 | 100 | 100 |
| 171 | 100 | 100 |
| 172 | 100 | 100 |
| 173 | 100 | 100 |
| 174 | 100 | 100 |
| 175 | 100 | 100 |
| 176 | 100 | 100 |
| 177 | 100 | 100 |
| 178 | 100 | 100 |
| 179 | 100 | 100 |
| 180 | 100 | 100 |
| 181 | 100 | 100 |
| 182 | 100 | 100 |
| 183 | 100 | 100 |
| 184 | 100 | 100 |
| 185 | 100 | 100 |
| 186 | 100 | 100 |
| 187 | 100 | 100 |
| 188 | 100 | 100 |
| 189 | 100 | 100 |
| 190 | 100 | 100 |
| 191 | 100 | 100 |
| 192 | 100 | 100 |
| 193 | 100 | 100 |
| 194 | 100 | 100 |
| 195 | 100 | 100 |
| 196 | 100 | 100 |
| 197 | 100 | 100 |
| 198 | 100 | 100 |
| 199 | 100 | 100 |
| 200 | 100 | 100 |
| 201 | 100 | 100 |
| 202 | 100 | 100 |
| 203 | 100 | 100 |
| 204 | 100 | 100 |
| 205 | 100 | 100 |
| 206 | 100 | 100 |
| 207 | 100 | 100 |
| 208 | 100 | 100 |
| 209 | 100 | 100 |
| 211 | 100 | 100 |
| 212 | 100 | 100 |
| 213 | 100 | 100 |
| 214 | 100 | 100 |
| 215 | 100 | 100 |
| 216 | 100 | 100 |
| 217 | 100 | 100 |
| 218 | 100 | 100 |
| 219 | 100 | 100 |
| 220 | 100 | 100 |
| 221 | 100 | 100 |
| 222 | 100 | 100 |
| 223 | 100 | 100 |
| 224 | 100 | 100 |
| 225 | 100 | 100 |
| 228 | 100 | 100 |
| 229 | 100 | 100 |
| 230 | 100 | 100 |
| 231 | 100 | 100 |
| 232 | 100 | 100 |
| 233 | 100 | 100 |
| 234 | 100 | 100 |
| 235 | 100 | 100 |
| 236 | 100 | 100 |
| 237 | 100 | 100 |
| 238 | 100 | 100 |
| 239 | 100 | 100 |
| 240 | 100 | 100 |
| 242 | 100 | 100 |
| 243 | 100 | 100 |
| 244 | 100 | 100 |
| 245 | 100 | 100 |
| 246 | 100 | 100 |
| 247 | 100 | 100 |
| 248 | 100 | 100 |
| 249 | 100 | 100 |
| 250 | 100 | 100 |
| 251 | 100 | 100 |
| 252 | 100 | 100 |
| 253 | 100 | 100 |
| 254 | 100 | 100 |
| 255 | 100 | 100 |
| 256 | 100 | 100 |
| 257 | 100 | 100 |
| 258 | 100 | 100 |
| 259 | 100 | 100 |
| 260 | 100 | 100 |
| 261 | 100 | 100 |
| 262 | 100 | 100 |
| 263 | 100 | 100 |
| 264 | 100 | 100 |
| 265 | 100 | 100 |
| 266 | 100 | 100 |
| 267 | 100 | 100 |
| 268 | 100 | 100 |
| 269 | 100 | 100 |
| 270 | 100 | 100 |
| 271 | 100 | 100 |
| 272 | 100 | 100 |
| 273 | 100 | 100 |
| 274 | 100 | 100 |
| 275 | 100 | 100 |
| 276 | 100 | 100 |
| 277 | 100 | 100 |
| 278 | 100 | 100 |
| 279 | 100 | 100 |
| 280 | 100 | 100 |
| 281 | 100 | 100 |
| 282 | 100 | 100 |
| 283 | 100 | 100 |
| 284 | 100 | 100 |
| 785 | 100 | 100 |
| 286 | 100 | 100 |
| 287 | 100 | 100 |
| 288 | 100 | 100 |
| 289 | 100 | 100 |
| 290 | 100 | 100 |
| 291 | 100 | 100 |
| 292 | 100 | 100 |
| 293 | 100 | 100 |
| 294 | 100 | 100 |
| 296 | 100 | 100 |
| 297 | 100 | 100 |
| 298 | 100 | 100 |
| 299 | 100 | 100 |
| 300 | 100 | 100 |
| 302 | 100 | 100 |
| 303 | 100 | 100 |
| 304 | 100 | 100 |
| 305 | 100 | 100 |
| 306 | 100 | 100 |
| 307 | 100 | 100 |
| 308 | 100 | 100 |
| 310 | 100 | 100 |
| 311 | 100 | 100 |
| 312 | 100 | 100 |
| 313 | 100 | 100 |
| 315 | 100 | 100 |
| 316 | 100 | 100 |
| 317 | 100 | 100 |
| 318 | 100 | 100 |
| 321 | 100 | 100 |
| 322 | 100 | 100 |
| 323 | 100 | 100 |
| 324 | 100 | 100 |
| 325 | 100 | 100 |
| 326 | 100 | 100 |
| 327 | 100 | 100 |
| 328 | 100 | 100 |
| 329 | 100 | 100 |
| 330 | 100 | 100 |
| 331 | 100 | 100 |
| 332 | 100 | 100 |
| 333 | 100 | 100 |
| 334 | 100 | 100 |
| 335 | 100 | 100 |
| 336 | 100 | 100 |

TABLE 3-continued

| Compound Number | acaricidal rate (%)* | |
|---|---|---|
| | 500 ppm | 100 ppm |
| 339 | 100 | 100 |
| 340 | 100 | 100 |
| 341 | 100 | 100 |
| 342 | 100 | 100 |
| 343 | 100 | 100 |
| 344 | 100 | 100 |
| 345 | 100 | 100 |
| 346 | 100 | 100 |
| 347 | 100 | 100 |
| 348 | 100 | 100 |
| 349 | 100 | 100 |
| 350 | 100 | 100 |
| 351 | 100 | 100 |
| 352 | 100 | 100 |
| 353 | 100 | 100 |
| 354 | 100 | 100 |
| 355 | 100 | 100 |
| 356 | 100 | 100 |
| 357 | 100 | 100 |
| 358 | 100 | 100 |
| 359 | 100 | 100 |
| 360 | 100 | 100 |
| 361 | 100 | 100 |
| 362 | 100 | 100 |
| 363 | 100 | 100 |
| 364 | 100 | 100 |
| 365 | 100 | 100 |
| 366 | 100 | 100 |
| 367 | 100 | 100 |
| 368 | 100 | 100 |
| 369 | 100 | 100 |
| 370 | 100 | 100 |
| 371 | 100 | 100 |
| 372 | 100 | 100 |
| 373 | 100 | 100 |
| 374 | 100 | 100 |
| 375 | 100 | 100 |
| 376 | 100 | 100 |
| 377 | 100 | 100 |
| 378 | 100 | 100 |
| 379 | 100 | 100 |
| 380 | 100 | 100 |
| 381 | 100 | 100 |
| 382 | 100 | 100 |
| 383 | 100 | 100 |
| 385 | 100 | 100 |
| 386 | 100 | 100 |
| 387 | 100 | 100 |
| 388 | 100 | 100 |
| 389 | 100 | 100 |
| 390 | 100 | 100 |
| 391 | 100 | 100 |
| 392 | 100 | 100 |
| 393 | 100 | 100 |
| 394 | 100 | 100 |
| Control A** | 100 | 60 |
| Control B*** | 0 | 0 |

*acaricidal rate (%) = $\frac{(\text{No. of hatched larvae} - \text{No. of imagoes}) \times 100}{\text{No. of hatched larvae}}$

**Control A = PESTICIDE BIOCHEMISTRY AND PHYSIOLOGY, 30, 190-197(1988) Compound No. AC-5

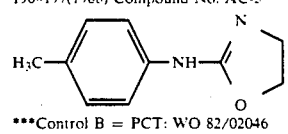

***Control B = PCT: WO 82/02046

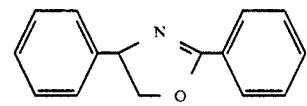

cl TEST EXAMPLE 4

Insecticidal Test for Nymphs of *Myzus persicae* Sulzer

Each 5 apterous imagoes of *Myzus persicae* Sulzer were placed on a radish seedling with two foliage leaves planted in a cup and allowed to produce nymphs for 3 days and then the imagoes were removed. Thereafter, a drug preparation (obtained by diluting the emulsifiable concentrate in Formulation Example 1 with water) with a predetermined concentration was spread thereon. The treated seedlings were placed in a green house to examine the number of living nymphs after 96 hours and the pesticidal rate was obtained. The test was conducted through 3 replications for each area. The results are shown in Table 4 below.

TEST EXAMPLE 5

Insecticidal Test for Nymphs of Cotton Aphid

Each 5 apterous imagoes of cotton aphid (*Aphis gossypii* Glover) were placed on a radish seedling with two foliage leaves planted in a cup and allowed to produce nymphs for 3 days and then the imagoes were removed. Thereafter, a drug preparation (obtained by diluting the emulsifiable concentrate in Formulation Example 1 with water) with a predetermined concentration was spread thereon. The treated seedlings were placed in a green house to examine the number of living nymphs after 96 hours and the pesticidal rate was obtained. The test was conducted through 3 replications for each area. The results are shown in Table 4 below.

TABLE 4

| | pesticidal rate (%)* | |
|---|---|---|
| Compound Number | Myzus persicae 500 ppm | Cotton aphid 500 ppm |
| 1 | 100 | 100 |
| 2 | 100 | 100 |
| 4 | 100 | 100 |
| 5 | 100 | 100 |
| 6 | 100 | 100 |
| 7 | 100 | 100 |
| 8 | 95 | 100 |
| 9 | 100 | 100 |
| 10 | 100 | 100 |
| 11 | 100 | 100 |
| 12 | 95 | 100 |
| 15 | 100 | 100 |
| 16 | 100 | 100 |
| 17 | 100 | 100 |
| 18 | 100 | 100 |
| 19 | 100 | 100 |
| 20 | 95 | 100 |
| 21 | 100 | 100 |
| 22 | 100 | 100 |
| 23 | 100 | 100 |
| 24 | 100 | 100 |
| 25 | 100 | 100 |
| 26 | 95 | 95 |
| 27 | 95 | 100 |
| 29 | 85 | 95 |
| 30 | 100 | 100 |
| 31 | 100 | 100 |
| 32 | 100 | 100 |
| 33 | 100 | 100 |
| 34 | 100 | 100 |
| 35 | 100 | 100 |
| 36 | 100 | 100 |
| 37 | 100 | 100 |
| 38 | 100 | 100 |
| 39 | 100 | 100 |
| 40 | 100 | 100 |
| 41 | 100 | 100 |
| 42 | 85 | 90 |
| 43 | 100 | 100 |
| 44 | 100 | 100 |
| 45 | 100 | 100 |
| 46 | 100 | 100 |
| 47 | 100 | 100 |
| 48 | 100 | 100 |
| 49 | 100 | 100 |
| 50 | 100 | 100 |
| 51 | 100 | 100 |

TABLE 4-continued

| Compound Number | pesticidal rate (%)* Myzus persicae 500 ppm | Cotton aphid 500 ppm |
|---|---|---|
| 53 | 85 | 95 |
| 60 | 100 | 100 |
| 61 | 100 | 100 |
| 62 | 100 | 100 |
| 63 | 100 | 100 |
| 64 | 100 | 100 |
| 65 | 100 | 100 |
| 66 | 100 | 100 |
| 67 | 100 | 100 |
| 71 | 85 | 100 |
| 73 | 90 | 90 |
| 75 | 85 | 95 |
| 76 | 100 | 100 |
| 77 | 100 | 100 |
| 78 | 100 | 100 |
| 79 | 95 | 100 |
| 81 | 100 | 100 |
| 82 | 100 | 100 |
| 83 | 95 | 100 |
| 84 | 100 | 100 |
| 84 | 100 | 100 |
| 85 | 100 | 100 |
| 86 | 100 | 100 |
| 87 | 100 | 100 |
| 88 | 95 | 100 |
| 89 | 100 | 100 |
| 92 | 85 | 100 |
| 93 | 100 | 100 |
| 94 | 100 | 100 |
| 95 | 100 | 100 |
| 96 | 100 | 100 |
| 98 | 100 | 100 |
| 100 | 100 | 100 |
| 101 | 95 | 100 |
| 102 | 100 | 100 |
| 103 | 85 | 90 |
| 104 | 100 | 100 |
| 106 | 95 | 100 |
| 119 | 85 | 85 |
| 120 | 100 | 100 |
| 125 | 100 | 100 |
| 126 | 100 | 100 |
| 127 | 100 | 100 |
| 128 | 100 | 100 |
| 129 | 100 | 100 |
| 130 | 95 | 100 |
| 131 | 100 | 100 |
| 133 | 100 | 100 |
| 134 | 100 | 100 |
| 135 | 100 | 100 |
| 137 | 100 | 100 |
| 138 | 100 | 100 |
| 141 | 100 | 100 |
| 144 | 100 | 100 |
| 145 | 100 | 100 |
| 146 | 85 | 85 |
| 147 | 100 | 100 |
| 149 | 85 | 90 |
| 152 | 100 | 100 |
| 153 | 100 | 100 |
| 155 | 100 | 100 |
| 156 | 100 | 100 |
| 157 | 100 | 100 |
| 158 | 95 | 100 |
| 159 | 100 | 100 |
| 160 | 100 | 100 |
| 161 | 100 | 100 |
| 162 | 100 | 100 |
| 163 | 100 | 100 |
| 164 | 100 | 100 |
| 166 | 100 | 100 |
| 167 | 100 | 100 |
| 168 | 100 | 100 |
| 169 | 100 | 100 |
| 170 | 95 | 95 |
| 172 | 100 | 100 |
| 173 | 100 | 100 |
| 174 | 100 | 100 |
| 175 | 100 | 100 |
| 176 | 100 | 100 |
| 177 | 100 | 100 |
| 178 | 100 | 100 |
| 180 | 100 | 100 |
| 181 | 100 | 100 |
| 182 | 100 | 100 |
| 183 | 100 | 100 |
| 184 | 100 | 100 |
| 185 | 100 | 100 |
| 188 | 100 | 100 |
| 189 | 100 | 100 |
| 190 | 100 | 100 |
| 191 | 100 | 100 |
| 193 | 100 | 100 |
| 194 | 100 | 100 |
| 195 | 100 | 100 |
| 196 | 100 | 100 |
| 197 | 100 | 100 |
| 198 | 100 | 100 |
| 199 | 100 | 100 |
| 200 | 100 | 100 |
| 201 | 100 | 100 |
| 202 | 100 | 100 |
| 203 | 100 | 100 |
| 206 | 100 | 100 |
| 207 | 100 | 100 |
| 211 | 100 | 100 |
| 212 | 100 | 100 |
| 213 | 100 | 100 |
| 214 | 100 | 100 |
| 215 | 100 | 100 |
| 216 | 100 | 100 |
| 218 | 100 | 100 |
| 220 | 100 | 100 |
| 221 | 100 | 100 |
| 223 | 100 | 100 |
| 224 | 100 | 100 |
| 225 | 100 | 100 |
| 226 | 100 | 100 |
| 227 | 85 | 100 |
| 228 | 100 | 100 |
| 229 | 100 | 100 |
| 230 | 100 | 100 |
| 231 | 100 | 100 |
| 232 | 100 | 100 |
| 233 | 100 | 100 |
| 234 | 100 | 100 |
| 235 | 100 | 100 |
| 237 | 100 | 100 |
| 238 | 100 | 100 |
| 239 | 100 | 100 |
| 240 | 100 | 100 |
| 242 | 100 | 100 |
| 243 | 100 | 100 |
| 244 | 100 | 100 |
| 246 | 100 | 100 |
| 247 | 100 | 100 |
| 248 | 100 | 100 |
| 249 | 100 | 100 |
| 251 | 100 | 100 |
| 254 | 100 | 100 |
| 255 | 100 | 100 |
| 256 | 100 | 100 |
| 257 | 100 | 100 |
| 259 | 85 | 90 |
| 260 | 100 | 100 |
| 261 | 100 | 100 |
| 262 | 100 | 100 |
| 263 | 95 | 100 |
| 264 | 100 | 100 |
| 265 | 100 | 100 |
| 266 | 100 | 100 |
| 267 | 100 | 100 |
| 269 | 100 | 100 |
| 270 | 100 | 100 |

TABLE 4-continued

| Compound Number | pesticidal rate (%)* Myzus persicae 500 ppm | Cotton aphid 500 ppm |
|---|---|---|
| 273 | 95 | 100 |
| 274 | 100 | 100 |
| 275 | 100 | 100 |
| 276 | 100 | 100 |
| 277 | 100 | 100 |
| 278 | 100 | 100 |
| 279 | 100 | 100 |
| 280 | 100 | 100 |
| 281 | 100 | 100 |
| 282 | 100 | 100 |
| 283 | 100 | 100 |
| 284 | 100 | 100 |
| 285 | 85 | 100 |
| 286 | 100 | 100 |
| 287 | 100 | 100 |
| 288 | 100 | 100 |
| 289 | 100 | 100 |
| 290 | 100 | 100 |
| 291 | 100 | 100 |
| 292 | 100 | 100 |
| 293 | 100 | 100 |
| 294 | 100 | 100 |
| 296 | 100 | 100 |
| 298 | 95 | 95 |
| 300 | 85 | 95 |
| 302 | 100 | 100 |
| 303 | 95 | 100 |
| 304 | 100 | 100 |
| 305 | 90 | 90 |
| 306 | 85 | 90 |
| 307 | 95 | 100 |
| 308 | 100 | 100 |
| 310 | 85 | 100 |
| 312 | 100 | 100 |
| 316 | 85 | 90 |
| 318 | 85 | 95 |
| 321 | 85 | 90 |
| 322 | 95 | 100 |
| 323 | 85 | 100 |
| 324 | 100 | 100 |
| 325 | 95 | 100 |
| 326 | 85 | 100 |
| 330 | 95 | 100 |
| 335 | 100 | 100 |
| 339 | 95 | 95 |
| 340 | 100 | 100 |
| 345 | 95 | 100 |
| 346 | 85 | 95 |
| 348 | 100 | 100 |
| 349 | 95 | 95 |
| 350 | 100 | 100 |
| 351 | 100 | 100 |
| 352 | 95 | 100 |
| 353 | 85 | 95 |
| 355 | 95 | 95 |
| 356 | 100 | 100 |
| 357 | 100 | 100 |
| 358 | 100 | 100 |
| 359 | 100 | 100 |
| 360 | 100 | 100 |
| 361 | 100 | 100 |
| 362 | 100 | 100 |
| 363 | 100 | 100 |
| 364 | 100 | 100 |
| 365 | 100 | 100 |
| 366 | 100 | 100 |
| 368 | 100 | 100 |
| 369 | 100 | 100 |
| 370 | 100 | 100 |
| 371 | 100 | 100 |
| 372 | 100 | 100 |
| 373 | 100 | 100 |
| 374 | 100 | 100 |
| 375 | 100 | 100 |
| 376 | 85 | 90 |
| 377 | 100 | 100 |
| 378 | 100 | 100 |
| 379 | 100 | 100 |
| 380 | 100 | 100 |
| 381 | 100 | 100 |
| 382 | 100 | 100 |
| 383 | 100 | 100 |
| 384 | 85 | 95 |
| 385 | 100 | 100 |
| 386 | 100 | 100 |
| 387 | 100 | 100 |
| 388 | 100 | 100 |
| 389 | 100 | 100 |
| 390 | 100 | 100 |
| 391 | 100 | 100 |
| 392 | 85 | 95 |
| 394 | 85 | 85 |
| Control B** | 0 | 0 |
| Control C*** | 50 | 20 |

*pesticidal rate (%) = $\frac{\text{No. of parasites before spreading} - \text{No. of parasites at inspection}}{\text{No. of parasites before spreading}} \cdot 100$

**Control B = PCT:WO 82/02046

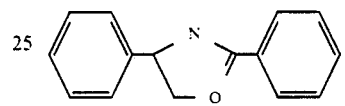

***Control C = Pirimicarb

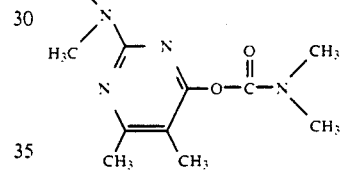

TEST EXAMPLE 6

Opesticidal Test for Nymphs of *Nephotettix cincticeps*

Each 10 nymphs of *Nephotettix cincticepscae* were inoculated to rice seedlings which were previously planted in cups and treated by spreading a drug preparation (obtained by diluting the emulsifiable concentrate in Formulation Example 1 with water) with a predetermined concentration followed by air-drying and the cups were covered with each an acrylic resin cylinder with a gauze wrap. The treated seedlings were placed in a green house to examine the number of nymphs after 7 days and the pesticidal rate was obtained. The test was conducted through 3 replications for each area. The results are shown in Table 5 below.

TABLE 5

| Compound Number | pesticidal rate (%)* 500 ppm |
|---|---|
| 5 | 85 |
| 12 | 95 |
| 22 | 85 |
| 30 | 85 |
| 50 | 100 |
| 51 | 100 |
| 66 | 95 |
| 67 | 100 |
| 68 | 95 |
| 69 | 100 |
| 70 | 85 |
| 71 | 85 |
| 76 | 100 |
| 77 | 100 |

TABLE 5-continued

| Compound Number | pesticidal rate (%)* 500 ppm |
|---|---|
| 78 | 100 |
| 81 | 85 |
| 82 | 85 |
| 105 | 95 |
| 118 | 85 |
| 121 | 100 |
| 128 | 100 |
| 129 | 85 |
| 133 | 100 |
| 145 | 85 |
| 146 | 85 |
| 164 | 85 |
| 167 | 85 |
| 173 | 85 |
| 175 | 95 |
| 186 | 100 |
| 206 | 85 |
| 211 | 100 |
| 224 | 90 |
| 225 | 90 |
| 230 | 100 |
| 231 | 100 |
| 232 | 100 |
| 234 | 100 |
| 235 | 95 |
| 236 | 90 |
| 237 | 100 |
| 238 | 100 |
| 239 | 100 |
| 240 | 100 |
| 242 | 90 |
| 243 | 85 |
| 244 | 90 |
| 246 | 100 |
| 247 | 100 |
| 248 | 100 |
| 249 | 100 |
| 254 | 100 |
| 255 | 95 |
| 256 | 100 |
| 257 | 100 |
| 266 | 85 |
| 270 | 85 |
| 280 | 85 |
| 281 | 100 |
| 282 | 100 |
| 283 | 95 |
| 288 | 95 |
| 294 | 85 |
| 296 | 95 |
| 305 | 90 |
| 306 | 85 |
| 312 | 95 |
| 329 | 95 |
| 346 | 85 |
| 357 | 85 |
| 358 | 100 |
| 382 | 95 |
| 383 | 95 |
| Control B** | 0 |

*pesticidal rate (%) = $\frac{\text{No. of parasites before spreading} - \text{No. of parasites at inspection}}{\text{No. of parasites before spreading}} \times 100$

**Control B = PCT WO 82/02046

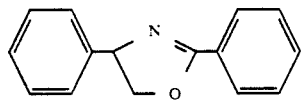

TEST EXAMPLE 7

Pesticidal Test for Larvae of Diamondback Moth

Each 15 hatched larvae of diamondback moth (*Plutella xylostella* Linne) were placed in a cup (9 cm in diameter) with a piece of cabbage leaf (2 cm square) previously dipped in a drug preparation (obtained by diluting the emulsifiable concentrate in Formulation Example 1 with water) with a predetermined concentration followed by air-drying to examine the pesticidal rate after 4 days. The test was conducted through 3 replications for each area. The results are shown in Table 6 below.

TABLE 6

| Compound Number | pesticidal rate (%)* 500 ppm |
|---|---|
| 6 | 90 |
| 7 | 100 |
| 12 | 100 |
| 16 | 100 |
| 17 | 90 |
| 20 | 100 |
| 21 | 100 |
| 22 | 90 |
| 26 | 100 |
| 27 | 100 |
| 28 | 90 |
| 29 | 90 |
| 32 | 100 |
| 33 | 90 |
| 34 | 100 |
| 36 | 100 |
| 37 | 100 |
| 38 | 100 |
| 39 | 100 |
| 40 | 100 |
| 41 | 90 |
| 42 | 100 |
| 43 | 100 |
| 44 | 90 |
| 45 | 100 |
| 46 | 100 |
| 48 | 90 |
| 50 | 100 |
| 51 | 100 |
| 52 | 100 |
| 53 | 100 |
| 54 | 100 |
| 55 | 100 |
| 58 | 90 |
| 60 | 90 |
| 61 | 90 |
| 62 | 100 |
| 63 | 90 |
| 64 | 90 |
| 65 | 90 |
| 66 | 90 |
| 67 | 100 |
| 68 | 90 |
| 69 | 90 |
| 70 | 90 |
| 71 | 100 |
| 72 | 100 |
| 73 | 100 |
| 74 | 90 |
| 76 | 90 |
| 77 | 100 |
| 78 | 100 |
| 85 | 100 |
| 86 | 100 |
| 89 | 90 |
| 92 | 100 |
| 93 | 90 |
| 94 | 100 |
| 95 | 100 |
| 96 | 100 |
| 103 | 90 |
| 119 | 90 |
| 120 | 90 |
| 136 | 100 |
| 137 | 100 |
| 138 | 100 |
| 141 | 100 |
| 144 | 90 |
| 145 | 100 |
| 149 | 90 |
| 152 | 90 |

TABLE 6-continued

| Compound Number | pesticidal rate (%)* 500 ppm |
|---|---|
| 153 | 100 |
| 154 | 90 |
| 155 | 100 |
| 156 | 100 |
| 157 | 100 |
| 158 | 100 |
| 159 | 100 |
| 161 | 100 |
| 162 | 100 |
| 163 | 100 |
| 164 | 100 |
| 165 | 100 |
| 166 | 100 |
| 167 | 100 |
| 168 | 100 |
| 169 | 100 |
| 170 | 100 |
| 171 | 100 |
| 172 | 100 |
| 173 | 100 |
| 174 | 100 |
| 175 | 100 |
| 176 | 100 |
| 177 | 100 |
| 178 | 100 |
| 179 | 90 |
| 180 | 90 |
| 181 | 100 |
| 182 | 100 |
| 183 | 100 |
| 184 | 100 |
| 185 | 100 |
| 188 | 100 |
| 189 | 100 |
| 190 | 100 |
| 191 | 100 |
| 192 | 100 |
| 193 | 100 |
| 194 | 100 |
| 195 | 100 |
| 196 | 100 |
| 197 | 100 |
| 198 | 100 |
| 199 | 100 |
| 200 | 90 |
| 201 | 90 |
| 202 | 100 |
| 203 | 100 |
| 204 | 100 |
| 206 | 100 |
| 207 | 90 |
| 209 | 90 |
| 211 | 100 |
| 212 | 100 |
| 213 | 100 |
| 214 | 100 |
| 215 | 100 |
| 216 | 100 |
| 217 | 90 |
| 218 | 90 |
| 219 | 90 |
| 220 | 90 |
| 221 | 100 |
| 223 | 100 |
| 224 | 100 |
| 225 | 100 |
| 226 | 100 |
| 227 | 100 |
| 228 | 100 |
| 229 | 100 |
| 230 | 100 |
| 231 | 100 |
| 232 | 100 |
| 233 | 100 |
| 234 | 100 |
| 237 | 100 |
| 238 | 100 |
| 239 | 100 |
| 240 | 100 |
| 242 | 100 |
| 243 | 100 |
| 244 | 100 |
| 246 | 100 |
| 247 | 100 |
| 248 | 100 |
| 249 | 100 |
| 250 | 100 |
| 251 | 100 |
| 252 | 100 |
| 253 | 100 |
| 254 | 100 |
| 255 | 100 |
| 256 | 100 |
| 257 | 100 |
| 261 | 100 |
| 262 | 100 |
| 273 | 90 |
| 282 | 100 |
| 283 | 100 |
| 284 | 100 |
| 291 | 100 |
| 292 | 100 |
| 297 | 100 |
| 298 | 100 |
| 303 | 100 |
| 304 | 100 |
| 330 | 90 |
| 331 | 90 |
| 332 | 90 |
| 336 | 100 |
| 341 | 100 |
| 345 | 100 |
| 348 | 100 |
| 352 | 100 |
| 356 | 100 |
| 357 | 100 |
| 358 | 100 |
| 359 | 100 |
| 360 | 100 |
| 361 | 100 |
| 362 | 100 |
| 363 | 100 |
| 364 | 100 |
| 365 | 100 |
| 366 | 100 |
| 367 | 100 |
| 368 | 100 |
| 370 | 100 |
| 371 | 100 |
| 374 | 100 |
| 375 | 100 |
| 377 | 90 |
| 378 | 100 |
| 379 | 90 |
| 381 | 100 |
| 382 | 100 |
| 383 | 100 |
| 389 | 90 |
| Control B** | 0 |

*pesticidal rate (%) = $\frac{\text{No. of inoculated larvae} - \text{No. of larvae at examination}}{\text{No. of inoculated larvae}} \cdot 100$

**Control B = PCT:WO 82/02046

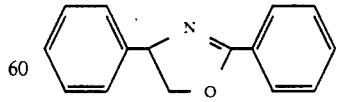

TEST EXAMPLE 8 cl Pesticidal Test for Larvae of Culex-pipiens

Each of about 15 of second inster larvae of *Culex-pipiens* were inoculated in a cup of 120 ml capacity contining 50 ml of a drug preparation (obtained by diluting the emulsifiable concentrate in Formulation Example 1 with water) with a predetermined concentration added with a very small amount of dry yeast powder as a feed. The number of third inster larvae was counted after after 3 days from turning out and the pesticidal rate was determined. The test was conducted through 3 replications for each area. The results are shown in Table 7 below.

TABLE 7

| Compound Number | pesticidal rate (%)* 1 ppm |
|---|---|
| 1 | 100 |
| 2 | 100 |
| 6 | 100 |
| 7 | 100 |
| 12 | 100 |
| 16 | 100 |
| 17 | 100 |
| 20 | 100 |
| 21 | 100 |
| 22 | 100 |
| 26 | 100 |
| 27 | 100 |
| 29 | 98 |
| 32 | 100 |
| 33 | 97.8 |
| 34 | 100 |
| 36 | 100 |
| 37 | 100 |
| 38 | 100 |
| 39 | 100 |
| 40 | 100 |
| 41 | 100 |
| 42 | 100 |
| 45 | 100 |
| 46 | 100 |
| 48 | 100 |
| 50 | 97 |
| 51 | 100 |
| 52 | 100 |
| 53 | 95.8 |
| 54 | 100 |
| 55 | 100 |
| 58 | 100 |
| 60 | 100 |
| 61 | 98 |
| 62 | 100 |
| 63 | 98.8 |
| 64 | 100 |
| 65 | 100 |
| 66 | 100 |
| 67 | 100 |
| 69 | 100 |
| 70 | 100 |
| 71 | 100 |
| 73 | 100 |
| 76 | 100 |
| 77 | 100 |
| 78 | 100 |
| 81 | 100 |
| 82 | 100 |
| 85 | 96.6 |
| 86 | 100 |
| 88 | 100 |
| 89 | 93.8 |
| 92 | 100 |
| 93 | 100 |
| 94 | 100 |
| 95 | 100 |
| 96 | 100 |
| 100 | 100 |
| 102 | 96.8 |
| 103 | 100 |
| 106 | 100 |
| 119 | 97.1 |
| 120 | 100 |
| 125 | 100 |
| 126 | 100 |
| 127 | 100 |
| 128 | 100 |

TABLE 7-continued

| Compound Number | pesticidal rate (%)* 1 ppm |
|---|---|
| 129 | 100 |
| 130 | 100 |
| 131 | 100 |
| 133 | 100 |
| 134 | 100 |
| 135 | 100 |
| 136 | 100 |
| 137 | 100 |
| 138 | 96.6 |
| 141 | 100 |
| 144 | 92.9 |
| 145 | 93.8 |
| 152 | 100 |
| 155 | 100 |
| 156 | 100 |
| 157 | 100 |
| 159 | 97 |
| 160 | 100 |
| 161 | 96.8 |
| 162 | 100 |
| 163 | 100 |
| 164 | 97.1 |
| 165 | 100 |
| 166 | 100 |
| 167 | 100 |
| 168 | 100 |
| 169 | 100 |
| 170 | 100 |
| 171 | 100 |
| 172 | 100 |
| 173 | 100 |
| 174 | 100 |
| 175 | 100 |
| 176 | 100 |
| 177 | 100 |
| 178 | 100 |
| 181 | 95.7 |
| 182 | 100 |
| 183 | 100 |
| 184 | 100 |
| 185 | 100 |
| 188 | 100 |
| 189 | 97 |
| 190 | 100 |
| 191 | 97.1 |
| 194 | 94.4 |
| 195 | 100 |
| 196 | 100 |
| 197 | 100 |
| 198 | 100 |
| 199 | 100 |
| 200 | 100 |
| 201 | 100 |
| 202 | 100 |
| 203 | 100 |
| 206 | 100 |
| 207 | 100 |
| 211 | 100 |
| 212 | 100 |
| 213 | 100 |
| 214 | 96.2 |
| 215 | 100 |
| 216 | 100 |
| 219 | 100 |
| 220 | 100 |
| 221 | 100 |
| 223 | 100 |
| 228 | 100 |
| 229 | 100 |
| 230 | 100 |
| 231 | 96.5 |
| 232 | 100 |
| 233 | 100 |
| 237 | 100 |
| 238 | 100 |
| 239 | 100 |
| 240 | 100 |
| 242 | 100 |
| 243 | 100 |

TABLE 7-continued

| Compound Number | pesticidal rate (%)* 1 ppm |
|---|---|
| 244 | 100 |
| 246 | 100 |
| 247 | 100 |
| 248 | 100 |
| 249 | 100 |
| 250 | 100 |
| 251 | 100 |
| 252 | 100 |
| 253 | 100 |
| 254 | 100 |
| 255 | 100 |
| 256 | 100 |
| 257 | 100 |
| 264 | 100 |
| 269 | 100 |
| 270 | 96.4 |
| 273 | 100 |
| 274 | 100 |
| 277 | 100 |
| 278 | 100 |
| 279 | 100 |
| 283 | 100 |
| 284 | 100 |
| 288 | 93.3 |
| 303 | 96.2 |
| 304 | 100 |
| 305 | 100 |
| 306 | 100 |
| 307 | 100 |
| 316 | 100 |
| 324 | 92.7 |
| 325 | 100 |
| 335 | 100 |
| 336 | 97 |
| 340 | 100 |
| 341 | 100 |
| 345 | 100 |
| 347 | 100 |
| 350 | 100 |
| 351 | 95.5 |
| 352 | 94.6 |
| 353 | 96.8 |
| 356 | 96.8 |
| 357 | 96.9 |
| 358 | 93.3 |
| 359 | 100 |
| 360 | 100 |
| 361 | 96.8 |
| 362 | 100 |
| 363 | 93.5 |
| 364 | 93.1 |
| 365 | 100 |
| 366 | 100 |
| 367 | 100 |
| 368 | 100 |
| 369 | 100 |
| 370 | 96.9 |
| 374 | 96.9 |
| 372 | 100 |
| 373 | 96.7 |
| 371 | 100 |
| 375 | 100 |
| 376 | 100 |
| 377 | 100 |
| Control B** | 0 |

*pesticidal rate (%) = $\frac{\text{No. of inoculated larvae} - \text{No. of larvae at examination}}{\text{No. of inoculated larvae}} \times 100$

**Control B = PCT:WO 82/02046

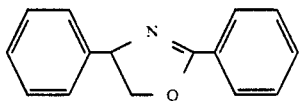

What we claim is:

1. A compound represented by the formula (I)

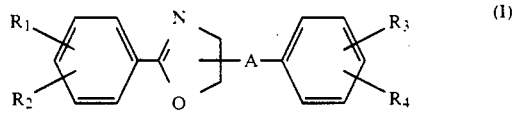

in which

R$_1$ and R$_2$ may be the same or different and each represents a hydrogen atom, a halogen atom, a lower alkyl group, a lower alkoxy group, a nitro group, a lower haloalkyl group or a lower haloalkoxy group, with a proviso that R$_1$ and R$_2$ do not simultaneously represent hydrogen atoms;

R$_3$ represents a hydrogen atom, a halogen atom, a lower alkyl group or a lower alkoxy group;

R$_4$ represents an alkyl group having 7 to 15 carbon atoms, an alkoxy group having 7 to 15 carbon atoms, an alkylthio group having 7 to 15 carbon atoms, a lower alkoxy-lower alkyl group, a lower alkoxy-lower alkoxy group, an alkenyloxy group having 3 to 10 carbon atoms, a lower alkynyloxy group, a cyclohexyl group which may be substituted by a lower alkyl group, or a group indicated by

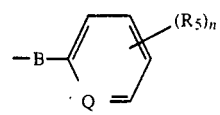

wherein

B is a direct bond, an oxygen atom, a lower alkylene group, a lower alkyleneoxy group or a lower alkylenedioxy group, Q is CH, n is 0 or an integer from 1 to 5, each R$_5$ is a halogen atom, a C$_1$ to C$_{10}$ alkyl group, a lower alkoxy group, a lower haloalkyl group or a lower haloalkoxy group, and when n is greater than 1, R$_{51}$'s may be the same or different;

A represents a direct bond or a lower alkylene group; and

Z represents an oxygen atom or a sulphur atom.

2. A compound of claim 1, in which R$_1$ and R$_2$ may be same or different and each represents a hydrogen atom, a halogen atom, a methyl group, a methoxy group, a nitro group, a trifluoromethyl group or a trifluoromethoxy group, with a proviso that R$_1$ and R$_2$ do not simultaneously represent hydrogen atoms.

3. A compound of claim 1, in which said R$_1$ and R$_2$ are located at the 12-, 4- or 6-position of the phenyl group.

4. A compound of claim 1, in which each of said R$_1$ and R$_2$ represents a halogen atom selected from a fluorine atom and a chlorine atom.

5. A compound of claim 1, in which sad R$_4$ is located at the 4-position of the phenyl group.

6. A compound of claim 1, in which said R$_4$ represents an alkyl group having 7 to 12 carbon atoms or a group of the formula

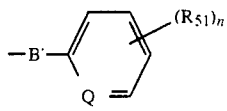

wherein B' is a direct bond, —O—, —CH$_2$—, or —OCH$_2$—, Q is CH, n is 0 or an integer from 1 to 5 and each R$_{51}$ represents a halogen atom, a C$_1$ to C$_{10}$ alkyl group or lower alkoxy group, and when n is greater than 1, R$_{51}$'s may be same or different.

7. A compound of claim 1, in which said A represents a direct bond.

8. A compound of claim 1, in which said Z represents an oxygen atom.

9. A compound of claim 1, which is represented by the formula

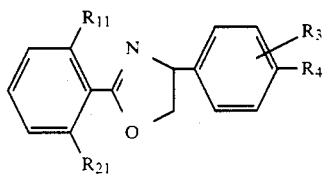
(I-a)

in which

R$_{11}$ and R$_{21}$ may be same or different and each represents a halogen atom, and each of R$_3$ and R$_4$ has the same meaning as described in claim 1.

10. A compound of claim 8, which is represented by the formula

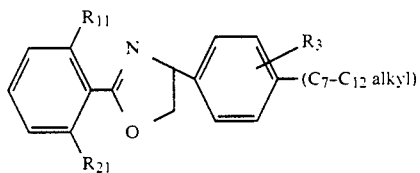
(I-b)

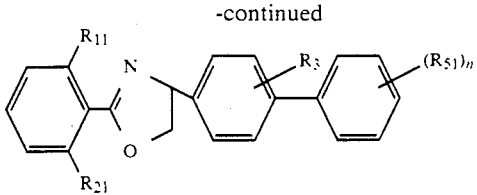
(I-c)

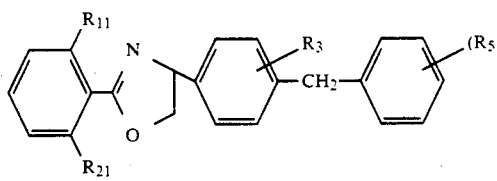
(I-d)

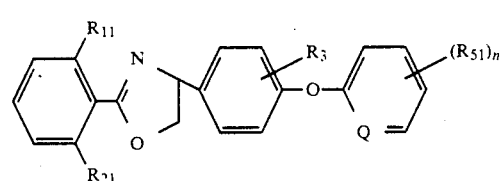
(I-e)

or

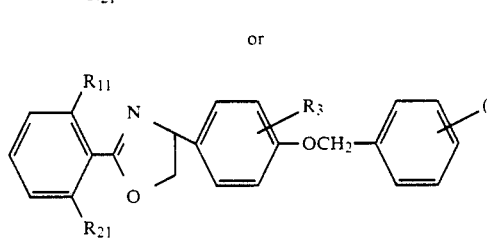
(I-f)

in which each R$_{51}$ is a halogen atom, a C$_1$–C$_{10}$ alkyl group or a lower alkoxy group, and when n is greater than 1, R$_{51}$'s may be same or different; each of R$_{11}$, R$_{21}$ and R$_3$ has the same meaning as described in claim 8, and Q is CH and n is 0 or an integer of from 1 to 5.

11. An insecticidal or acaricidal composition which comprises an insecticidally or acaricidally effective amount of a compound according to claim 1 and an insecticidally or acaricidally compatible carrier therefor.

12. A method for controlling noxious insects or mites which comprises applying to the said insects or mites or to their habitat an insecticidally or acaricidally effective amount of a compound as defined in claim 1.

* * * * *